(12) United States Patent
Markosyan et al.

(10) Patent No.: US 11,547,128 B2
(45) Date of Patent: Jan. 10, 2023

(54) MOGROSIDES AND USE THEREOF

(71) Applicant: PURECIRCLE USA INC., Oak Brook, IL (US)

(72) Inventors: Avetik Markosyan, Yerevan (AM); Siew Yin Chow, Selangor (MY); Saravanan Ramandach, Negeri Sembilan (MY)

(73) Assignee: PURECIRCLE USA INC., Westchester, IL (US)

( * ) Notice: Subject to any disclaimer, the term of this patent is extended or adjusted under 35 U.S.C. 154(b) by 0 days.

(21) Appl. No.: 16/348,444

(22) PCT Filed: Nov. 8, 2017

(86) PCT No.: PCT/US2017/060604
§ 371 (c)(1),
(2) Date: May 8, 2019

(87) PCT Pub. No.: WO2018/089469
PCT Pub. Date: May 17, 2018

(65) Prior Publication Data
US 2020/0187550 A1 Jun. 18, 2020

Related U.S. Application Data

(60) Continuation-in-part of application No. 14/792,594, filed on Jul. 6, 2015, now Pat. No. 11,419,351, which is a division of application No. 13/219,721, filed on Aug. 29, 2011, now Pat. No. 9,101,162.

(60) Provisional application No. 62/419,238, filed on Nov. 8, 2016, provisional application No. 61/379,729, filed on Sep. 3, 2010.

(51) Int. Cl.
| | |
|---|---|
| *A23L 2/60* | (2006.01) |
| *A23L 27/30* | (2016.01) |
| *C07J 17/00* | (2006.01) |
| *A61K 8/63* | (2006.01) |
| *A61K 8/97* | (2017.01) |
| *G01N 30/02* | (2006.01) |
| *A61Q 19/00* | (2006.01) |
| *A61K 8/9789* | (2017.01) |
| *A61K 8/9794* | (2017.01) |
| *A24B 13/00* | (2006.01) |

(52) U.S. Cl.
CPC .............. *A23L 2/60* (2013.01); *A23L 27/36* (2016.08); *A61K 8/63* (2013.01); *A61K 8/97* (2013.01); *C07J 17/005* (2013.01); *A23L 27/34* (2016.08); *A23V 2002/00* (2013.01); *A23V 2250/24* (2013.01); *A23V 2250/254* (2013.01); *A23V 2300/14* (2013.01); *A24B 13/00* (2013.01); *A61K 8/9789* (2017.08); *A61K 8/9794* (2017.08); *A61Q 19/00* (2013.01); *G01N 2030/027* (2013.01)

(58) Field of Classification Search
CPC ........ A23L 2/60; A23L 27/36; A23V 2250/24; A23V 2250/254
See application file for complete search history.

(56) References Cited

U.S. PATENT DOCUMENTS

| | | | |
|---|---|---|---|
| 6,124,442 A | 9/2000 | Zhou et al. | |
| 6,228,996 B1 | 5/2001 | Zhou | |
| 9,101,162 B2 | 8/2015 | Markosyan | |
| 2007/0116819 A1 | 5/2007 | Prakash et al. | |
| 2008/0108710 A1 | 5/2008 | Prakash et al. | |
| 2009/0196966 A1 | 8/2009 | West et al. | |
| 2010/0267847 A1 | 10/2010 | Yoshinaka et al. | |
| 2014/0271748 A1* | 9/2014 | Woodyer | A23L 2/60 424/401 |

FOREIGN PATENT DOCUMENTS

| | | |
|---|---|---|
| CN | 101029071 A | 9/2007 |
| CN | 101050230 A | 10/2007 |
| CN | 101407535 A | 4/2009 |
| CN | 104926907 A | 9/2015 |
| JP | 2001211854 A | 8/2011 |
| WO | 9418855 A1 | 9/1994 |
| WO | 2007062087 A2 | 5/2007 |
| WO | 2008030121 A1 | 3/2008 |
| WO | 2008149253 A2 | 12/2008 |
| WO | 2009023975 A2 | 2/2009 |
| WO | 2009063921 A1 | 5/2009 |
| WO | 2016038617 A1 | 3/2016 |
| WO | 2017075257 A2 | 5/2017 |

OTHER PUBLICATIONS

Spano, Marie MS, RD, CSCS Functional Foods, Beverages, and Ingredients in Athletics, Strength and Conditioning Journal: Feb. 2010—vol. 32—Issue 1—p. 79-86. (Year: 2010).*
European Search Report of patent application No. EP11179246.1 completed on Oct. 27, 2011 and dated Nov. 20, 2011 (6 pages).
Communication pursuant to Article 94(3) EPC of European patent application No. EP11179246.1 dated Oct. 17, 2012 (4 pages).
Natural High Potency Sweeteners by Kim et al., "Handbook of Sweeteners" by Marie et al. (Eds.), Springer Science & Business Media (New York), pp. 116-185, copyright 1991.
Isolation of the sweet components from Siraitia grosvenorli by Xia et al., Food Chem. 107, 1022-28 (2008).

(Continued)

Primary Examiner — Theodore R. Howell
(74) Attorney, Agent, or Firm — Rachael Casey

(57) ABSTRACT

The present invention provides a process for preparation of compositions comprising novel mogrosides from fruit of *Siraitia grosvenorii*. The compositions have superior organoleptic properties compared to known mogroside compositions and are useful in wider range of consumables including foods and beverages.

5 Claims, 68 Drawing Sheets

(56) References Cited

OTHER PUBLICATIONS

Extended European Search Report of patent application No. EP13160563.6 completed on Jun. 19, 2013 and dated Jun. 28, 2013 (5 pages).
Extended European Search Report of patent application No. EP17870309.6 completed on Jul. 7, 2020 (31 pages).
Venkata Sai Prakash Chaturvedula et al: "Cucurbitane Glycosides from Siraitia grosvenorii", Journal of Carbohydrate Chemistry,vol. 30, No. 1, Jan. 1, 2011 (Jan. 1, 2011), pp. 16-26.
Hongyang Zhang et al: "Identification of flavonol and triterpene glycosides in Luo-Han-Guo extract using ultra-high performance liquid chromatography/quadrupole time-of-flight mass spectrometry", Journal of Food Composition and Analysis, vol. 25, No. 2, Mar. 1, 2012 (Mar. 1, 2012), pp. 142-148.
Fu Li et al: Cucurbitane glycosides from the fruit of Siraitia grosvenori and their effects on glucose uptake in human HepG2 cells in vitro11, Food Chemistry, vol. 228, Feb. 10, 2017 (Feb. 10, 2017), pp. 567-573.

* cited by examiner

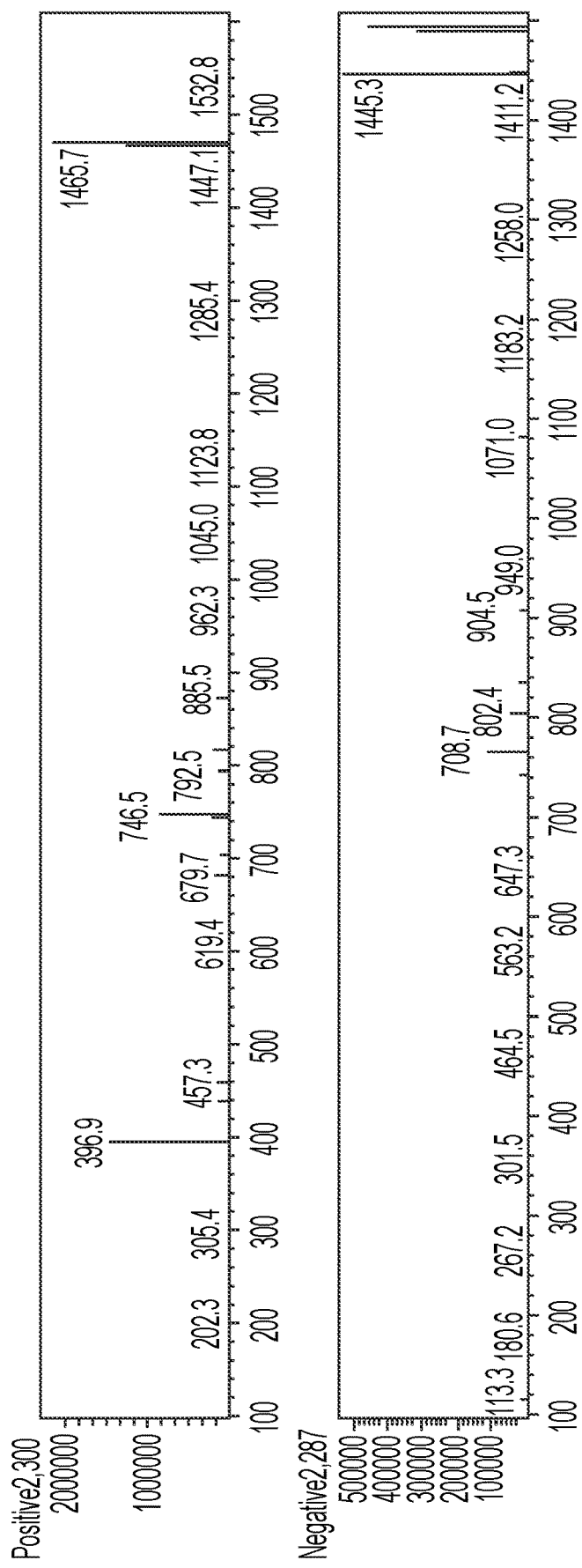

FIG. 30

| Position | $\delta_C$ [ppm] | $\delta_H$ [ppm] | J [Hz]/ (INT) | HMBC (H ->C) |
|---|---|---|---|---|
| Aglycon moiety | | | | |
| 1 | 21.5 t | 1.16 m | | |
| | | 1.47 m | | |
| 2 | 28.1 t | 1.70 m | | |
| | | 1.88 m | | |
| 3 | 86.7 d | 3.35 m | | 1$^i$ |
| 4 | 41.4 s | - | | |
| 5 | 140.8 s | - | | |
| 6 | 118.6 d | 5.51 m | | |
| 7 | 2.39 t | 1.86 m | | |
| | | 2.28 m | | |
| 8 | 44.5 d | 1.85 m | | |
| 9 | 49.9 s | - | | |
| 10 | 35.6 d | 2.34 m | | |
| 11 | 214.8 s | - | | |
| 12 | 48.8 t | 2.20 d | 13.5 Hz | |
| | | 3.00 d | | |
| 13 | 44.6 s | - | | |
| 14 | 35.0 s | - | | |
| 15 | 28.4 t | 1.24 m | | |
| | | 1.35 m | | |
| 16 | 28.7 t | 1.46 m | | |
| | | 2.03 m | | |
| 17 | 50.2 d | 1.70 m | | |
| 18 | 16.3 q | 0.66 s | (3H) | 12, 13, 14, 17 |
| 19 | 19.1 q | 0.96 s | (3H) | 8, 9, 10, 11 |
| 20 | 36.3 d | 1.32 m | | |
| 21 | 18.3 q | 0.85 d | 6.1 (3H) | 17, 20, 22 |
| 22 | 32.6 t | 1.30 m | | |
| | | 1.54 m | | |
| 23 | 33.0 t | 1.38 m | | |
| | | 1.45 m | | |
| 24 | 92.7 d | 3.32 m | | 1$^{iv}$ |
| 25 | 72.9 s | | | |
| 26 | 23.2 q | 1.05 s | (3H) | 24, 25, 27 |
| 27 | 25.7 q | 1.02 s | (3H) | 24, 25, 26 |
| 28 | 27.5 q | 0.97 s | (3H) | 3, 4, 5, 29 |
| 29 | 25.0 q | 1.13 s | (3H) | 3, 4, 5, 28 |
| 30 | 18.1 q | 1.02 s | (3H) | 8, 13, 14, 15 |

FIG. 31

| Position | $\delta_C$ [ppm] | $\delta_H$ [ppm] | J [Hz]/ (INT) | HMBC (H ->C) |
|---|---|---|---|---|
| Sugar moiety | | | | |
| β-D-Glucopyranoside | | | | |
| $1^i$ | 103.5 d | 4.20 d | 8.4 | 3 |
| $2^i$ | 74.2 d | 3.12 t | 8.4 | |
| $3^i$ | 77.0 d | 3.19 t | 8.4 | |
| $4^i$ | 71.0 d | 3.12 t | 8.4 | |
| $5^i$ | 76.1 d | 3.31 m | | |
| $6^i$ | 68.7 t | 3.69 m | | |
| | | 3.97 m | | |
| β-D-Glucopyranoside | | | | |
| $1^{ii}$ | 103.8 d | 4.28 d | 8.4 | $6^{ii}$ |
| $2^{ii}$ | 74.2 d | 3.09 t | 8.4 | |
| $3^{ii}$ | 77.2 d | 3.16 t | 8.4 | |
| $4^{ii}$ | 71.1 d | 3.16 t | 8.4 | |
| $5^{ii}$ | 76.2 d | 3.21 m | | |
| $6^{ii}$ | 61.6 t | 3.56 m | | |
| | | 3.76 m | | |
| β-D-Glucopyranoside | | | | |
| $1^{iii}$ | 103.8 d | 4.32 d | 8.4 | $6^i$ |
| $2^{iii}$ | 74.2 d | 3.11 t | 8.4 | |
| $3^{iii}$ | 76.7 d | 3.14 t | 8.4 | |
| $4^{iii}$ | 70.9 d | 3.17 t | 8.4 | |
| $5^{iii}$ | 76.1 d | 3.35 m | | |
| $6^{iii}$ | 69.2 t | 3.66 m | | |
| | | 4.05 m | | |
| β-D-Glucopyranoside | | | | |
| $1^{iv}$ | 103.5 d | 4.35 d | 8.4 | 24 |
| $2^{iv}$ | 79.6 d | 3.54 t | 8.4 | |
| $3^{iv}$ | 77.8 d | 3.51 t | 8.4 | |
| $4^{iv}$ | 70.4 d | 3.23 t | 8.4 | |
| $5^{iv}$ | 76.7 d | 3.27 m | | |
| $6^{iv}$ | 69.7 t | 3.42 m | | |
| | | 4.18 m | | |
| β-D-Glucopyranoside | | | | |
| $1^v$ | 103.4 d | 4.71 d | 8.4 | $2^{iv}$ |
| $2^v$ | 74.7 d | 3.18 t | 8.4 | |
| $3^v$ | 76.9 d | 3.24 t | 8.4 | |
| $4^v$ | 70.7 d | 3.19 t | 8.4 | |
| $5^v$ | 76.0 d | 3.27 m | | |
| $6^v$ | 62.0 t | 3.53 m | | |
| | | 3.77 m | | |
| β-D-Glucopyranoside | | | | |
| $1^{vi}$ | 105.4 d | 4.18 d | 8.4 | $6^{iv}$ |
| $2^{vi}$ | 74.6 d | 3.07 t | 8.4 | |
| $3^{vi}$ | 77.3 d | 3.11 t | 8.4 | |
| $4^{vi}$ | 71.1 d | 3.09 t | 8.4 | |
| $5^{vi}$ | 77.0 d | 3.22 m | | |
| $6^{vi}$ | 61.7 t | 3.55 m | | |
| | | 3.77 m | | |

TO FIG. 33B

FROM FIG. 33A

FIG. 34

| Position | δ_C [ppm] | δ_H [ppm] | J [Hz]/ (INT) | HMBC (H ->C) |
|---|---|---|---|---|
| Aglycon moiety | | | | |
| 1 | 21.3 t | 1.16 m | | |
| | | 1.46 m | | |
| 2 | 27.9 t | 1.69 m | | |
| | | 1.88 m | | |
| 3 | 86.8 d | 3.36 m | | 1' |
| 4 | 41.3 s | - | | |
| 5 | 140.8 s | - | | |
| 6 | 118.7 d | 5.52 m | | |
| 7 | 24.0 t | 1.87 m | | |
| | | 2.27 m | | |
| 8 | 44.3 d | 1.85 m | | |
| 9 | 49.9 s | - | | |
| 10 | 35.8 d | 2.34 m | | |
| 11 | 214.8 s | - | | |
| 12 | 48.6 t | 2.29 d | 13.5 Hz | |
| | | 3.01 d | | |
| 13 | 44.7 s | - | | |
| 14 | 34.9 s | - | | |
| 15 | 28.2 t | 1.24 m | | |
| | | 1.33 m | | |
| 16 | 28.6 t | 1.45 m | | |
| | | 2.04 m | | |
| 17 | 50.0 d | 1.69 m | | |
| 18 | 16.2 q | 0.66 s | (3H) | 12, 13, 14, 17 |
| 19 | 19.2 q | 0.96 s | (3H) | 8, 9, 10, 11 |
| 20 | 36.3 d | 1.32 m | | |
| 21 | 18.3 q | 0.84 d | 6.1 (3H) | 17, 20, 22 |
| 22 | 32.4 t | 1.30 m | | |
| | | 1.52 m | | |
| 23 | 33.1 t | 1.38 m | | |
| | | 1.45 m | | |
| 24 | 92.7 d | 3.31 m | | 1^{iv} |
| 25 | 72.9 s | - | | |
| 26 | 23.2 q | 1.05 s | (3H) | 24, 25, 27 |
| 27 | 25.8 q | 1.02 s | (3H) | 24, 25, 26 |
| 28 | 27.5 q | 0.97 s | (3H) | 3, 4, 5, 29 |
| 29 | 24.9 q | 1.13 s | (3H) | 3, 4, 5, 28 |
| 30 | 18.1 q | 1.02 s | (3H) | 8, 13, 14, 15 |

FIG. 35

| Position | δ$_C$ [ppm] | δ$_H$ [ppm] | J [Hz]/ (INT) | HMBC (H ->C) |
|---|---|---|---|---|
| Sugar moiety | | | | |
| *β*-D-Glucopyranoside | | | | |
| 1$^i$ | 105.5 d | 4.19 d | 8.4 | 3 |
| 2$^i$ | 74.2 d | 3.08 t | 8.4 | |
| 3$^i$ | 77.0 d | 3.19 t | 8.4 | |
| 4$^i$ | 70.6 d | 3.17 t | 8.4 | |
| 5$^i$ | 76.0 d | 3.31 m | | |
| 6$^i$ | 68.7 t | 3.69 m | | |
| | | 3.97 m | | |
| *α*-D-Glucopyranoside | | | | |
| 1$^{ii}$ | 98.9 d | 4.74 d | 3.4 | 4$^{ii}$ |
| 2$^{ii}$ | 73.0 d | 3.25 dd | 3.4, 8.4 | |
| 3$^{ii}$ | 77.3 d | 3.22 t | 8.4 | |
| 4$^{ii}$ | 70.4 d | 3.20 t | 8.4 | |
| 5$^{ii}$ | 75.4 d | 3.37 m | | |
| 6$^{ii}$ | 65.9 t | 3.63 m | | |
| | | 3.85 m | | |
| *β*-D-Glucopyranoside | | | | |
| 1$^{iii}$ | 104.1 d | 4.31 d | 8.4 | 6$^i$ |
| 2$^{iii}$ | 74.1 d | 3.10 t | 8.4 | |
| 3$^{iii}$ | 76.7 d | 3.25 t | 8.4 | |
| 4$^{iii}$ | 74.1 d | 3.53 t | 8.4 | |
| 5$^{iii}$ | 76.8 d | 3.30 m | | |
| 6$^{iii}$ | 61.3 t | 3.59 m | | |
| | | 3.70 m | | |
| *β*-D-Glucopyranoside | | | | |
| 1$^{iv}$ | 103.5 d | 4.34 d | 8.4 | 24 |
| 2$^{iv}$ | 79.7 d | 3.53 t | 8.4 | |
| 3$^{iv}$ | 77.8 d | 3.50 t | 8.4 | |
| 4$^{iv}$ | 70.2 d | 3.30 t | 8.4 | |
| 5$^{iv}$ | 75.5 d | 3.44 m | | |
| 6$^{iv}$ | 69.7 t | 3.45 m | | |
| | | 4.18 m | | |
| *β*-D-Glucopyranoside | | | | |
| 1$^v$ | 103.4 d | 4.70 d | 8.4 | 2$^{iv}$ |
| 2$^v$ | 74.2 d | 3.14 t | 8.4 | |
| 3$^v$ | 77.4 d | 3.25 t | 8.4 | |
| 4$^v$ | 71.0 d | 3.14 t | 8.4 | |
| 5$^v$ | 77.4 d | 3.27 m | | |
| 6$^v$ | 61.9 t | 3.54 m | | |
| | | 3.77 m | | |
| *β*-D-Glucopyranoside | | | | |
| 1$^{vi}$ | 104.1 d | 4.23 d | 8.4 | 6$^{iv}$ |
| 2$^{vi}$ | 73.6 d | 3.12 t | 8.4 | |
| 3$^{vi}$ | 77.6 d | 3.17 t | 8.4 | |
| 4$^{vi}$ | 71.2 d | 3.11 t | 8.4 | |
| 5$^{vi}$ | 76.7 d | 3.32 m | | |
| 6$^{vi}$ | 62.0 t | 3.54 m | | |
| | | 3.73 m | | |

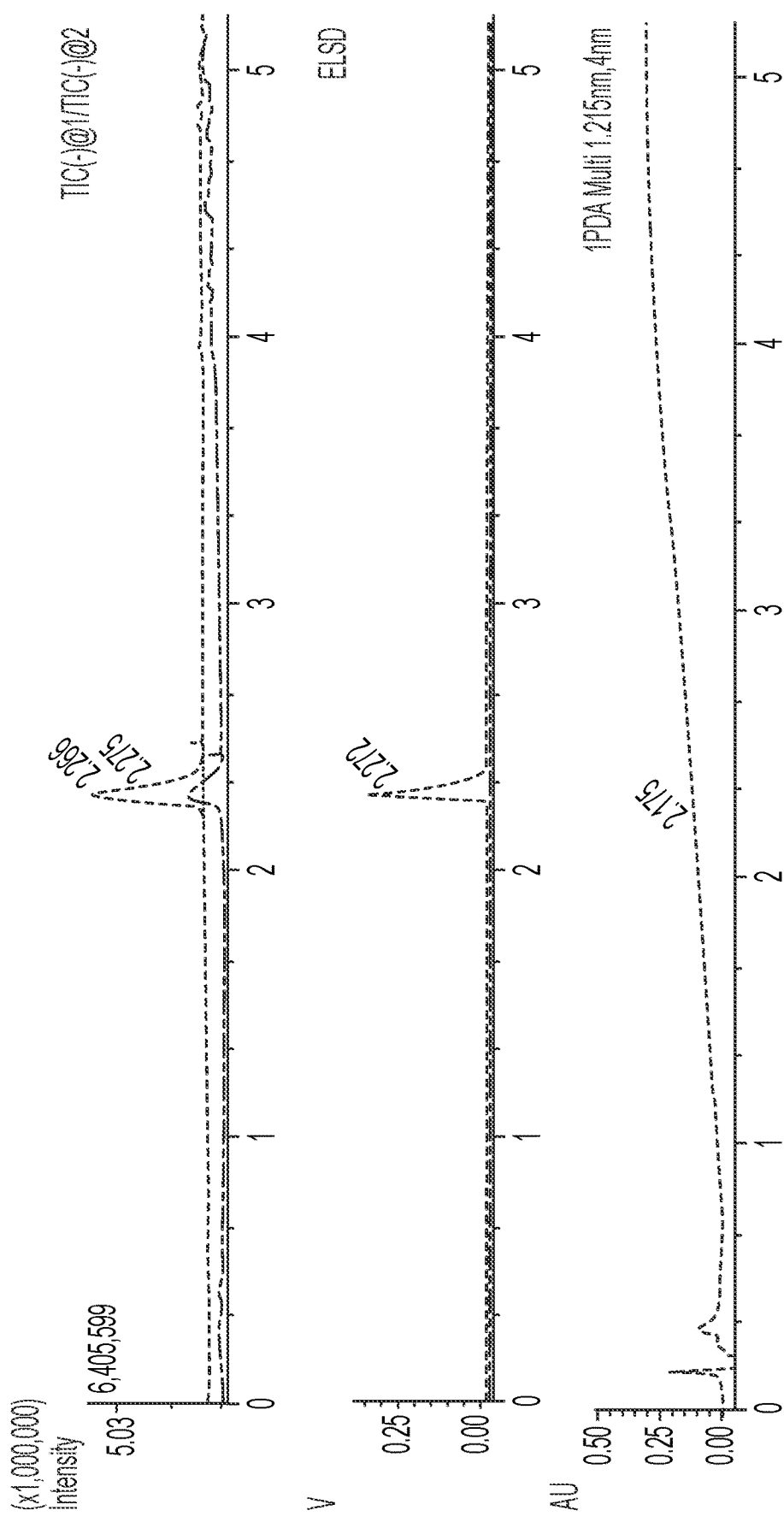

FROM FIG. 37A

FIG. 38

| Position | $\delta_C$ [ppm] | $\delta_H$ [ppm] | J [Hz]/ (INT) | HMBC (H ->C) |
|---|---|---|---|---|
| Aglycon moiety | | | | |
| 1 | 21.6 t | 1.14 m | | |
| | | 1.45 m | | |
| 2 | 27.8 t | 1.67 m | | |
| | | 1.85 m | | |
| 3 | 86.6 d | 3.39 m | | $1^I$ |
| 4 | 41.4 s | - | | |
| 5 | 140.7 s | - | | |
| 6 | 118.8 d | 5.51 m | | |
| 7 | 23.7 t | 1.85 m | | |
| | | 2.32 m | | |
| 8 | 44.2 d | 1.85 m | | |
| 9 | 35.0 s | - | | |
| 10 | 35.0 d | 2.35 m | | |
| 11 | 214.8 s | - | | |
| 12 | 48.7 t | 2.30 d | 13.6 | |
| | | 3.01 d | 13.6 | |
| 13 | 49.5 s | - | | |
| 14 | 49.3 s | - | | |
| 15 | 28.1 t | 1.23 m | | |
| | | 1.33 m | | |
| 16 | 28.5 t | 1.22 m | | |
| | | 2.04 m | | |
| 17 | 49.9 d | 1.66 m | | |
| 18 | 16.0 q | 0.66 s | (3H) | 12, 13, 14, 17 |
| 19 | 19.4 q | 1.00 s | (3H) | 8, 9, 10, 11 |
| 20 | 36.1 d | 1.31 m | | |
| 21 | 18.1 q | 0.84 d | 6.4 (3H) | 17, 20, 22 |
| 22 | 33.1 t | 1.29 m | | |
| | | 1.48 m | | |
| 23 | 33.0 t | 1.40 m | | |
| | | 1.45 m | | |
| 24 | 92.2 d | 3.30 m | | $1^{iv}$ |
| 25 | 72.9 s | - | | |
| 26 | 23.0 q | 1.05 s | (3H) | 24, 25, 27 |
| 27 | 25.9 q | 1.02 s | (3H) | 24, 25, 26 |
| 28 | 27.7 q | 0.96 s | (3H) | 3, 4, 5, 29 |
| 29 | 25.2 q | 1.16 s | (3H) | 3, 4, 5, 28 |
| 30 | 18.4 q | 1.02 s | (3H) | 8, 13, 14, 15 |

FIG. 39

| Position | $\delta_C$ [ppm] | $\delta_H$ [ppm] | J [Hz]/ (INT) | HMBC (H ->C) |
|---|---|---|---|---|
| Sugar moiety | | | | |
| *β*-D-Glucopyranoside | | | | |
| $1^i$ | 103.7 d | 4.31 d | 8.4 | 3 |
| $2^i$ | 79.5 d | 3.51 t | 8.4 | |
| $3^i$ | 77.8 d | 3.48 t | 8.4 | |
| $4^i$ | 70.7 d | 3.23 t | 8.4 | |
| $5^i$ | 76.1 d | 3.34 m | | |
| $6^i$ | 68.9 t | 3.68 m | | |
| | | 3.97 m | | |
| *β*-D-Glucopyranoside | | | | |
| $1^{ii}$ | 103.2 d | 4.53 d | 8.4 | $2^i$ |
| $2^{ii}$ | 75.2 d | 3.14 t | 8.4 | |
| $3^{ii}$ | 77.0 d | 3.25 t | 8.4 | |
| $4^{ii}$ | 70.7 d | 3.18 t | 8.4 | |
| $5^{ii}$ | 76.8 d | 3.10 m | | |
| $6^{ii}$ | 62.6 t | 3.56 m | | |
| | | 3.78 m | | |
| *β*-D-Glucopyranoside | | | | |
| $1^{iii}$ | 104.3 d | 4.31 d | 8.4 | $6^i$ |
| $2^{iii}$ | 75.0 d | 3.07 t | 8.4 | |
| $3^{iii}$ | 77.0 d | 3.25 t | 8.4 | |
| $4^{iii}$ | 70.8 d | 3.15 t | 8.4 | |
| $5^{iii}$ | 77.0 d | 3.14 m | | |
| $6^{iii}$ | 62.0 t | 3.56 m | | |
| | | 3.77 m | | |
| *β*-D-Glucopyranoside | | | | |
| $1^{iv}$ | 103.4 d | 4.34 d | 8.4 | 24 |
| $2^{iv}$ | 80.0 d | 3.54 t | 8.4 | |
| $3^{iv}$ | 77.6 d | 3.52 t | 8.4 | |
| $4^{iv}$ | 70.7 d | 3.23 t | 8.4 | |
| $5^{iv}$ | 76.7 d | 3.40 m | | |
| $6^{iv}$ | 69.1 t | 3.53 m | | |
| | | 4.14 m | | |
| *β*-D-Glucopyranoside | | | | |
| $1^v$ | 103.3 d | 4.71 d | 8.4 | $2^{iv}$ |
| $2^v$ | 73.6 d | 3.19 t | 8.4 | |
| $3^v$ | 76.9 d | 3.17 t | 8.4 | |
| $4^v$ | 70.8 d | 3.15 t | 8.4 | |
| $5^v$ | 76.8 d | 3.10 m | | |
| $6^v$ | 61.6 t | 3.58 m | | |
| | | 3.75 m | | |
| *β*-D-Glucopyranoside | | | | |
| $1^{vi}$ | 103.4 t | 4.19 d | 8.4 | $6^{iv}$ |
| $2^{vi}$ | 74.8 d | 3.10 t | 8.4 | |
| $3^{vi}$ | 77.0 d | 3.25 t | 8.4 | |
| $4^{vi}$ | 70.9 d | 3.11 t | 8.4 | |
| $5^{vi}$ | 77.0 d | 3.14 m | | |
| $6^{vi}$ | 62.2 t | 3.58 m | | |
| | | 3.74 m | | |

FROM FIG. 41A

FIG. 42

| Position | $\delta_C$ [ppm] | $\delta_H$ [ppm] | J [Hz]/ (INT) | HMBC (H ->C) |
|---|---|---|---|---|
| Aglycon moiety | | | | |
| 1 | 26.0 t | 1.37 m | | |
| | | 2.14 m | | |
| 2 | 28.7 t | 1.80 m | | |
| | | 1.84 m | | |
| 3 | 87.2 d | 3.35 m | | $1'$ |
| 4 | 41.7 s | | | |
| 5 | 143.8 s | - | | |
| 6 | 118.2 d | 5.39 m | | |
| 7 | 23.9 t | 1.70 m | | |
| | | 2.28 m | | |
| 8 | 43.8 d | 1.57 m | | |
| 9 | 39.4 s | - | | |
| 10 | 35.8 d | 2.41 m | | |
| 11 | 78.4 d | 3.73 m | | |
| 12 | 40.7 t | 1.71 m | | |
| | | 1.77 m | | |
| 13 | 47.6 s | - | | |
| 14 | 49.4 s | - | | |
| 15 | 33.8 t | 1.13 m | | |
| | | 1.42 m | | |
| 16 | 28.1 t | 1.22 m | | |
| | | 1.93 m | | |
| 17 | 51.0 d | 1.52 m | | |
| 18 | 15.6 q | 0.82 s | (3H) | 12, 13, 14, 17 |
| 19 | 25.3 q | 1.01 s | (3H) | 8, 9, 10, 11 |
| 20 | 36.5 d | 1.35 m | | |
| 21 | 18.4 q | 0.88 d | 6.1 (3H) | 17, 20, 22 |
| 22 | 30.0 t | 1.39 m | | |
| | | 1.44 m | | |
| 23 | 33.2 t | 1.38 m | | |
| | | 1.45 m | | |
| 24 | 92.1 d | 3.30 m | | $1^{iv}$ |
| 25 | 72.8 s | - | | |
| 26 | 22.9 q | 1.05 s | (3H) | 24, 25, 27 |
| 27 | 26.0 q | 1.02 s | (3H) | 24, 25, 26 |
| 28 | 27.1 q | 0.99 s | (3H) | 3, 4, 5, 29 |
| 29 | 25.4 q | 1.09 s | (3H) | 3, 4, 5, 28 |
| 30 | 19.0 q | 0.79 s | (3H) | 8, 13, 14, 15 |

FIG. 43

| Position | δ_C [ppm] | δ_H [ppm] | J [Hz]/ (INT) | HMBC (H →C) |
|---|---|---|---|---|
| Sugar moiety | | | | |
| β-D-Glucopyranoside | | | | |
| 1$^{i}$ | 105.2 d | 4.19 d | 8.4 | 3 |
| 2$^{i}$ | 74.2 d | 3.10 t | 8.4 | |
| 3$^{i}$ | 77.1 d | 3.20 t | 8.4 | |
| 4$^{i}$ | 74.8 d | 3.16 t | 8.4 | |
| 5$^{i}$ | 76.2 d | 3.33 m | | |
| 6$^{i}$ | 69.3 t | 3.71 m | | |
| | | 3.96 m | | |
| α-D-Glucopyranoside | | | | |
| 1$^{ii}$ | 98.9 d | 4.75 d | 3.4 | 4$^{iii}$ |
| 2$^{ii}$ | 72.8 d | 3.27 dd | 3.4, 8.4 | |
| 3$^{ii}$ | 76.9 d | 3.23 t | 8.4 | |
| 4$^{ii}$ | 70.4 d | 3.19 t | 8.4 | |
| 5$^{ii}$ | 76.1 d | 3.35 m | | |
| 6$^{ii}$ | 65.8 t | 3.63 m | | |
| | | 3.86 m | | |
| β-D-Glucopyranoside | | | | |
| 1$^{iii}$ | 104.1 d | 4.33 d | 8.4 | 6$^{i}$ |
| 2$^{iii}$ | 74.1 d | 3.10 t | 8.4 | |
| 3$^{iii}$ | 77.0 d | 3.26 t | 8.4 | |
| 4$^{iii}$ | 74.3 d | 3.54 t | 8.4 | |
| 5$^{iii}$ | 76.7 d | 3.29 m | | |
| 6$^{iii}$ | 62.2 t | 3.59 m | | |
| | | 3.71 m | | |
| β-D-Glucopyranoside | | | | |
| 1$^{iv}$ | 103.4 d | 4.34 d | 8.4 | 24 |
| 2$^{iv}$ | 80.5 d | 3.53 t | 8.4 | |
| 3$^{iv}$ | 77.8 d | 3.49 t | 8.4 | |
| 4$^{iv}$ | 70.6 d | 3.29 t | 8.4 | |
| 5$^{iv}$ | 75.6 d | 3.43 m | | |
| 6$^{iv}$ | 69.8 t | 3.53 m | | |
| | | 4.19 m | | |
| β-D-Glucopyranoside | | | | |
| 1$^{v}$ | 103.5 d | 4.68 d | 8.4 | 2$^{iv}$ |
| 2$^{v}$ | 73.9 d | 3.18 t | 8.4 | |
| 3$^{v}$ | 77.5 d | 3.23 t | 8.4 | |
| 4$^{v}$ | 70.7 d | 3.16 t | 8.4 | |
| 5$^{v}$ | 77.5 d | 3.25 m | | |
| 6$^{v}$ | 61.7 t | 3.56 m | | |
| | | 3.79 m | | |
| β-D-Glucopyranoside | | | | |
| 1$^{vi}$ | 104.2 d | 4.24 d | 8.4 | 6$^{iv}$ |
| 2$^{vi}$ | 73.7 d | 3.11 t | 8.4 | |
| 3$^{vi}$ | 77.5 d | 3.20 t | 8.4 | |
| 4$^{vi}$ | 71.1 d | 3.11 t | 8.4 | |
| 5$^{vi}$ | 76.6 d | 3.33 m | | |
| 6$^{vi}$ | 61.9 t | 3.56 m | | |
| | | 3.74 m | | |

FROM FIG. 45A

FIG. 46

| Position | δ$_C$ [ppm] | δ$_H$ [ppm] | J [Hz]/ (INT) | HMBC (H ->C) |
|---|---|---|---|---|
| Aglycon moiety | | | | |
| 1 | 26.0 t | 1.37 m | | |
|   |        | 2.14 m | | |
| 2 | 28.7 t | 1.80 m | | |
|   |        | 1.84 m | | |
| 3 | 87.2 d | 3.38 m | | 1$^I$ |
| 4 | 41.7 s | - | | |
| 5 | 143.8 s | - | | |
| 6 | 118.5 d | 5.40 m | | |
| 7 | 23.9 t | 1.70 m | | |
|   |        | 2.29 m | | |
| 8 | 43.2 d | 1.57 m | | |
| 9 | 39.4 s | - | | |
| 10 | 36.0 d | 2.43 m | | |
| 11 | 78.4 d | 3.76 m | | |
| 12 | 40.7 t | 1.71 m | | |
|    |        | 1.77 m | | |
| 13 | 47.6 s | - | | |
| 14 | 49.4 s | - | | |
| 15 | 33.8 t | 1.13 m | | |
|    |        | 1.42 m | | |
| 16 | 28.1 t | 1.22 m | | |
|    |        | 1.93 m | | |
| 17 | 50.7 d | 1.53 m | | |
| 18 | 15.6 q | 0.82 s | (3H) | 12, 13, 14, 17 |
| 19 | 25.3 q | 1.01 s | (3H) | 8, 9, 10 11 |
| 20 | 36.3 d | 1.37 m | | |
| 21 | 18.4 q | 0.88 d | 6.1 (3H) | 17, 20, 22 |
| 22 | 30.0 t | 1.39 m | | |
|    |        | 1.44 m | | |
| 23 | 33.2 t | 1.38 m | | |
|    |        | 1.45 m | | |
| 24 | 92.2 d | 3.30 m | | 1$^{iv}$ |
| 25 | 72.8 s | - | | |
| 26 | 22.9 q | 1.05 s | (3H) | 24, 25, 27 |
| 27 | 26.0 q | 1.02 s | (3H) | 24, 25, 26 |
| 28 | 27.1 q | 0.99 s | (3H) | 3, 4, 5, 29 |
| 29 | 25.4 q | 1.09 s | (3H) | 3, 4, 5, 28 |
| 30 | 19.0 q | 0.79 s | (3H) | 8, 13, 14, 15 |

FIG. 47

| Position | $\delta_C$ [ppm] | $\delta_H$ [ppm] | J [Hz]/ (INT) | HMBC (H →C) |
|---|---|---|---|---|
| Sugar moiety | | | | |
| β-D-Glucopyranoside | | | | |
| $1^i$ | 103.5 d | 4.19 d | 8.4 | 3 |
| $2^i$ | 74.2 d | 3.11 t | 8.4 | |
| $3^i$ | 77.1 d | 3.27 t | 8.4 | |
| $4^i$ | 74.9 d | 3.55 t | 8.4 | |
| $5^i$ | 76.4 d | 3.33 m | | |
| $6^i$ | 68.9 t | 3.75 m | | |
| | | 3.97 m | | |
| β-D-Glucopyranoside | | | | |
| $1^{ii}$ | 103.5 d | 4.23 d | 8.4 | $4^i$ |
| $2^{ii}$ | 75.2 d | 3.14 t | 8.4 | |
| $3^{ii}$ | 77.0 d | 3.25 t | 8.4 | |
| $4^{ii}$ | 70.7 d | 3.18 t | 8.4 | |
| $5^{ii}$ | 76.8 d | 3.10 m | | |
| $6^{ii}$ | 62.0 t | 3.70 m | | |
| | | 3.82 m | | |
| β-D-Glucopyranoside | | | | |
| $1^{iii}$ | 103.3 d | 4.35 d | 8.4 | $6^i$ |
| $2^{iii}$ | 75.0 d | 3.07 t | 8.4 | |
| $3^{iii}$ | 77.0 d | 3.25 t | 8.4 | |
| $4^{iii}$ | 70.8 d | 3.15 t | 8.4 | |
| $5^{iii}$ | 77.0 d | 3.14 m | | |
| $6^{iii}$ | 61.6 t | 3.57 m | | |
| | | 3.77 m | | |
| β-D-Glucopyranoside | | | | |
| $1^{iv}$ | 103.3 d | 4.34 d | 8.4 | 24 |
| $2^{iv}$ | 80.5 d | 3.51 t | 8.4 | |
| $3^{iv}$ | 77.6 d | 3.52 t | 8.4 | |
| $4^{iv}$ | 70.7 d | 3.23 t | 8.4 | |
| $5^{iv}$ | 76.7 d | 3.40 m | | |
| $6^{iv}$ | 68.9 t | 3.54 m | | |
| | | 4.15 m | | |
| β-D-Glucopyranoside | | | | |
| $1^v$ | 103.4 d | 4.69 d | 8.4 | $2^{iv}$ |
| $2^v$ | 73.6 d | 3.19 t | 8.4 | |
| $3^v$ | 76.9 d | 3.17 t | 8.4 | |
| $4^v$ | 70.8 d | 3.15 t | 8.4 | |
| $5^v$ | 76.8 d | 3.10 m | | |
| $6^v$ | 61.6 t | 3.58 m | | |
| | | 3.77 m | | |
| β-D-Glucopyranoside | | | | |
| $1^{vi}$ | 105.3 d | 4.19 d | 8.4 | $6^{iv}$ |
| $2^{vi}$ | 74.8 d | 3.10 t | 8.4 | |
| $3^{vi}$ | 77.0 d | 3.25 t | 8.4 | |
| $4^{vi}$ | 70.9 d | 3.11 t | 8.4 | |
| $5^{vi}$ | 77.0 d | 3.14 m | | |
| $6^{vi}$ | 61.8 t | 3.58 m | | |
| | | 3.74 m | | |

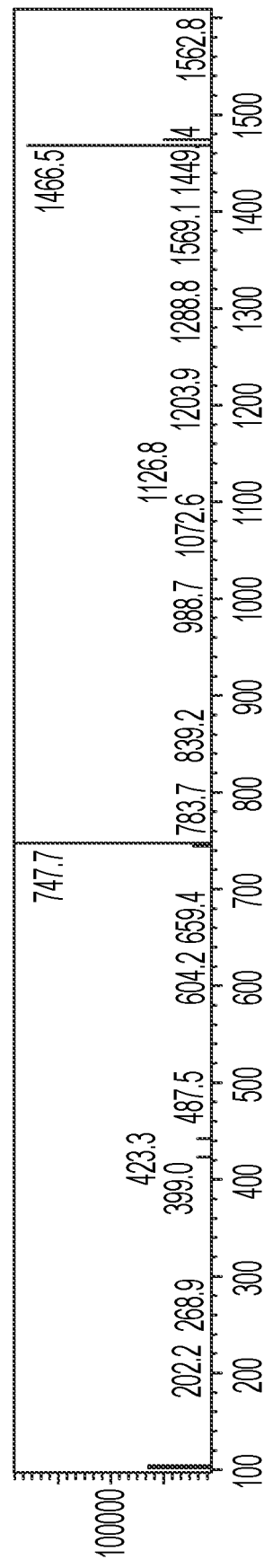
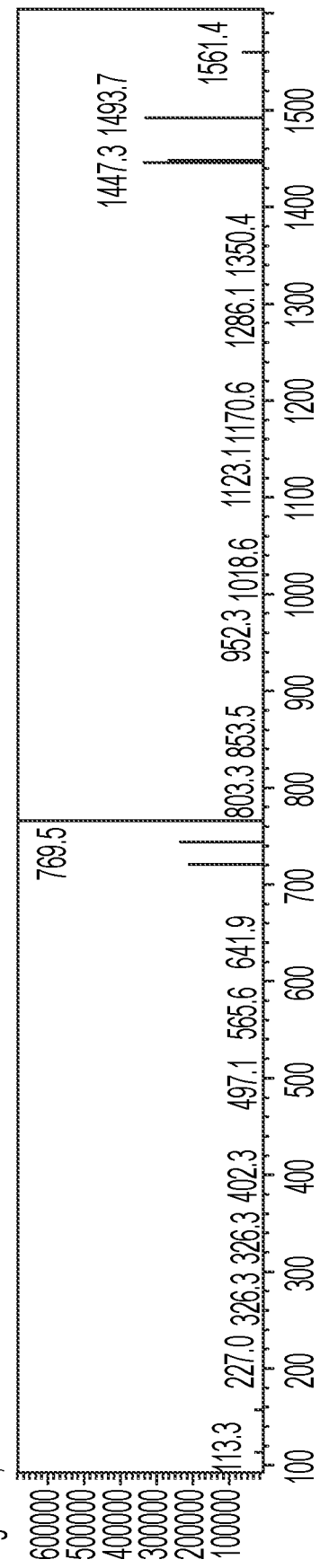
FROM FIG. 49A
FIG. 49B

FIG. 50

| Position | $\delta_C$ [ppm] | $\delta_H$ [ppm] | J [Hz]/ (INT) | HMBC (H ->C) |
|---|---|---|---|---|
| Aglycon moiety | | | | |
| 1 | 26.0 t | 1.37 m | | |
| | | 2.14 m | | |
| 2 | 28.7 t | 1.80 m | | |
| | | 1.84 m | | |
| 3 | 87.2 d | 3.35 m | | $1^I$ |
| 4 | 41.7 s | - | | |
| 5 | 143.8 s | - | | |
| 6 | 118.2 d | 5.39 m | | |
| 7 | 23.9 t | 1.70 m | | |
| | | 2.28 m | | |
| 8 | 43.8 d | 1.57 m | | |
| 9 | 39.4 s | - | | |
| 10 | 35.8 d | 2.41 m | | |
| 11 | 78.4 d | 3.73 m | | |
| 12 | 40.7 t | 1.71 m | | |
| | | 1.77 m | | |
| 13 | 47.6 s | - | | |
| 14 | 49.4 s | - | | |
| 15 | 33.8 t | 1.13 m | | |
| | | 1.42 m | | |
| 16 | 28.1 t | 1.22 m | | |
| | | 1.93 m | | |
| 17 | 51.0 d | 1.52 m | | |
| 18 | 15.6 q | 0.82 s | (3H) | 12, 13, 14, 17 |
| 19 | 25.3 q | 1.01 s | (3H) | 8, 9, 10, 11 |
| 20 | 36.5 d | 1.35 m | | |
| 21 | 18.4 q | 0.88 d | 6.1 (3H) | 17, 20, 22 |
| 22 | 30.0 t | 1.39 m | | |
| | | 1.44 m | | |
| 23 | 33.2 t | 1.38 m | | |
| | | 1.45 m | | |
| 24 | 92.1 d | 3.30 m | | $1^{IV}$ |
| 25 | 72.8 s | - | | |
| 26 | 22.9 q | 1.05 s | (3H) | 24, 25, 27 |
| 27 | 26.0 q | 1.02 s | (3H) | 24, 25, 26 |
| 28 | 27.1 q | 0.99 s | (3H) | 3, 4, 5, 29 |
| 29 | 25.4 q | 1.09 s | (3H) | 3, 4, 5, 28 |
| 30 | 19.0 q | 0.79 s | (3H) | 8, 13, 14, 15 |

FIG. 51

| Position | $\delta_C$ [ppm] | $\delta_H$ [ppm] | J [Hz]/ (INT) | HMBC (H ->C) |
|---|---|---|---|---|
| Sugar moiety | | | | |
| *β*-D-Glucopyranoside | | | | |
| $1^I$ | 103.6 d | 4.32 d | 8.4 | 3 |
| $2^I$ | 79.6 d | 3.51 t | 8.4 | |
| $3^I$ | 77.8 d | 3.49 t | 8.4 | |
| $4^I$ | 70.7 d | 3.23 t | 8.4 | |
| $5^I$ | 76.1 d | 3.34 m | | |
| $6^I$ | 68.9 t | 3.70 m | | |
| | | 3.97 m | | |
| *β*-D-Glucopyranoside | | | | |
| $1^{II}$ | 103.0 d | 4.56 d | 8.4 | $2^I$ |
| $2^{II}$ | 75.2 d | 3.14 t | 8.4 | |
| $3^{II}$ | 77.0 d | 3.25 t | 8.4 | |
| $4^{II}$ | 70.7 d | 3.18 t | 8.4 | |
| $5^{II}$ | 76.8 d | 3.10 m | | |
| $6^{II}$ | 61.8 t | 3.56 m | | |
| | | 3.78 m | | |
| *β*-D-Glucopyranoside | | | | |
| $1^{III}$ | 103.9 d | 4.32 d | 8.4 | $6^I$ |
| $2^{III}$ | 75.0 d | 3.07 t | 8.4 | |
| $3^{III}$ | 77.0 d | 3.25 t | 8.4 | |
| $4^{III}$ | 70.8 d | 3.15 t | 8.4 | |
| $5^{III}$ | 77.0 d | 3.14 m | | |
| $6^{III}$ | 61.8 t | 3.56 m | | |
| | | 3.77 m | | |
| *β*-D-Glucopyranoside | | | | |
| $1^{IV}$ | 103.5 d | 4.34 d | 8.4 | 24 |
| $2^{IV}$ | 79.7 d | 3.54 t | 8.4 | |
| $3^{IV}$ | 77.6 d | 3.52 t | 8.4 | |
| $4^{IV}$ | 70.7 d | 3.23 t | 8.4 | |
| $5^{IV}$ | 76.7 d | 3.40 m | | |
| $6^{IV}$ | 69.1 t | 3.52 m | | |
| | | 4.15 m | | |
| *β*-D-Glucopyranoside | | | | |
| $1^V$ | 103.4 d | 4.69 d | 8.4 | $2^{IV}$ |
| $2^V$ | 73.6 d | 3.19 t | 8.4 | |
| $3^V$ | 76.9 d | 3.17 t | 8.4 | |
| $4^V$ | 70.8 d | 3.15 t | 8.4 | |
| $5^V$ | 76.8 d | 3.10 m | | |
| $6^V$ | 61.6 t | 3.58 m | | |
| | | 3.75 m | | |
| *β*-D-Glucopyranoside | | | | |
| $1^{VI}$ | 103.3 d | 4.19 d | 8.4 | $6^{IV}$ |
| $2^{VI}$ | 74.8 d | 3.10 t | 8.4 | |
| $3^{VI}$ | 77.0 d | 3.25 t | 8.4 | |
| $4^{VI}$ | 70.9 d | 3.11 t | 8.4 | |
| $5^{VI}$ | 77.0 d | 3.14 m | | |
| $6^{VI}$ | 61.8 t | 3.58 m | | |
| | | 3.74 m | | |

| Position | $\delta_C$ [ppm] | $\delta_H$ [ppm] | J [Hz]/ (INT) | HMBC (H ->C) |
|---|---|---|---|---|
| Aglycon moiety | | | | |
| 1 | 21.8 t | 1.15 m | | |
|  |  | 1.48 m | | |
| 2 | 28.2 t | 1.70 m | | |
|  |  | 1.89 m | | |
| 3 | 86.6 d | 3.33 m | | $1^{I}$ |
| 4 | 41.2 s | - | | |
| 5 | 140.9 s | - | | |
| 6 | 118.7 d | 5.52 m | | |
| 7 | 23.7 t | 1.85 m | | |
|  |  | 2.28 m | | |
| 8 | 44.4 d | 1.86 m | | |
| 9 | 50.0 s | - | | |
| 10 | 35.4 d | 2.33 m | | |
| 11 | 214.9 d | - | | |
| 12 | 48.9 t | 2.30 m | | |
|  |  | 3.01 m | | |
| 13 | 44.6 s | - | | |
| 14 | 34.9 s | - | | |
| 15 | 28.5 t | 1.24 m | | |
|  |  | 1.35 m | | |
| 16 | 28.6 t | 1.46 m | | |
|  |  | 2.03 m | | |
| 17 | 50.1 d | 1.72 m | | |
| 18 | 16.3 q | 0.66 s | (3H) | 12, 13, 14, 17 |
| 19 | 19.0 q | 0.96 s | (3H) | 8, 9, 10, 11 |
| 20 | 36.4 d | 1.32 m | | |
| 21 | 18.1 q | 0.85 d | 6.1 (3H) | 17, 20, 22 |
| 22 | 32.8 t | 1.30 m | | |
|  |  | 1.54 m | | |
| 23 | 33.2 t | 1.38 m | | |
|  |  | 1.45 m | | |
| 24 | 92.5 d | 3.32 m | | $1^{IV}$ |
| 25 | 72.7 s | - | | |
| 26 | 23.0 q | 1.05 s | (3H) | 24, 25, 27 |
| 27 | 25.8 q | 1.02 s | (3H) | 24, 25, 26 |
| 28 | 27.4 q | 0.97 s | (3H) | 3, 4, 5, 29 |
| 29 | 24.9 q | 1.13 s | (3H) | 3, 4, 5, 28 |
| 30 | 18.0 q | 1.02 s | (3H) | 8, 13, 14, 15 |

FIG. 55

| Position | $\delta_C$ [ppm] | $\delta_H$ [ppm] | J [Hz]/ (INT) | HMBC (H ->C) |
|---|---|---|---|---|
| Sugar moiety | | | | |
| β-D-Glucopyranoside | | | | |
| $1^i$ | 103.2 d | 4.19 d | 8.4 | 3 |
| $2^i$ | 74.2 d | 3.11 t | 8.4 | |
| $3^i$ | 76.9 d | 3.25 t | 8.4 | |
| $4^i$ | 74.2 d | 3.56 t | 8.4 | |
| $5^i$ | 76.0 d | 3.36 m | | |
| $6^i$ | 69.2 t | 3.69 m | | |
| | | 3.97 m | | |
| α-D-Glucopyranoside | | | | |
| $1^{ii}$ | 99.0 d | 4.76 d | 3.4 | $4^i$ |
| $2^{ii}$ | 73.2 d | 3.27 dd | 3.4, 8.4 | |
| $3^{ii}$ | 76.5 d | 3.32 t | 8.4 | |
| $4^{ii}$ | 70.4 d | 3.27 t | 8.4 | |
| $5^{ii}$ | 75.3 d | 3.36 m | | |
| $6^{ii}$ | 65.8 t | 3.64 m | | |
| | | 3.87 m | | |
| β-D-Glucopyranoside | | | | |
| $1^{iii}$ | 104.2 d | 4.33 d | 8.4 | $6^i$ |
| $2^{iii}$ | 74.8 d | 3.12 t | 8.4 | |
| $3^{iii}$ | 77.4 d | 3.19 t | 8.4 | |
| $4^{iii}$ | 70.5 d | 3.17 t | 8.4 | |
| $5^{iii}$ | 77.5 d | 3.24 m | | |
| $6^{iii}$ | 61.4 t | 3.55 m | | |
| | | 3.75 m | | |
| β-D-Glucopyranoside | | | | |
| $1^{iv}$ | 103.5 d | 4.34 d | 8.4 | 24 |
| $2^{iv}$ | 79.6 d | 3.54 t | 8.4 | |
| $3^{iv}$ | 77.6 d | 3.50 t | 8.4 | |
| $4^{iv}$ | 70.3 d | 3.32 t | 8.4 | |
| $5^{iv}$ | 76.0 d | 3.34 m | | |
| $6^{iv}$ | 69.0 t | 3.52 m | | |
| | | 4.14 m | | |
| β-D-Glucopyranoside | | | | |
| $1^v$ | 103.3 d | 4.71 d | 8.4 | $2^{iv}$ |
| $2^v$ | 74.8 d | 3.18 t | 8.4 | |
| $3^v$ | 77.0 d | 3.27 t | 8.4 | |
| $4^v$ | 70.4 d | 3.23 t | 8.4 | |
| $5^v$ | 77.2 d | 3.22 m | | |
| $6^v$ | 61.2 d | 3.59 m | | |
| | | 3.71 m | | |
| β-D-Glucopyranoside | | | | |
| $1^{vi}$ | 105.4 d | 4.20 d | 8.4 | $6^{iv}$ |
| $2^{vi}$ | 74.6 d | 3.08 t | 8.4 | |
| $3^{vi}$ | 76.9 d | 3.17 t | 8.4 | |
| $4^{vi}$ | 70.8 d | 3.14 t | 8.4 | |
| $5^{vi}$ | 76.3 d | 3.23 m | | |
| $6^{vi}$ | 61.8 t | 3.55 m | | |
| | | 3.76 m | | |

FROM FIG. 57A

FIG. 58

| Position | δ_C [ppm] | δ_H [ppm] | J [Hz]/ (INT) | HMBC (H ->C) |
|---|---|---|---|---|
| Aglycon moiety | | | | |
| 1 | 25.9 t | 1.38 m | | |
| | | 2.13 m | | |
| 2 | 28.7 t | 1.80 m | | |
| | | 1.84 m | | |
| 3 | 87.3 d | 3.37 m | | $1^{I}$ |
| 4 | 41.8 s | - | | |
| 5 | 143.6 s | - | | |
| 6 | 118.4 d | 5.39 m | | |
| 7 | 23.9 t | 1.70 m | | |
| | | 2.28 m | | |
| 8 | 43.7 d | 1.57 m | | |
| 9 | 39.4 s | - | | |
| 10 | 35.8 d | 2.40 m | | |
| 11 | 78.4 d | 3.76 m | | |
| 12 | 40.6 t | 1.71 m | | |
| | | 1.77 m | | |
| 13 | 47.6 s | - | | |
| 14 | 49.1 s | - | | |
| 15 | 33.8 t | 1.12 m | | |
| | | 1.42 m | | |
| 16 | 28.1 t | 1.22 m | | |
| | | 1.93 m | | |
| 17 | 50.9 d | 1.52 m | | |
| 18 | 15.6 q | 0.82 s | (3H) | 12, 13, 14, 17 |
| 19 | 25.3 q | 1.01 s | (3H) | 8, 9, 10, 11 |
| 20 | 36.5 d | 1.35 m | | |
| 21 | 18.4 q | 0.88 d | 6.1 (3H) | 17, 20, 22 |
| 22 | 30.0 t | 1.39 m | | |
| | | 1.44 m | | |
| 23 | 33.2 t | 1.38 m | | |
| | | 1.45 m | | |
| 24 | 92.1 d | 3.30 m | | $1^{IV}$ |
| 25 | 72.8 s | - | | |
| 26 | 22.9 q | 1.05 s | (3H) | 24, 25, 27 |
| 27 | 26.0 q | 1.02 s | (3H) | 24, 25, 26 |
| 28 | 27.1 q | 0.99 s | (3H) | 3, 4, 5, 29 |
| 29 | 25.4 q | 1.09 s | (3H) | 3, 4, 5, 28 |
| 30 | 19.0 q | 0.79 s | (3H) | 8, 13, 14, 15 |

FIG. 59

| Position | $\delta_C$ [ppm] | $\delta_H$ [ppm] | J [Hz]/ (INT) | HMBC (H ->C) |
|---|---|---|---|---|
| Sugar moiety | | | | |
| β-D-Glucopyranoside | | | | |
| $1^i$ | 103.5 d | 4.19 d | 8.4 | 3 |
| $2^i$ | 74.2 d | 3.11 t | 8.4 | |
| $3^i$ | 77.1 d | 3.27 t | 8.4 | |
| $4^i$ | 74.8 d | 3.56 t | 8.4 | |
| $5^i$ | 76.4 d | 3.33 m | | |
| $6^i$ | 69.3 t | 3.71 m | | |
| | | 3.96 m | | |
| α-D-Glucopyranoside | | | | |
| $1^{ii}$ | 99.0 d | 4.76 d | 3.4 | $4^i$ |
| $2^{ii}$ | 72.8 d | 3.27 dd | 3.4, 8.4 | |
| $3^{ii}$ | 76.9 d | 3.31 t | 8.4 | |
| $4^{ii}$ | 70.4 d | 3.31 t | 8.4 | |
| $5^{ii}$ | 76.1 d | 3.35 m | | |
| $6^{ii}$ | 65.8 t | 3.63 m | | |
| | | 3.86 m | | |
| β-D-Glucopyranoside | | | | |
| $1^{iii}$ | 105.3 d | 4.20 d | 8.4 | $6^i$ |
| $2^{iii}$ | 74.1 d | 3.10 t | 8.4 | |
| $3^{iii}$ | 77.4 d | 3.29 t | 8.4 | |
| $4^{iii}$ | 70.7 d | 3.20 t | 8.4 | |
| $5^{iii}$ | 76.7 d | 3.22 m | | |
| $6^{iii}$ | 62.2 t | 3.56 m | | |
| | | 3.77 m | | |
| β-D-Glucopyranoside | | | | |
| $1^{iv}$ | 103.4 d | 4.34 d | 8.4 | 24 |
| $2^{iv}$ | 80.5 d | 3.53 t | 8.4 | |
| $3^{iv}$ | 77.8 d | 3.49 t | 8.4 | |
| $4^{iv}$ | 70.6 d | 3.23 t | 8.4 | |
| $5^{iv}$ | 76.6 d | 3.41 m | | |
| $6^{iv}$ | 68.9 t | 3.53 m | | |
| | | 4.15 m | | |
| β-D-Glucopyranoside | | | | |
| $1^v$ | 103.5 d | 4.68 d | 8.4 | $2^{iv}$ |
| $2^v$ | 73.9 d | 3.18 t | 8.4 | |
| $3^v$ | 77.5 d | 3.23 t | 8.4 | |
| $4^v$ | 70.7 d | 3.16 t | 8.4 | |
| $5^v$ | 77.5 d | 3.20 m | | |
| $6^v$ | 61.7 t | 3.62 m | | |
| | | 3.69 m | | |
| β-D-Glucopyranoside | | | | |
| $1^{vi}$ | 104.2 d | 4.35 d | 8.4 | $6^{iv}$ |
| $2^{vi}$ | 73.7 d | 3.11 t | 8.4 | |
| $3^{vi}$ | 76.5 d | 3.23 t | 8.4 | |
| $4^{vi}$ | 71.1 d | 3.11 t | 8.4 | |
| $5^{vi}$ | 76.6 d | 3.17 m | | |
| $6^{vi}$ | 61.9 t | 3.56 m | | |
| | | 3.74 m | | |

MOGROSIDES AND USE THEREOF

FIELD OF THE INVENTION

The invention relates to a process for purification of novel mogrosides from *Siraitia grosvenorii* fruit extract, and their applications in foods, beverage and other consumables.

DESCRIPTION OF THE RELATED ART

Luo han guo generally refers to a fruit of *Siraitia grosvenorii*, a member of the Cucurbitaceae family, which is a plant native to some regions of southern Asia and China. The sweet taste of luo han guo mainly comes from triterpene glycosides generally known as mogrosides or mogrol glycosides. Mogrosides comprise only about 1% of the luo han guo fruit. There are a number of mogrosides identified in luo han guo but generally mogroside V (CAS No: 88901-36-4) has the highest concentration compared to others (Table 1). Mogrol glycosides have the same core molecule—mogrol or oxo-mogrol and differ from each other by number and type of glycosidic residues bonded to mogrol or oxo-mogrol molecules.

TABLE 1

Mogrosides present in Luo han guo fruits

| Substance | Mol. Formula | Mol. Weight |
|---|---|---|
| Mogroside IIE | $C_{42}H_{72}O_{14}$ | 801.01 |
| Mogroside III | $C_{48}H_{82}O_{19}$ | 963.15 |
| Mogroside IV | $C_{54}H_{92}O_{24}$ | 1125.29 |
| Mogroside V | $C_{60}H_{102}O_{29}$ | 1287.43 |
| Mogroside VI | $C_{66}H_{112}O_{34}$ | 1449.58 |
| 11-oxo-Mogroside V | $C_{60}H_{100}O_{29}$ | 1285.42 |
| Siamenoside I | $C_{54}H_{92}O_{24}$ | 1125.29 |
| Grosmomoside I | $C_{54}H_{92}O_{24}$ | 1125.29 |

Various extraction techniques are used to isolate mogrosides from luo han guo fruits. As a result luo han guo powdered extracts are being prepared which usually contain 30-65% w/w of total mogrosides, and mogroside V content of those materials can vary as much as 18-55%. Such extracts generally cannot be widely used in foods and beverages as they possess undesirable organoleptic properties.

Hence there is a need for compositions comprising novel mogroside molecules with significantly improved organoleptic characteristics allowing their wider usage in foods, beverages and other consumables.

No techniques are currently available for purifying novel mogrosides. Therefore, there is a need for a process of for purification of novel high purity mogrosides from *Siraitia grosvenori* fruit extract.

BRIEF DESCRIPTION OF THE DRAWINGS

FIG. 30: NMR data of compound 8

FIG. 31: NMR data of compound 8 (continued)

FIG. 34: NMR data of compound 9

FIG. 35: NMR data of compound 9 (continued)

FIG. 38: NMR data of compound 10

FIG. 39: NMR data of compound 10 (continued)

FIG. 42: NMR data of compound 11

FIG. 43: NMR data of compound 11 (continued)

FIG. 46: NMR data of compound 12

FIG. 47: NMR data of compound 12 (continued)

FIG. 50: NMR data of compound 13

FIG. 51: NMR data of compound 13 (continued)

FIG. 54: NMR data of compound 14

FIG. 55: NMR data of compound 14 (continued)

FIG. 58: NMR data of compound 15
FIG. 59: NMR data of compound 15 (continued)

SUMMARY OF THE INVENTION

Figure 1:
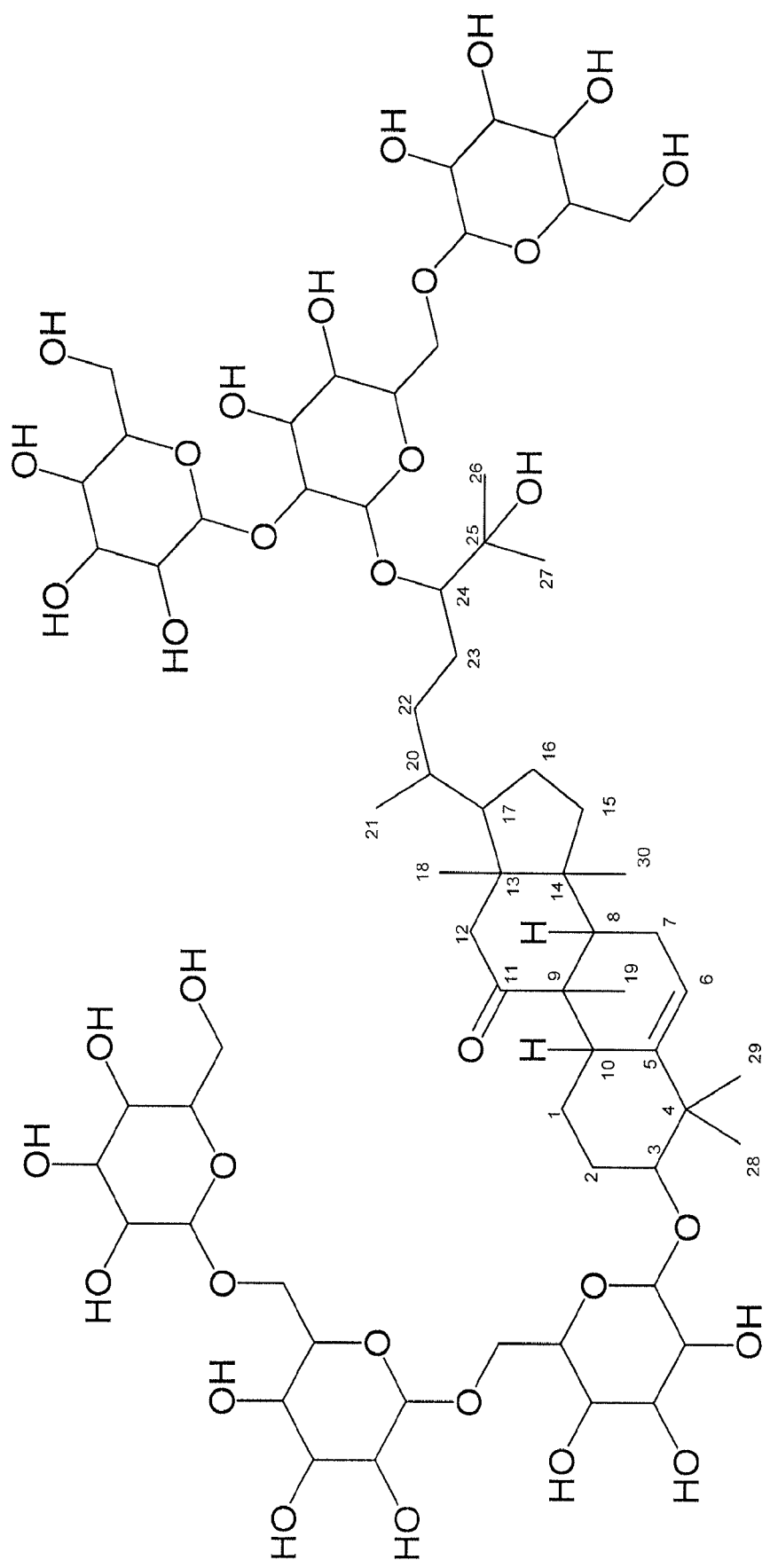
FIG. 1: Chemical structure of novel mogroside compound 1

The invention relates to a process for preparation of compositions comprising novel mogrosides from *Siraitia grosvenori* fruit extract.

In one embodiment, the process for purification of novel mogrosides comprises methods described in U.S. Patent Application No. 61/379,729 (filed Sep. 3, 2010), U.S. patent application Ser. No. 13/219,721 (filed Aug. 29, 2011), now patented as U.S. Pat. No. 9,101,162, and U.S. patent application Ser. No. 14/792,594 (filed Jul. 6, 2015), which was published as US Patent Application Publication No. 2015/0305381, which are incorporated by reference herein in their entirety.

In yet another embodiment the process further comprises:
a. providing a mixture of mogrosides;
b. dissolving the mogrosides mixture in solvent to form an initial solution of mogrosides;
c. passing the initial solution through a chromatographic system,
d. separating the fractions comprising novel mogroside compounds 1-15.

The present invention further provides compositions comprising novel mogroside compounds 1-15.

In one embodiment the compositions further comprise another high intensity sweetener selected from the group consisting of stevioside, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, dulcoside A, dulcoside B, rubusoside, other steviol glycosides occurring in *Stevia rebaudiana* plant, glycosylated steviol glycosides, biosynthetic steviol glycosides, Luo Han Guo sweetener, siamenoside, mogroside IV, mogroside V, mogroside VI, other mogrosides occurring in *Siraitia grosvenorii* fruits, monatin and its salts (monatin SS, RR, RS, SR), glycyrrhizic acid and its salts, curculin, thaumatin, monellin, mabinlin, brazzein, hemandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, and combinations thereof.

The present invention also provides consumables comprising novel mogroside compounds 1-15.

In one embodiment the consumable is selected from the group consisting of food, beverage, pharmaceutical composition, tobacco, nutraceutical, oral hygienic composition, or cosmetic.

DETAILED DESCRIPTION OF THE INVENTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention provides a process for purification of novel mogroside compounds 1-15 from *Siraitia grosvenorii* fruit.

Hereinafter the term "novel mogroside(s)" refers to compound(s) 1-15 (—FIG. 1-15 respectively).

The process of purification of novel mogrosides of the present invention comprises methods described in U.S. Patent Application No. 61/379,729 (filed Sep. 3, 2010), U.S. patent application Ser. No. 13/219,721 (filed Aug. 29, 2011), now patented as U.S. Pat. No. 9,101,162, and U.S. patent application Ser. No. 14/792,594 (filed Jul. 6, 2015), which was published as US Patent Application Publication No. 2015/0305381, which are incorporated by reference herein in their entirety.

The process of the present invention may further comprise isolation and purification of novel mogrosides using chromatography system.

In one embodiment of present invention a solution comprising at least one novel mogroside was passed through a HPLC column and fractions comprising novel mogrosides were collected. The HPLC column can be any suitable HPLC analytical or preparative scale column. The fractions may be eluted by adding an appropriate eluent. The eluent can be any suitable solvent or combination of solvents. In one embodiment, the eluent is water and/or acetonitrile. The method may optionally comprise additional steps, such as removal of solvents from the eluted solution to provide a concentrate comprising at least one novel mogroside.

In one embodiment, the following chromatography systems were used for isolation and purification of novel mogrosides. The mogrosides sample from a natural source was subjected to preparative HPLC using a commercial polyamine column, eluting with a mobile phase comprising acetonitrile and water. The mogrosides fraction from this step was further subjected to preparative HPLC using a commercial C18 column, eluting with a mobile phase comprising acetonitrile and water. Individual fractions from this step were further subjected to analytical-preparative HPLC using a commercial C18 column, eluting with a mobile phase comprising acetonitrile and water. The results of isolation and purification are summarized in Table 2. The purity of the isolated mogroside samples was suitable for NMR and HPLC-MS analysis.

TABLE 2

| Column | Loading Material | Fractions collected | Novel Mogroside compound(s) |
| --- | --- | --- | --- |
| Polyamine | Commercial Mogrosides extract | 1 combined fraction | Compounds 8-15 |
| Preparative C18 | Fraction from Polyamine column | Fraction 1 | Compounds 8 + 9 |
| | | Fraction 2 | Compounds 10 + 11 |
| | | Fraction 3 | Compound 12 |
| | | Fraction 4 | Compounds 13 + 14 |
| | | Fraction 5 | Compound 15 |
| Analytical Preparative C18 | Fraction 1 | Individual peak | Compound 8 |
| | | Individual peak | Compound 9 |
| | Fraction 2 | Individual peak | Compound 10 |
| | | Individual peak | Compound 11 |
| | Fraction 4 | Individual peak | Compound 13 |
| | | Individual peak | Compound 14 |

In one embodiment, the fractions comprising novel mogrosides were dried to produce compositions comprising at least one novel mogroside.

The compositions comprising at least one novel mogroside can be also produced from new cultivars of *Siraitia grosvenorii* plant which have increased content of novel mogrosides.

The compositions comprising at least one novel mogroside can be also produced by fermentation of recombinant microbial hosts selected from genera *Candida, Cyberlindnera, Kluyveromyces, Meyerozyma, Pischia., Rhodosporidium, Zygosaccharomyces, Saccharomyces, Aspergillus, Hansenula, Humicola, Trichosporon, Brettanomyces, Pachysolen, Yarrowia, Yamadazyma, Schizosaccharomyces, Ashbya, Cyberlindnera, Pichia, Arxula, Xanthophyllomyces* or *Escherichia*. Non-limiting examples of microbial strains include *Arthrobacter globiformis, Aspergillus niger, Aspergillus oryzae, Bacillus licheniformis, Bacillus sphaericus, Bacillus subtilis, Brevibacterium linens, Candida utilis, Candida vini, Corynebacterium glutamicum, Cyberlindnera jadinii, Cyberlindnera* sp., *Debaryomyces hansenii, Fusarium semitectum, Hypomyces armeniacus, Kluyveromyces lactis, Kluyveromyces marxianus, Kocuria rhizophila, Lactobacillus brevis, Lactobacillus casei, Lactobacillus pentoses, Lactobacillus plantarum, Lactobacillus reuteri, Meyerozyma guilliermondii, Microbacterium* sp., *Micrococcus luteus, Mucor hiemalis, Mucor racemosus, Penicillium roqueforti, Pichia guilliermondii, Pichia jadinii, Pichia pastoris, Pseudomonas fluorescens, Pseudomonas stutzeri, Rhodosporidium* sp., *Rhodosporidium toruloides, Rhodotorula mucilaginosa, Rhodotorula rubra, Rhodotorula* sp., *Saccharomyces bayanus, Saccharomyces cerevisiae, Saccharomyces pastorianus, Streptomyces albus, Streptomyces coelicolor, Streptomyces griseus, Streptomyces lividans, Torulaspora delbrueckii, Trichosporon laibachii, Trichosporon oleaginosus, Yarrowia lipolytica, Zygosaccharomyces rouxii, Zymomonas mobilis.*

The compositions comprising at least one novel mogroside can be also produced by biotransformation using suitable biocatalysts.

The compositions comprising at least one novel mogroside can be also produced by chemical synthesis from precursor compounds.

One embodiment of present invention is a composition comprising at least one novel mogroside.

In some embodiments, at least one novel mogroside imparts sweet taste.

In one embodiment, the present invention is a sweetener composition comprising at least one novel mogroside.

In another embodiment, the present invention is a flavor-enhancing composition comprising at least one novel mogroside, wherein the novel mogroside is present in an amount effective to provide a concentration at or below the threshold flavor recognition level of the novel mogroside when the flavor-enhancing composition is added to a consumable. In a particular embodiment, the novel mogroside is present in an amount effective to provide a concentration below the threshold flavor recognition level of the novel mogroside when the flavor-enhancing composition is added to a consumable. In one embodiment, the novel mogroside is present in an amount effective to provide a concentration at least about 1%, at least about 5%, at least about 10%, at least about 15,% at least about 20% or at least about 25% or more below the threshold flavor recognition level of the novel mogroside when the flavor-enhancing composition is added to a consumable.

In yet another embodiment, the present invention is a sweetness-enhancing composition comprising at least one novel mogroside, wherein the novel mogroside is present in an amount effective to provide a concentration at or below the threshold sweetness recognition level of the novel mogroside when the sweetness-enhancing composition is added to a consumable. In a particular embodiment, the novel mogroside is present in an amount effective to provide a concentration below the threshold sweetness recognition level of the novel mogroside when the sweetness-enhancing composition is added to a consumable. In one embodiment, the novel mogroside is present in an amount effective to provide a concentration at least about 1%, at least about 5%, at least about 10%, at least about 15,% at least about 20% or at least about 25% or more below the threshold sweetness recognition level of the novel mogroside when the sweetness-enhancing composition is added to a consumable.

In yet another embodiment, the present invention is a consumable comprising at least one novel mogroside. Suitable consumables include, but are not limited to, liquid-based or dry consumables, such as, for example, pharmaceutical compositions, edible gel mixes and compositions, dental compositions, foodstuffs, beverages and beverage products.

In a particular embodiment, the present invention is a beverage comprising a at least one novel mogroside. In a particular embodiment, the novel mogroside is present in the beverage at a concentration that is above, at or below the threshold sweetness recognition concentration of the novel mogroside.

In another particular embodiment, the present invention is a beverage product comprising a at least one novel mogroside. In a particular embodiment, the novel mogroside is present in the beverage product at a concentration that is above, at or below the threshold flavor recognition concentration of the novel mogroside.

In another aspect, the present invention is a method of preparing a consumable comprising (i) providing a consumable matrix and (ii) adding at least one novel mogroside to the consumable matrix to provide a consumable. In a particular embodiment, the novel mogroside is present in the consumable in a concentration above, at or below the threshold sweetness recognition of the novel mogroside. In another particular embodiment, the novel mogroside is present in the consumable in a concentration above, at or below the threshold flavor recognition of the novel mogroside.

In a particular embodiment, the present invention is a method of preparing a beverage comprising (i) providing a beverage matrix and (ii) adding at least one novel mogroside to the consumable matrix to provide a beverage. In a particular embodiment, the novel mogroside is present in the consumable in a concentration above, at or below the threshold sweetness recognition of the novel mogroside. In another particular embodiment, the novel mogroside is present in the consumable in a concentration above, at or below the threshold flavor recognition concentration of the novel mogroside.

In another aspect, the present invention is a method of enhancing the sweetness of a consumable comprising (i) providing a consumable comprising at least one sweet ingredient and (ii) adding at least one novel mogroside to the consumable to provide a consumable with enhanced sweetness, wherein the novel mogroside is present in the beverage with enhanced sweetness at a concentration at or below the threshold sweetness recognition concentration of the novel mogroside.

In a particular embodiment, the present invention is a method of enhancing the sweetness of a beverage comprising (i) providing a beverage comprising at least one sweet ingredient and (ii) adding at least one novel mogroside to the beverage to provide a beverage with enhanced sweetness, wherein the novel mogroside is present in the beverage with enhanced sweetness at a concentration below the threshold sweetness recognition concentration of the novel mogroside.

In one embodiment, the concentration of the novel mogroside is present in the beverage with enhanced sweetness at a concentration that is at least about 1%, at least about 5%, at least about 10%, at least about 15%, at least about 20%, or at least about 25% or more below the threshold sweetness recognition concentration of the novel mogroside.

In a further aspect, the present invention is a method of enhancing the flavor of a consumable comprising (i) providing a consumable comprising at least one flavor ingredient and (ii) adding at least one novel mogroside to the consumable to provide a consumable with enhanced flavor, wherein the novel mogroside in present in the consumable with enhanced flavor at a concentration at or below the threshold flavor recognition concentration of the novel mogroside.

In a particular embodiment, the present invention is a method of enhancing the flavor of a beverage comprising (i) providing a beverage comprising at least one flavor ingredient and (ii) adding at least one novel mogroside to the beverage to provide a beverage with enhanced flavor, wherein the novel mogroside is present in the beverage with enhanced flavor in a concentration at or below the threshold flavor recognition concentration of the novel mogroside. In one embodiment, the concentration of the novel mogroside is present in the beverage with enhanced sweetness at a concentration that is at least about 1%, at least about 5%, at least about 10%, at least about 15%, at least about 20%, or at least about 25% or more below the threshold flavor recognition concentration of the novel mogroside.

In the above methods, the novel mogroside may be added as such, or in the form of a composition comprising the novel mogroside. When the novel mogroside is provided as a composition, the concentration of the novel mogroside in the composition is effective to provide a concentration above, at or below the threshold flavor or sweetener composition of the novel mogroside, when the composition is added to the consumable, e.g., the food or beverage.

In some embodiments, the compositions of the present invention comprise one or more additional mogrosides, where the additional mogrosides are selected from, but not limited to, the group consisting of Luo han guo extract, by-products of other mogrosides' isolation and purification processes, a commercially available Luo han guo extract, mogroside IIE, mogroside IIB, mogroside III, mogroside IV, mogroside V, 11-oxo-mogroside V, mogroside VI, siamenoside I, grosmomoside I, neomogroside, and other mogrol and oxo-mogrol glycosides occurring in *Siraitia grosvenorii* fruit and combinations thereof.

In other embodiments, the compositions of the present invention comprise one or more sweeteners or additional sweeteners. In one embodiment, the additional sweetener is a natural sweetener or a synthetic sweetener. In a particular embodiment, the additional sweetener is a high intensity sweetener. In a particular embodiment, the additional sweetener is a mogroside.

In some embodiments, the compositions of the present invention comprise one or more additives. In a particular embodiment, the additive is selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

In some embodiments, the compositions of the present invention comprise one or more functional ingredients. In a particular embodiment, the functional ingredient is selected from the group consisting of caffeine, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In a particular embodiment, the present invention is a consumable comprising a novel mogroside and one or more additional mogrosides, sweeteners, additional sweeteners, additives or functional ingredients.

In another particular embodiment, the present invention is a beverage comprising at least one novel mogroside and one or more additional mogrosides, sweeteners, additional sweeteners, additives or functional ingredients.

The compositions comprising novel mogrosides can be used either alone or in combination with at least one other sweetener in consumables including food, beverage, pharmaceutical composition, tobacco, nutraceutical, oral hygienic composition, or cosmetic. The other sweeteners are selected from the group including sucrose, glyceraldehyde, dihydroxyacetone, erythrose, threose, erythrulose, arabinose, lyxose, ribose, xylose, ribulose, xylulose, allose, altrose, allulose, galactose, glucose, gulose, idose, mannose, talose, fructose, psicose, sorbose, tagatose, mannoheptulose, sedoheltulose, octolose, fucose, rhamnose, arabinose, turanose, sialose, inulin, inulooligosaccharides, fructooligosaccharides, high fructose corn syrup (HFCS), maltodextrin, coupling sugar, honey, stevia, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, dulcoside A, dulcoside B, rubusoside, steviolbioside, stevioside, other steviol glycosides occurring in *Stevia rebaudiana* plant, biosynthetic steviol glycosides, glycosylated steviol glycosides, glucosylated steviol glycosides (GSGs), mogroside IV, mogroside V, mogroside VI, Luo han guo, siamenoside, other mogrosides occurring in *Siraitia grosvenorii* fruits, monatin and its salts, curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, and cyclocarioside I, sugar alcohols, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, and combinations thereof.

The following examples are provided for illustrating the process and column system of the present invention.

Example 1

Purification of Novel Mogrosides

Luo Han Guo fruit extract, commercialized by PureCircle Sdn Bhd (Malaysia) containing 50.72% Mogroside V, 8.58% 11-oxo-Mogroside V, 5.67% Siamenoside I, 5.28% Grosmomoside I and about 3% of novel mogrosides was separated by a column system described in U.S. 61/379,729, U.S. Pat. No. 9,101,162 and U.S. Ser. No. 14/792,594 to obtain an enriched composition comprising about 20% of novel mogrosides, 31.1% Mogroside V, 2.8% 11-oxo-Mogroside V, 1.6% Siamenoside I, and 1.1% Grosmomoside I, all percentages being on w/w dried basis. The enriched composition was concentrated to approximately 50% solids content and subjected to preparative HPLC using YMC Polyamine II column (250×20 mm; 5 μm) at ambient temperature, eluting with a mobile phase consisting of acetonitrile and water with 75:25 (vol/vol) ratio (23 mL/min flowrate).

The mogrosides fraction from the preceding step was concentrated to about 7% solids content and was further subjected to preparative HPLC using Zorbax SB-C18 (9.4× 50 mm; 5 μm) column, eluting with a mobile phase consisting of acetonitrile and water with 14:86 vol/vol ratio (35 mL/min flowrate). Five fractions were collected (Table 2) and analysed by analytical-preparative HPLC for purity assessment. Fraction 1 contained two peaks corresponding to mogroside compounds 8 and 9, fraction 2 contained two peaks corresponding to mogroside compounds 10 and 11, fraction 3 contained one major peak corresponding to mogroside compound 12, fraction 4 contained at least two peaks corresponding to mogroside compound 13 and 14, and fraction 5 contained one major peak corresponding to mogroside compound 15. Fractions 1, 2 and 4 were further subjected to analytical-preparative separation described below, while fractions 3 and 5 were concentrated, dried and subjected to NMR and HPLCMS analyses.

Fractions 1, 2 and 4 from the preceding step were subjected to analytical-preparative HPLC, eluting with a mobile phase consisting of a mixture of acetonitrile and water with 19:81 (vol/vol) ratio for fraction 1 and 25:75 (vol/vol) ratio for fractions 2 and 4. The column was Poroshell 120 SB-C18 (4.6×150 mm; 2.7 μm), operated at 0.5 mL/min flowrate. The purified fractions containing individual peaks were concentrated, dried and subjected to NMR and HPLCMS analyses.

Example 2 NMR Analysis of the Novel Mogrosides

NMR samples were dissolved in methanol-d4 and analysed by 1D and 2D NMR methods. Noteworthy in the NMR analysis is the assignment of oxo- or hydroxy-functional group at C11—for oxo—a typical 13C chemical shift around 190-220 ppm was seen, whereas for hydroxy—a typical 13C chemical shift of around 65-85 ppm was seen. Also noteworthy is the assignment of alpha-glycosidic linkages for some mogroside compounds where a coupling constant of approximately 3.5 Hz is seen (for beta-glycosidic linkages the coupling constant is usually approximately 7-9 Hz). All novel mogroside compounds claimed in this application showed good purity required for structural elucidation. The acquired data was used for structure elucidation.

Example 3

HPLCMS Analysis of the Novel Mogrosides

HPLCMS were performed on Shimadzu MS 2020 on Cortecs UPLC C18 1.6 μm, 50×2.1 mm column, mobile phase A: 5 mM ammonium formate+0.1% formic acid, B:methanol:acetonitrile (1:1)+5 mM ammonium phosphate buffer+0.1% formic acid, injection volume 0.1-5 μl, detection ELSD (Sedex 85, pressure 4 bar, nebulizer temperature 35° C.), PDA 210-400 nm, gradient 5% B to 100% B in 4 min followed by 2 min 100% B, flowrate 1 ml/min, scan 100-1600 amu, pos/neg switch. All mogroside compounds claimed in this application showed good purity required for HPLCMS analysis.

Based on NMR data acquired in Example 2 and the data acquired during HPLCMS analysis of novel mogrosides, the structures of novel mogroside compounds 1-15 were proposed.

Example 4

Novel Mogrosides Organoleptic Characteristics

The organoleptic properties of the enriched composition comprising about 20% (w/w) novel mogrosides (Example 1), the individual novel mogroside compounds, obtained from individual peak fractions of Example 1, were assessed in aqueous solutions isosweet to 5% sucrose. The assessment was conducted by 20 panelists in comparison with 5% isosweet aqueous solutions of commercial Luo Han Guo fruit extract of Example 1, highly purified (96.6% pure) Mogroside V sample (sourced from ChromaDex Inc., USA) and sucrose (5%). The results are summarized in Table 3.

TABLE 3

Novel Mogrosides (NM) Taste Properties

| Compounds | Sweetness potency (sucrose = 1) | Sweetness Lingering* | Bitterness* | Delayed sweetness onset* | Licorice taste* | Overall taste profile vs. sugar |
|---|---|---|---|---|---|---|
| Enriched composition (20% NM) | 320 | 3 | 2 | 3 | 2 | pleasant |
| NM 8 | 320 | 1 | 1 | 2 | 1 | sugar-like |
| NM 9 | 300 | 2 | 1 | 2 | 1 | sugar-like |
| NM 10 | 320 | 1 | 2 | 2 | 1 | sugar-like |
| NM 11 | 310 | 1 | 2 | 2 | 1 | sugar-like |
| NM 12 | 350 | 1 | 1 | 2 | 1 | sugar-like |
| NM 13 | 310 | 2 | 1 | 3 | 1 | sugar-like |
| NM 14 | 300 | 1 | 1 | 1 | 1 | sugar-like |
| NM 15 | 340 | 1 | 1 | 1 | 1 | sugar-like |
| Luo Han Guo extract | 300 | 5 | 5 | 5 | 5 | unpleasant |
| Purified Mogroside V | 360 | 5 | 4 | 5 | 4 | tolerable |
| Sucrose | 1 | 1 | 1 | 1 | 1 | NA |

*For "Sweetness Lingering", "Bitterness", "Delayed sweetness onset", and "Licorice taste" characteristics the panelists score between 1 to 5, where the lower score represents more pleasant taste sensation by panelist The sensory evaluation results show all novel mogrosides possess significantly better taste profile compared to commercially available mogroside samples. The data for enriched composition (containing about 20% novel mogrosides) also shows that novel mogrosides can improve the overall taste characteristics of mogrosides mixtures comprising less pleasant mogrosides such as Mogroside V.

Example 5

Consumable Comprising Novel Mogrosides

Carbonated beverage samples were prepared according to formula presented in Table 4.

TABLE 4

Formula for carbonated beverages

| Ingredients | Quantity, % |
| --- | --- |
| Cola flavor | 0.340 |
| ortho-Phosphoric acid | 0.100 |
| Sodium citrate | 0.310 |
| Sodium benzoate | 0.018 |
| Citric acid | 0.018 |
| Mogroside composition | 0.050 |
| Carbonated water | to 100 |

The following samples were used as "mogroside composition" in the formula. The enriched composition of Example 1 (comprising about 20% (w/w) novel mogrosides), the individual novel mogroside compounds, obtained from individual peak fractions of Example 1, commercial Luo Han Guo fruit extract of Example 1, highly purified (96.6% pure) Mogroside V sample (from ChromaDex Inc., USA). The sensory assessment of beverage samples was conducted by 20 panelists. The results are summarized in Table 5.

TABLE 5

Sensory evaluation of carbonated beverage samples

| "Mogroside composition" used in formula | Sweetness Lingering* | Bitterness* | Delayed sweetness onset* | Licorice taste* | Overall taste |
| --- | --- | --- | --- | --- | --- |
| Enriched composition (20% NM) | 2 | 2 | 2 | 2 | pleasant |
| NM 8 | 1 | 1 | 2 | 1 | sugar-like |
| NM 9 | 2 | 1 | 1 | 1 | sugar-like |
| NM 10 | 1 | 2 | 2 | 1 | sugar-like |
| NM 11 | 2 | 1 | 1 | 1 | sugar-like |
| NM 12 | 1 | 1 | 2 | 1 | sugar-like |
| NM 13 | 1 | 2 | 2 | 1 | sugar-like |
| NM 14 | 1 | 1 | 1 | 2 | sugar-like |
| NM 15 | 2 | 1 | 1 | 1 | sugar-like |
| Luo Han Guo extract | 5 | 5 | 5 | 5 | unpleasant |
| Purified Mogroside V | 5 | 4 | 5 | 5 | tolerable |

*For "Sweetness Lingering", "Bitterness", "Delayed sweetness onset", and "Licorice taste" characteristics the panelists score between 1 to 5, where the lower score represents more pleasant taste sensation by panelist The results showed the beverages prepared using the composition comprising novel mogrosides possessed the best organoleptic characteristics.

Example 6

Consumable Comprising Novel Mogrosides

Chocolate samples were papered according to formula in Table 6.

TABLE 6

Formula for chocolate samples

| Ingredients | Quantity, % |
| --- | --- |
| Chocolate liquor | 30.0 |
| Cocoa butter | 11.5 |
| Milk powder | 14.0 |
| Sorbitol | 44.0 |
| Salt | 0.1 |
| Mogroside composition | 0.1 |
| Lecithin | 0.3 |

Chocolate liquor, cocoa butter, milk powder, sorbitol, salt, and the "mogroside composition" were kneaded sufficiently, and the mixture was then placed in a refiner to reduce its particle size for 24 hours. Thereafter, the content was transferred into a conche, the lecithin was added, and the composition was kneaded at 50° C. for 48 hours. Then, the content was placed in a shaping apparatus, and solidified.

The following samples were used as "mogroside composition" in the formula of Table 6. Enriched composition comprising about 20% (w/w) novel mogrosides (Example 1), the individual novel mogroside compounds, obtained from individual peak fractions of Example 1, commercial Luo Han Guo fruit extract of Example 1, highly purified (96.6% pure) Mogroside V sample sourced from ChromaDex Inc., (USA). The sensory assessment of chocolate samples was conducted by 20 panelists. The results are summarized in Table 7.

TABLE 7

Sensory evaluation of chocolate samples

| "Mogroside composition" used in formula | Sweetness Lingering* | Bitterness* | Licorice taste* | Overall taste |
| --- | --- | --- | --- | --- |
| Enriched composition (20% NM) | 2 | 2 | 2 | pleasant |
| NM 8 | 1 | 1 | 1 | sugar-like |
| NM 9 | 2 | 2 | 1 | sugar-like |
| NM 10 | 1 | 2 | 2 | sugar-like |
| NM 11 | 1 | 1 | 1 | sugar-like |
| NM 12 | 2 | 1 | 2 | sugar-like |
| NM 13 | 1 | 2 | 1 | sugar-like |
| NM 14 | 1 | 1 | 2 | sugar-like |
| NM 15 | 2 | 2 | 1 | sugar-like |
| Luo Han Guo extract | 5 | 5 | 5 | unpleasant |
| Purified Mogroside V | 4 | 5 | 5 | tolerable |

*For "Sweetness Lingering", "Bitterness", and "Licorice taste" characteristics the panelists score between 1 to 5, where the lower score represents more pleasant taste sensation by panelist The results showed the chocolate samples prepared using the composition comprising novel mogrosides possessed the best organoleptic characteristics.

While the present invention has been described with reference to particular embodiments, it will be understood that the embodiments are illustrative and that the invention scope is not so limited. Alternative embodiments of the present invention will become apparent to those having

Figure 2:
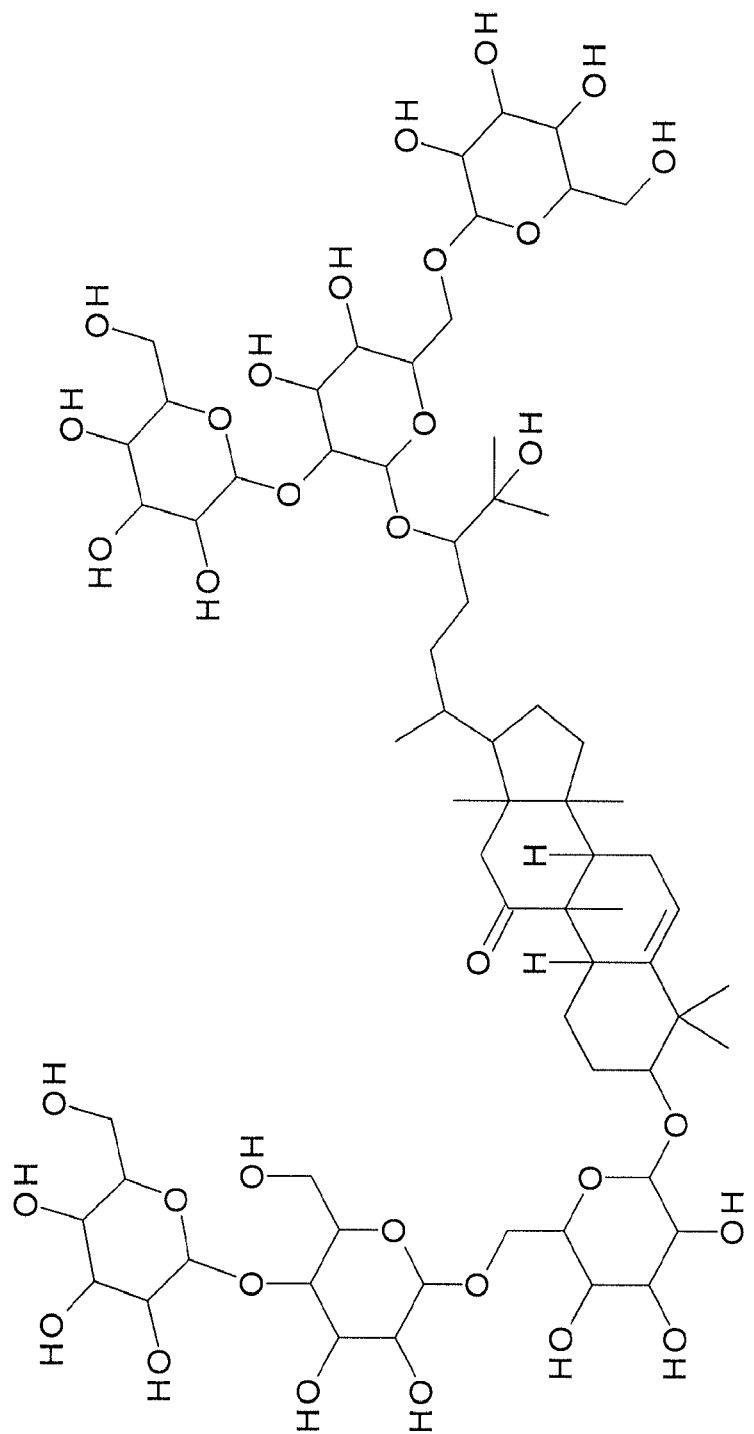
FIG. 2: Chemical structure of novel mogroside compound 2
Figure 3:
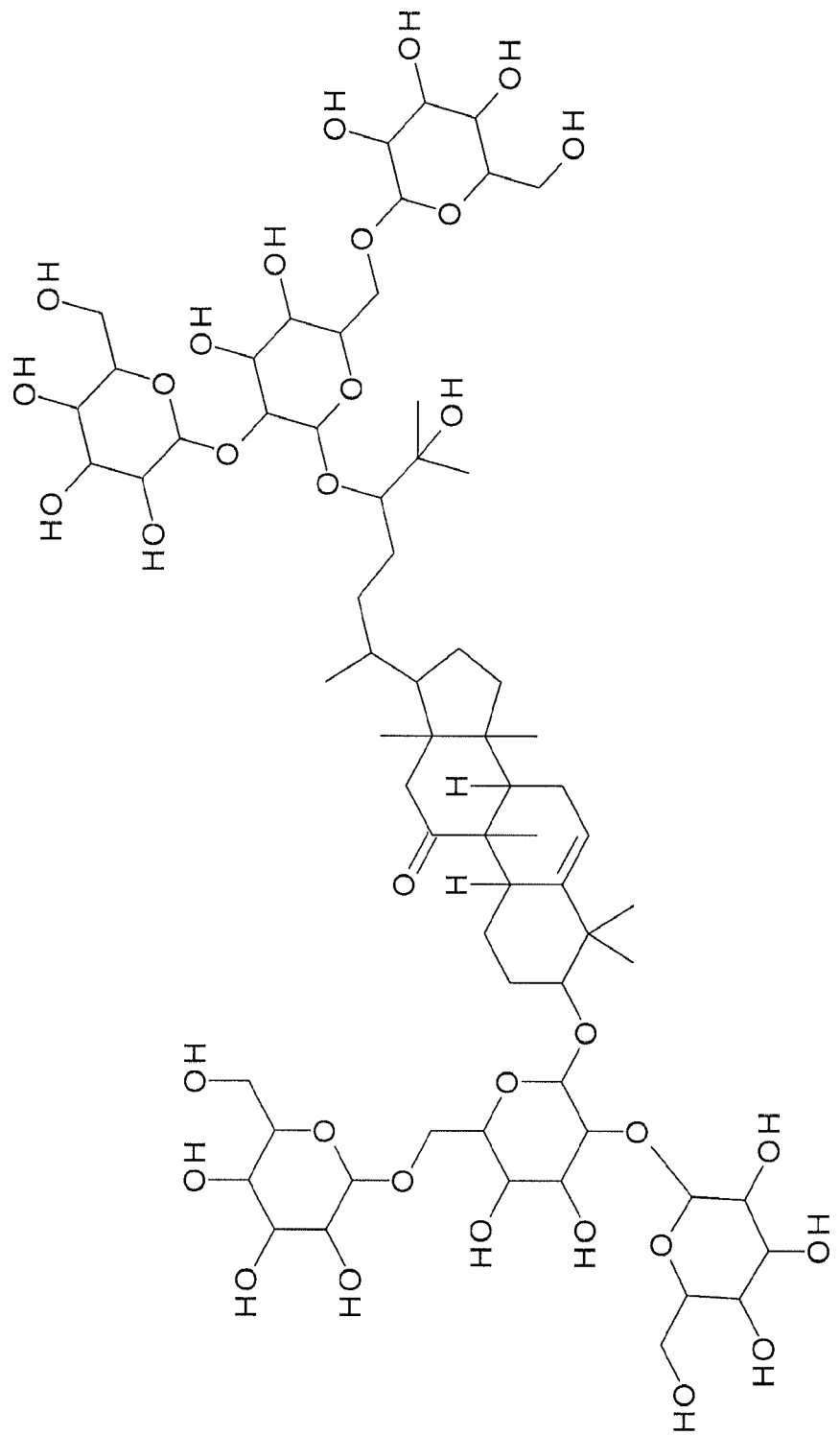
FIG. 3: Chemical structure of novel mogroside compound 3

We claim:
1. A composition comprising at least one isolated or purified mogroside compound having a chemical structure represented in any of formulae 1, 2, 4, 5, 7, 8, 9, 11, 12, 14 and 15:
Formula 1
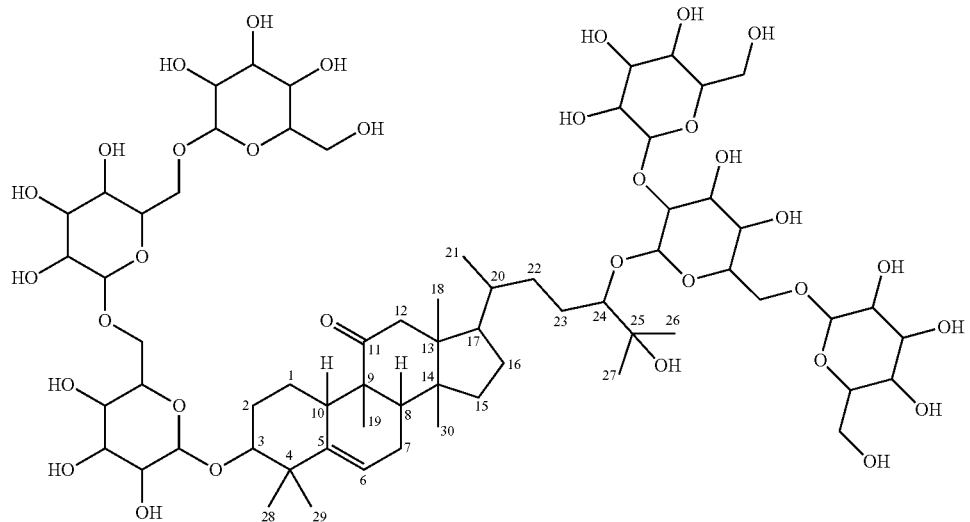
(FIG. 1)
Formula 2
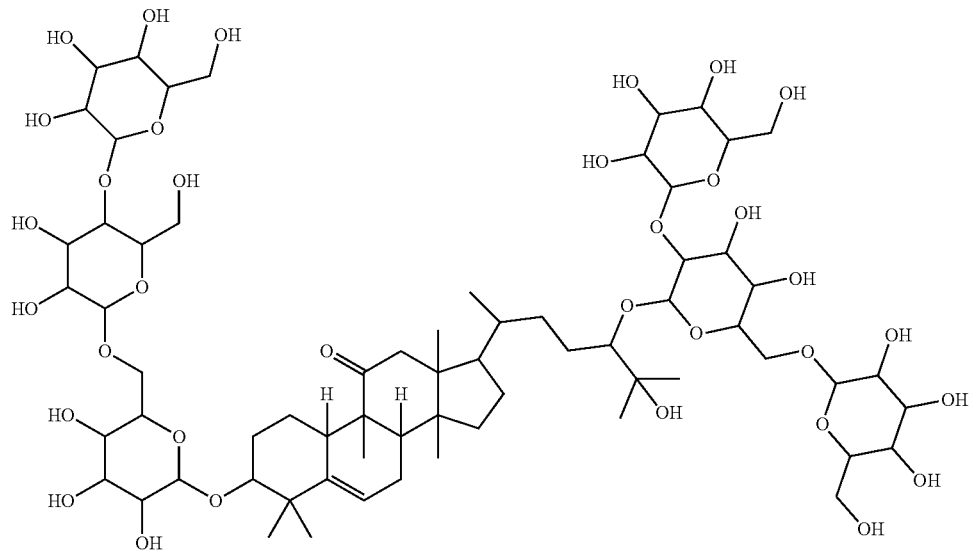
(FIG. 2)

Figure 4:
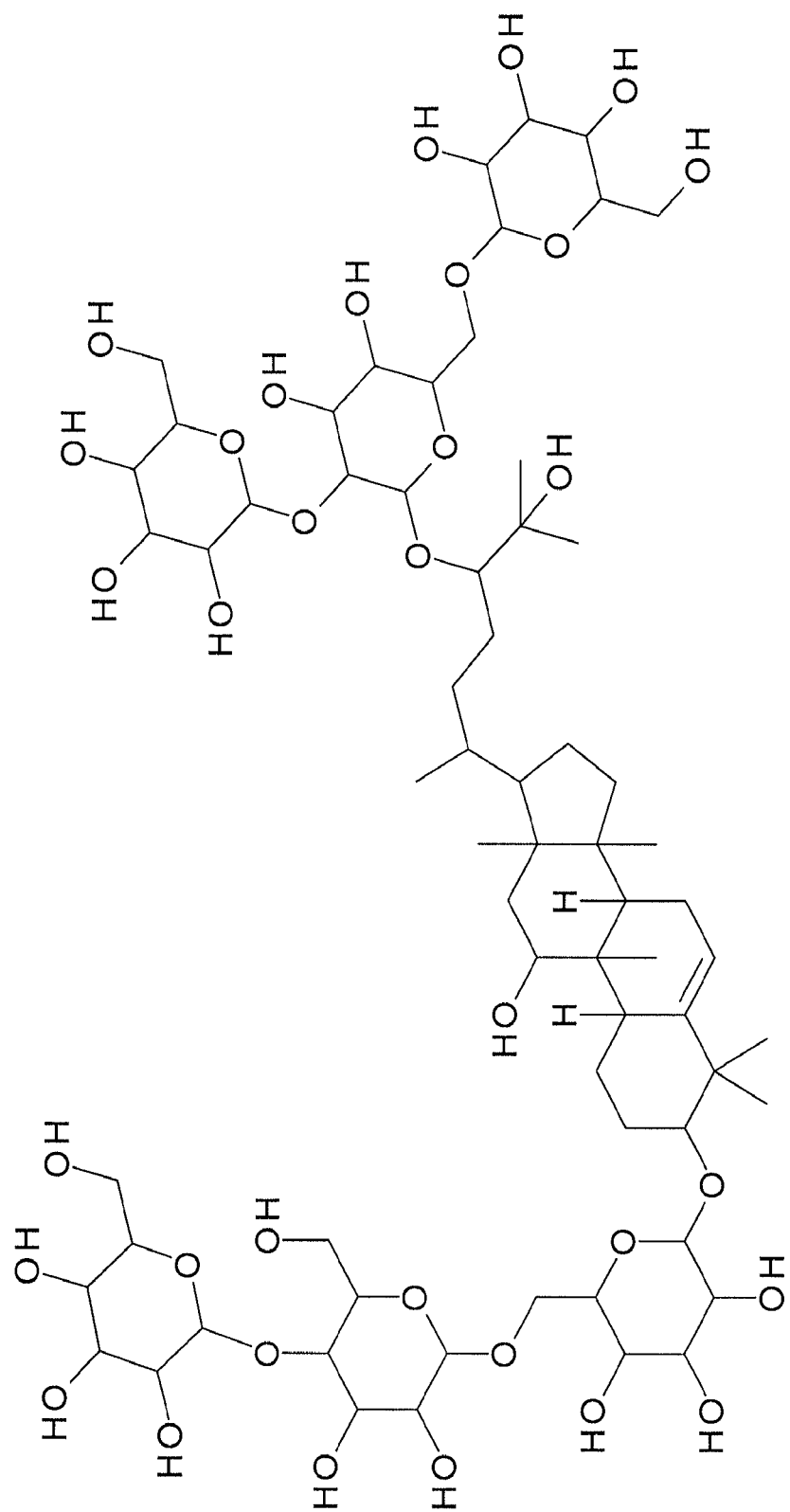
FIG. 4: Chemical structure of novel mogroside compound 4
Figure 5:
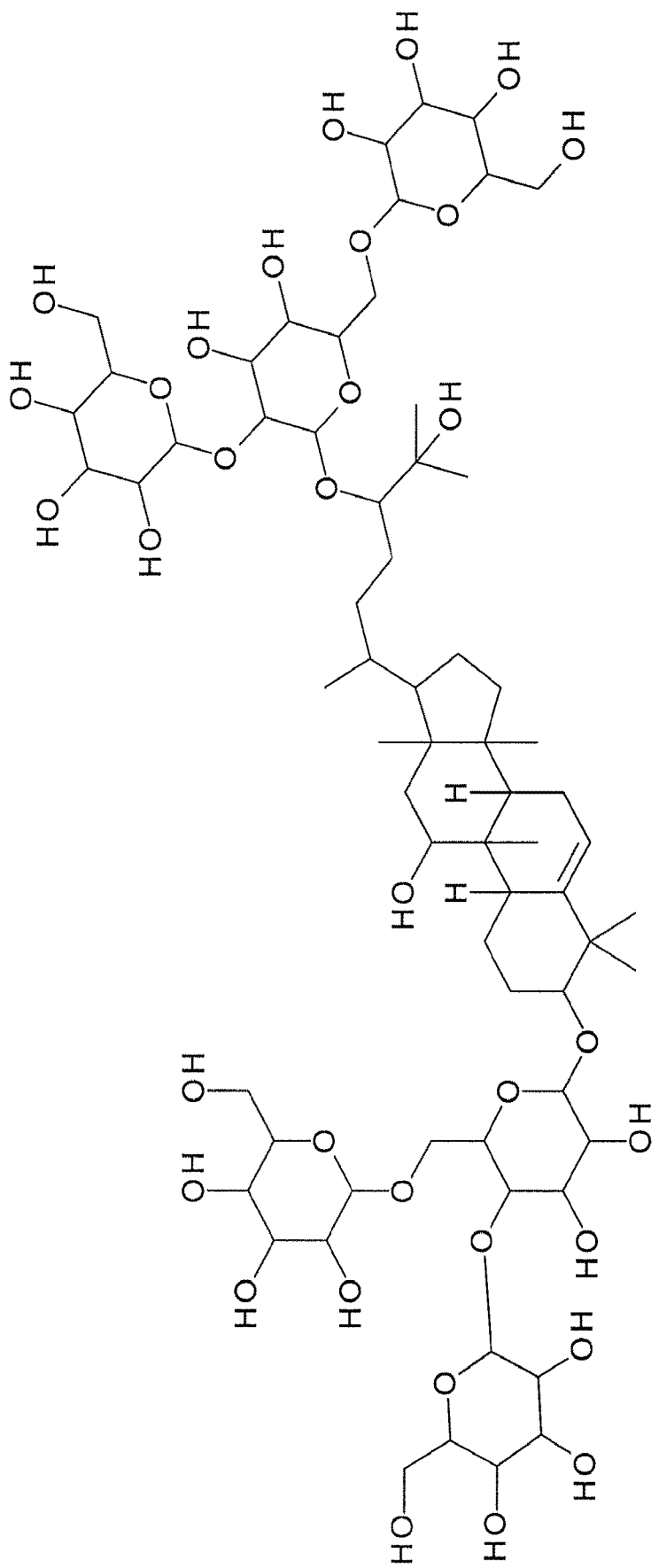
FIG. 5: Chemical structure of novel mogroside compound 5
Figure 6:
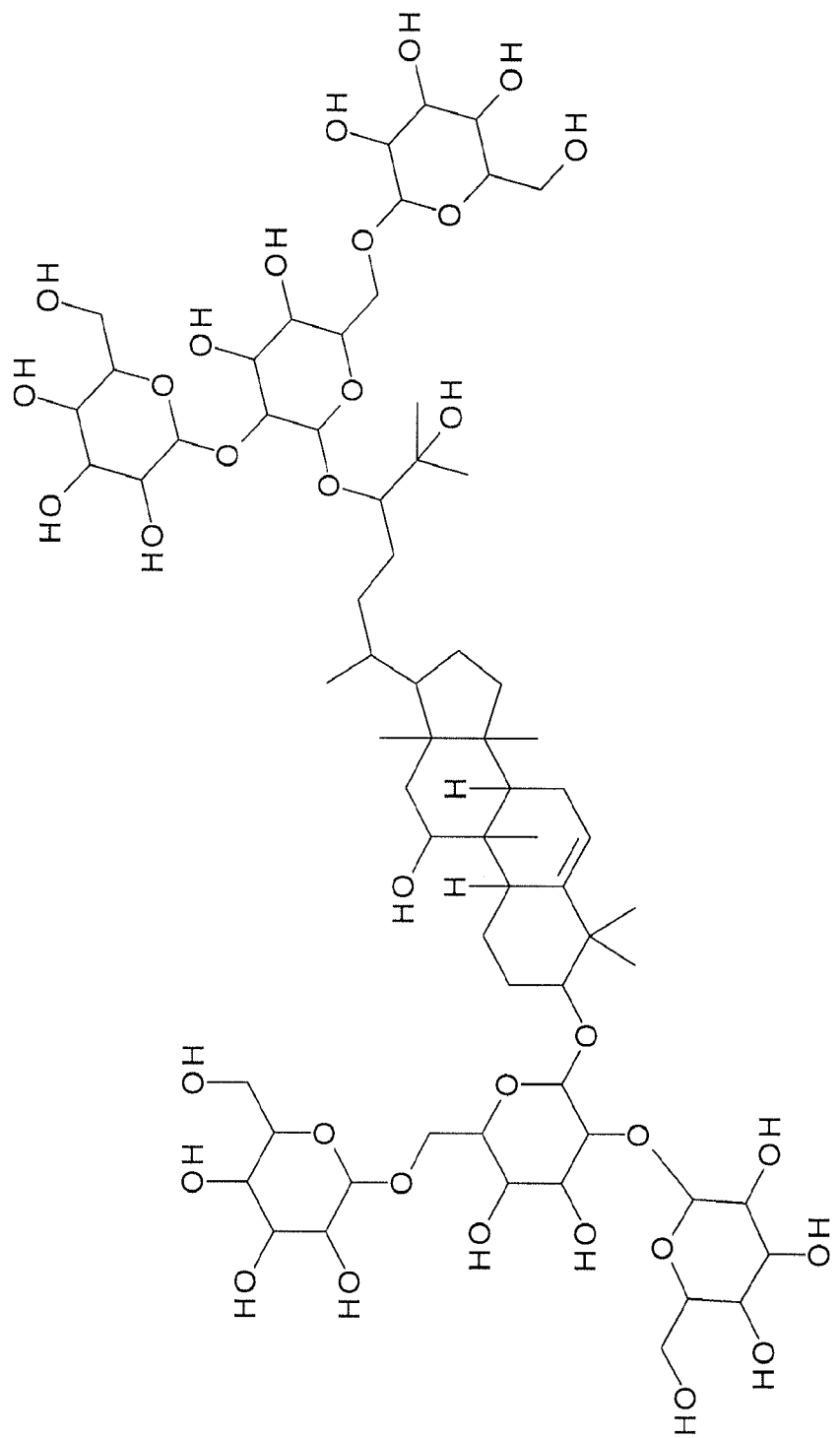
FIG. 6: Chemical structure of novel mogroside compound 6
Figure 7:
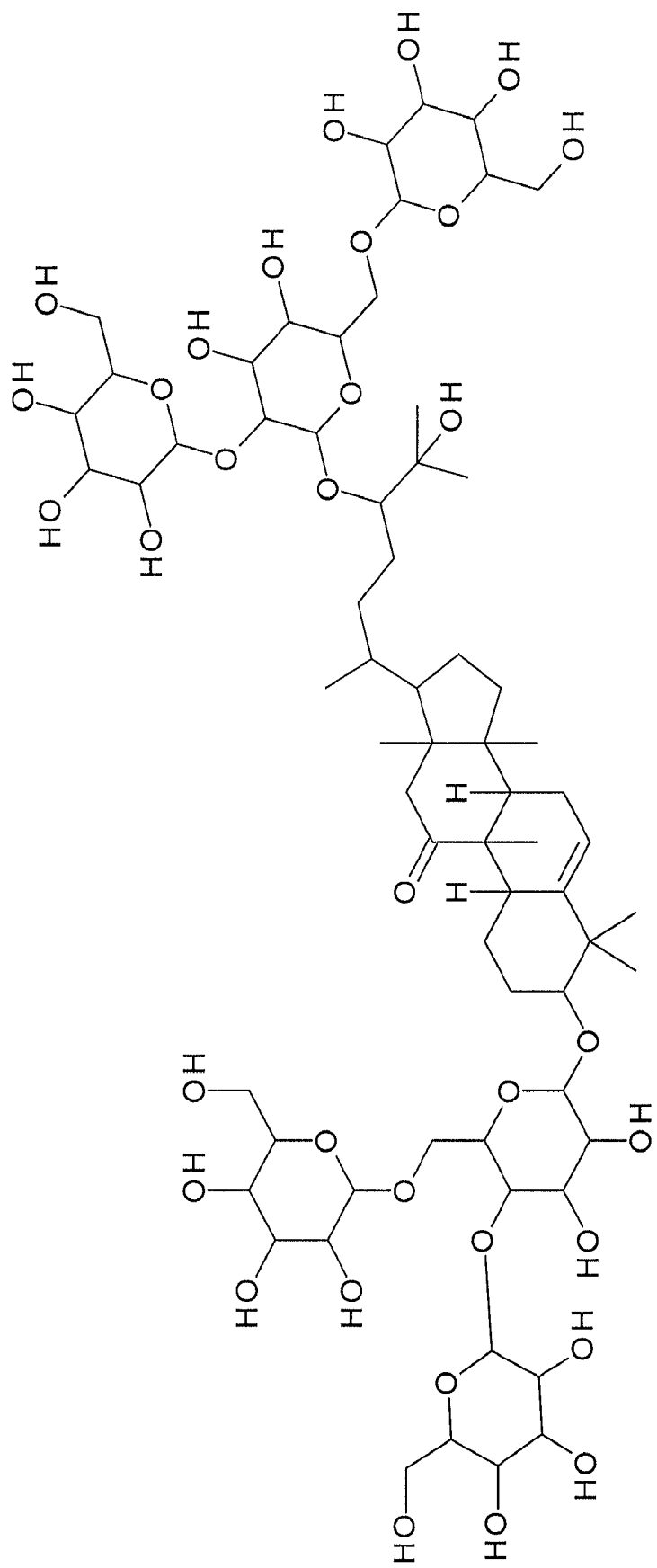
FIG. 7: Chemical structure of novel mogroside compound 7

Formula 4
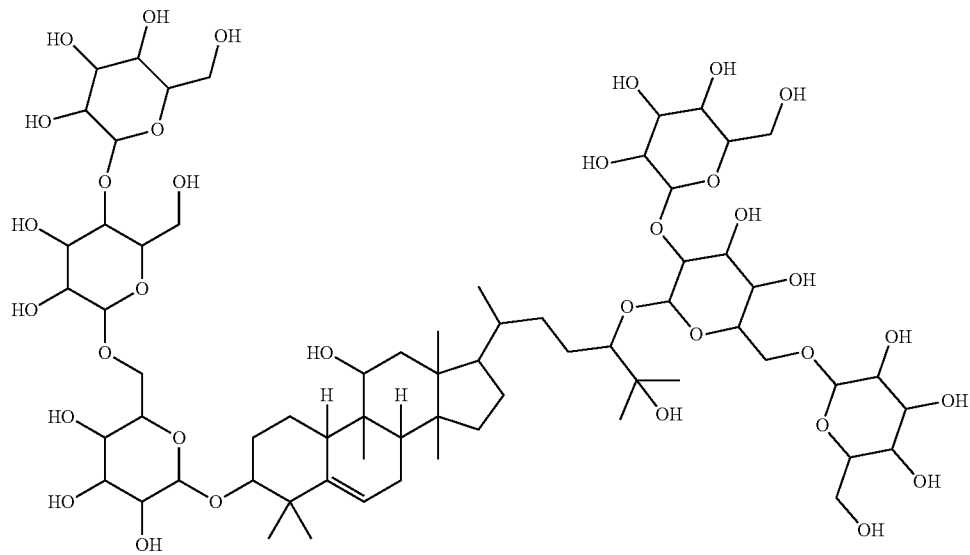
(FIG. 4)
Formula 5
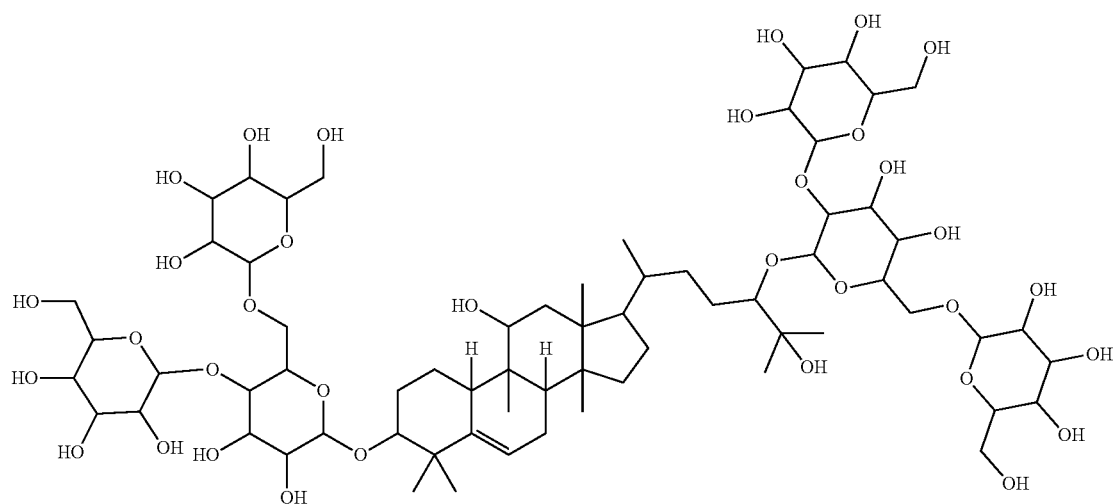
(FIG. 5)

Figure 8:
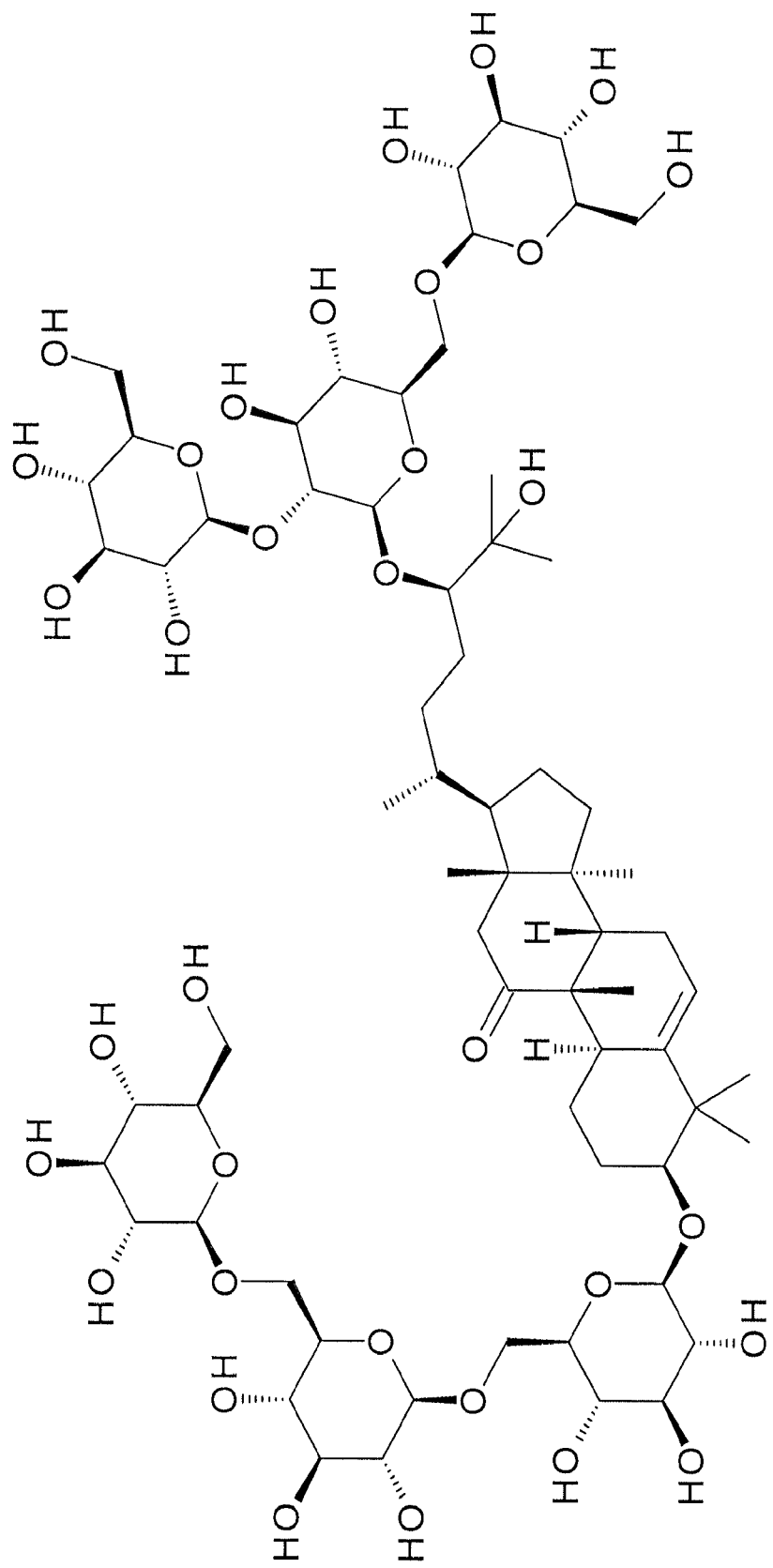
FIG. 8: Chemical structure of novel mogroside compound 8
Figure 9:
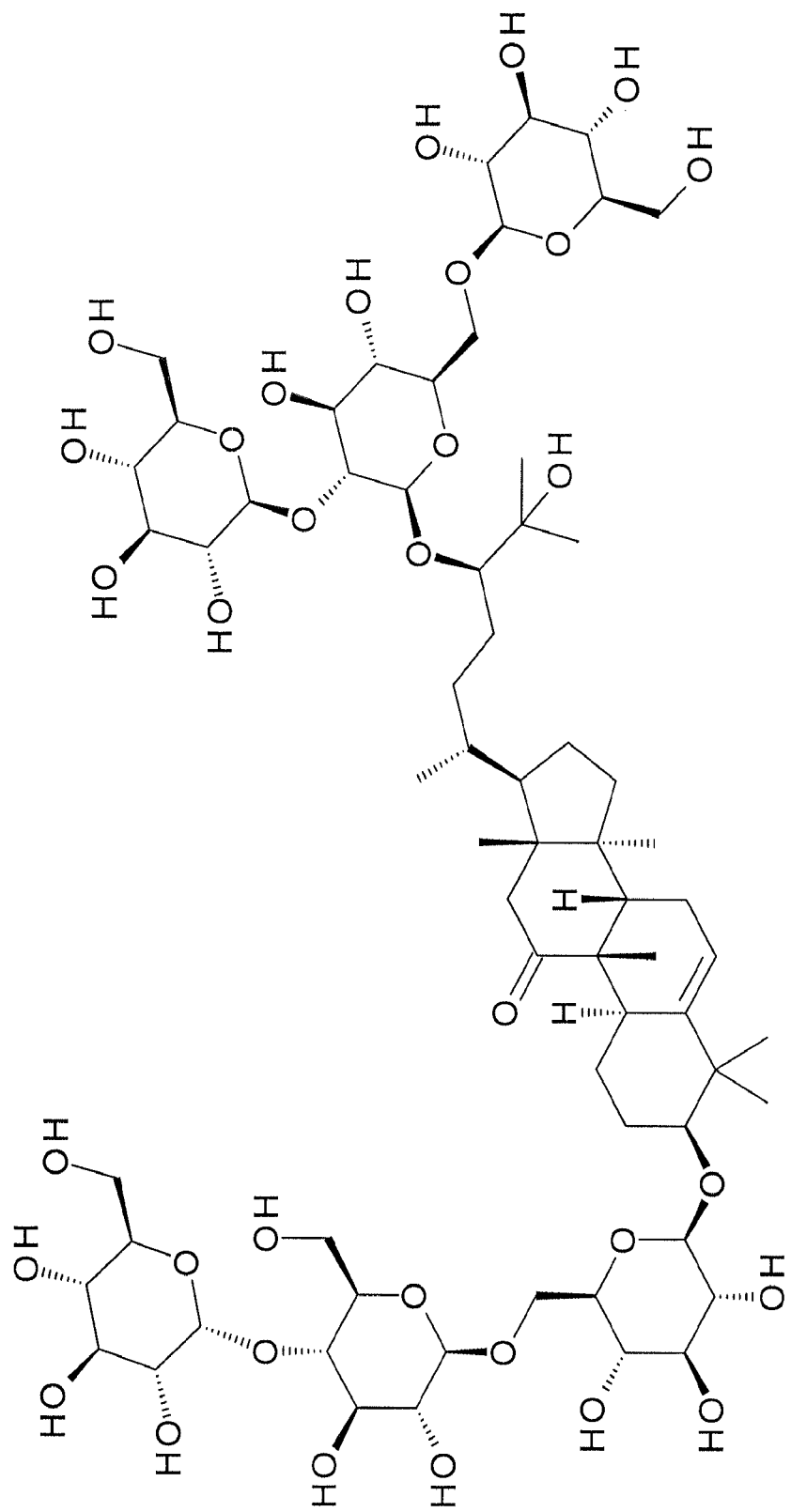
FIG. 9: Chemical structure of novel mogroside compound 9
Figure 10:
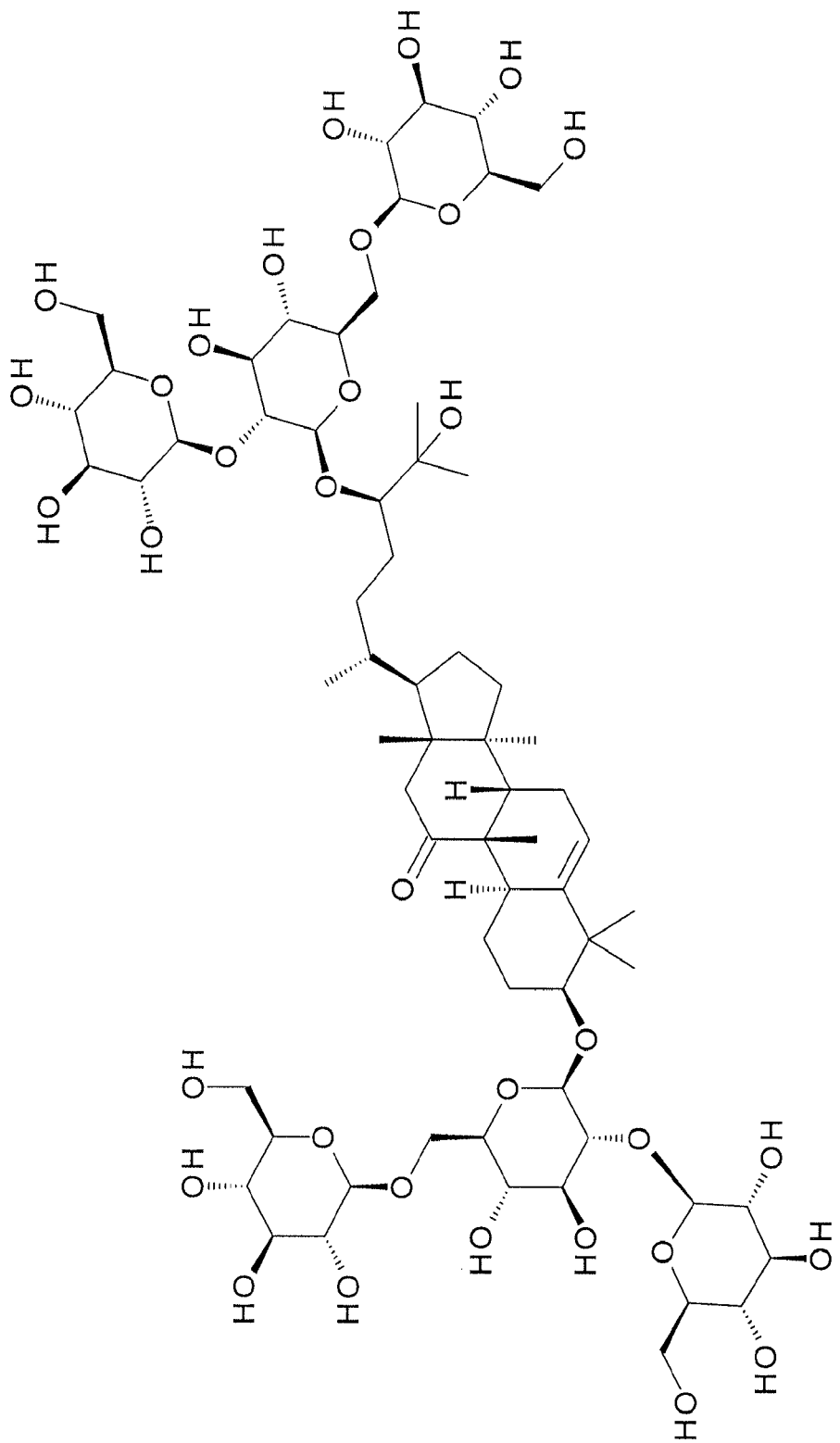
FIG. 10: Chemical structure of novel mogroside compound 10

Formula 7
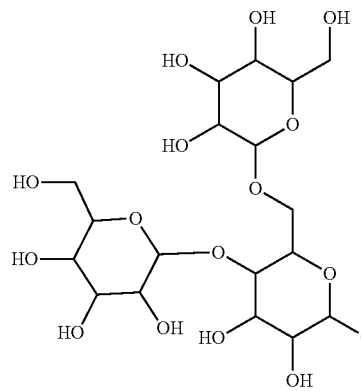 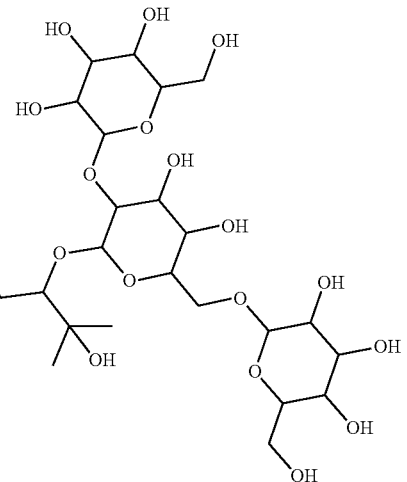
(FIG. 7)
Formula 8
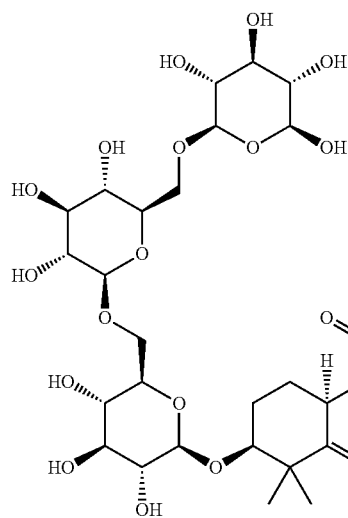 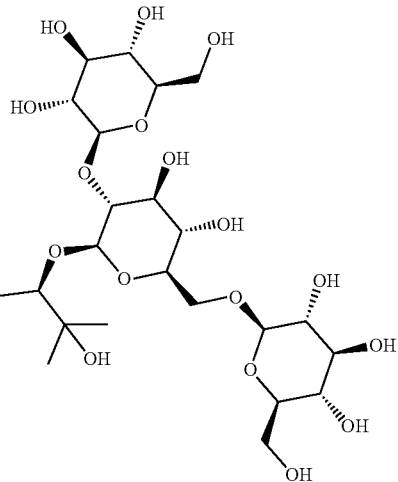
(FIG. 8)

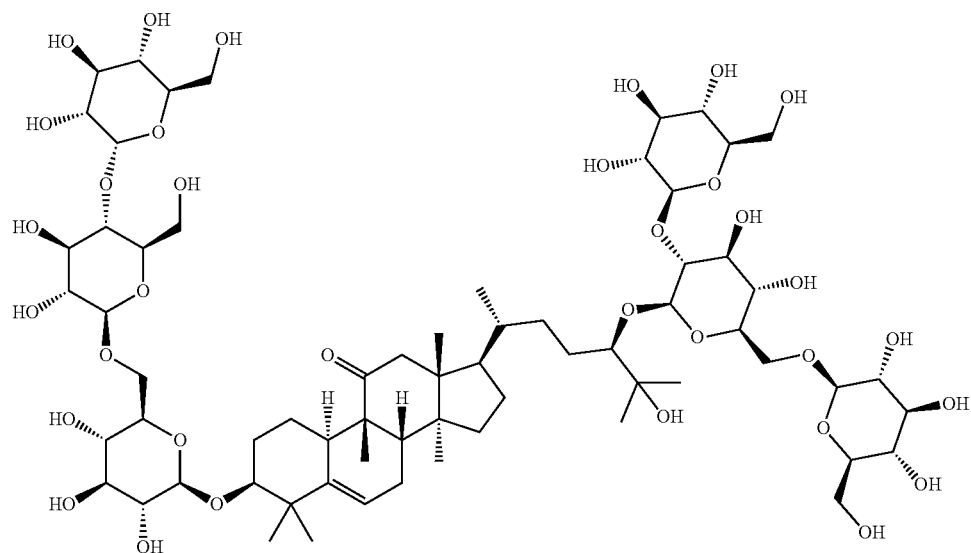
(FIG. 9)
Formula 9
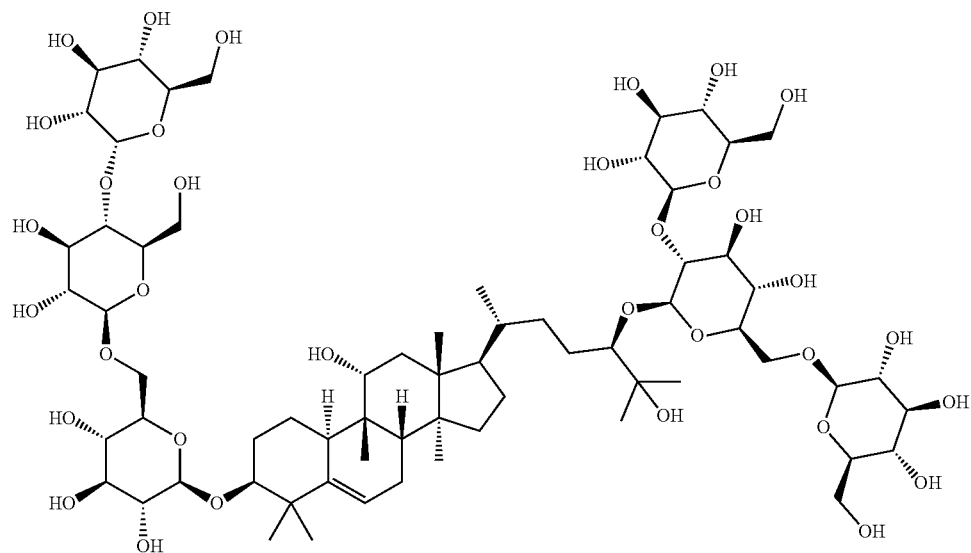
(FIG. 11)
Formula 11

Figure 14:
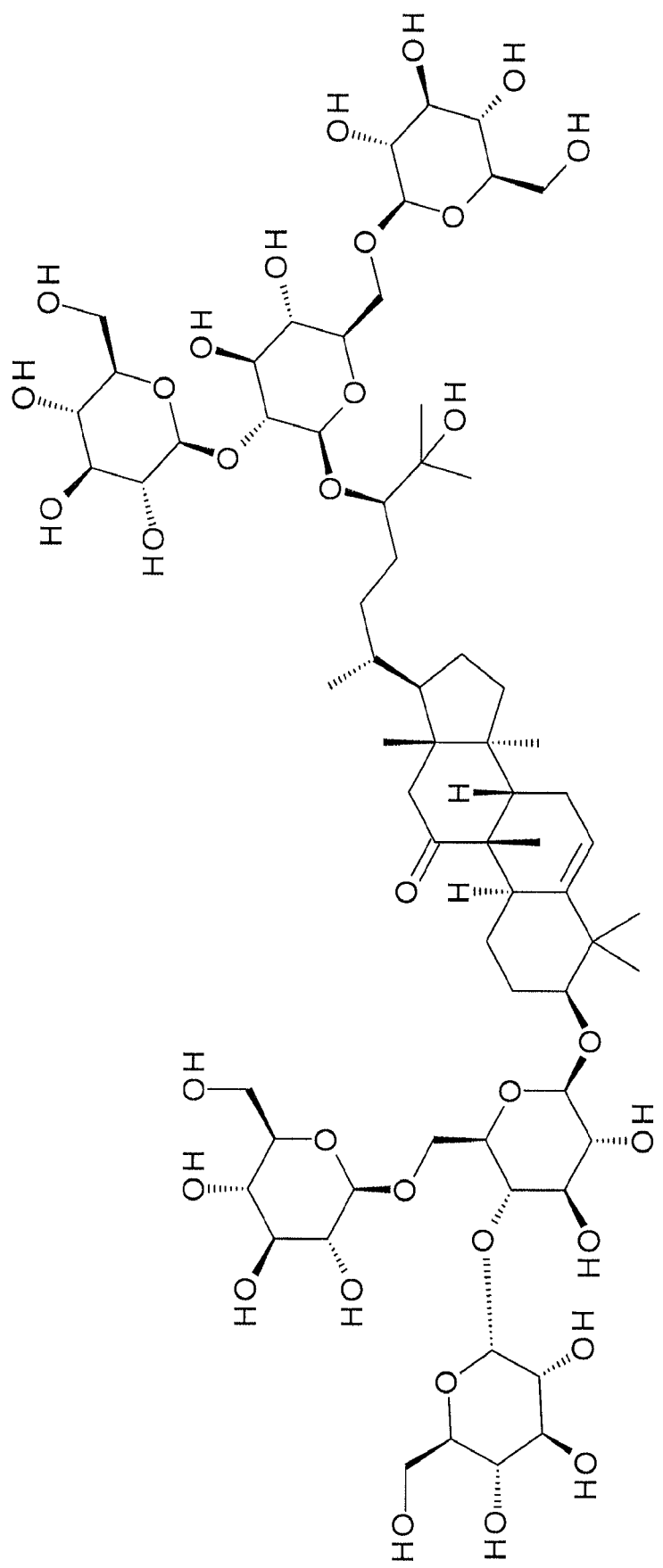
FIG. 14: Chemical structure of novel mogroside compound 14
Figure 15:
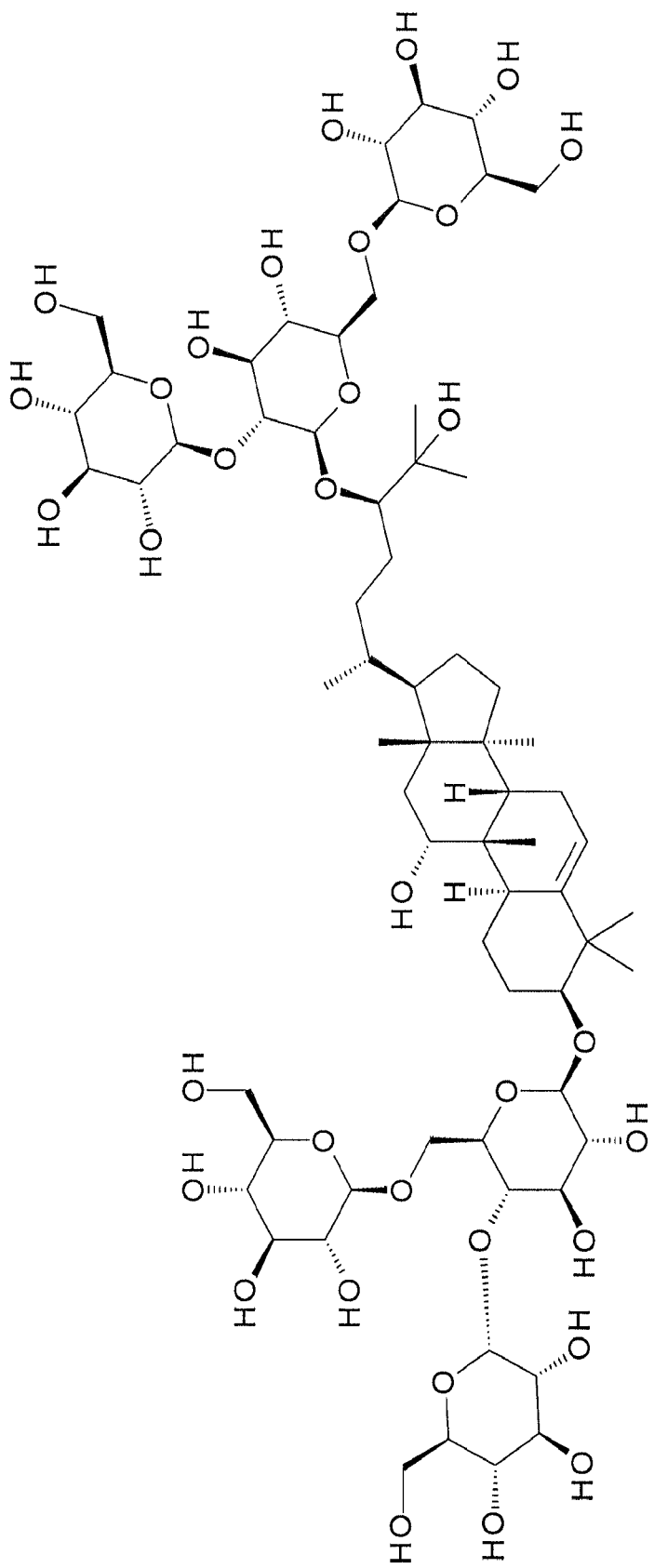
FIG. 15: Chemical structure of novel mogroside compound 15
Figure 16:
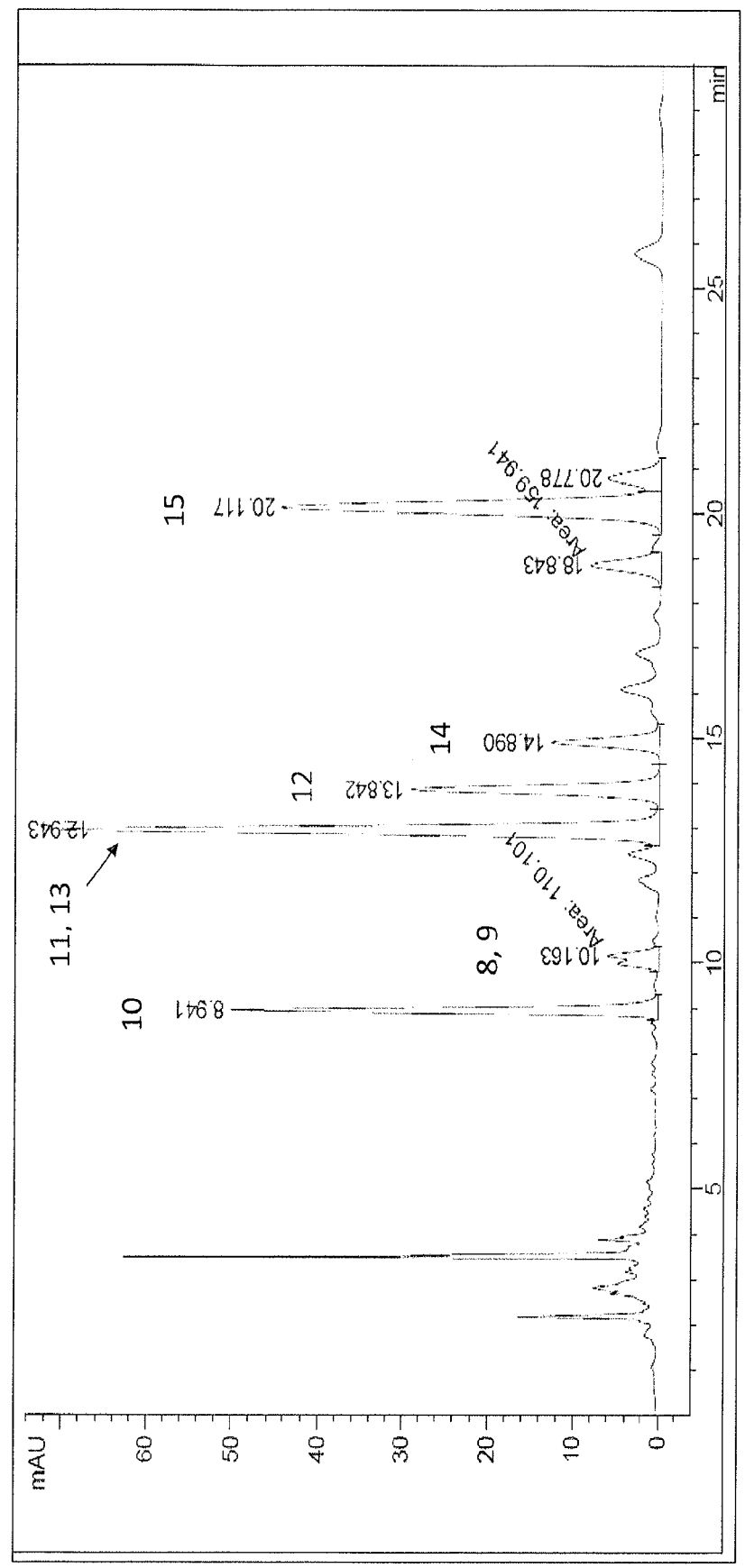
FIG. 16: Analytical-Preparative HPLC of mogroside mixtures
Figure 17:
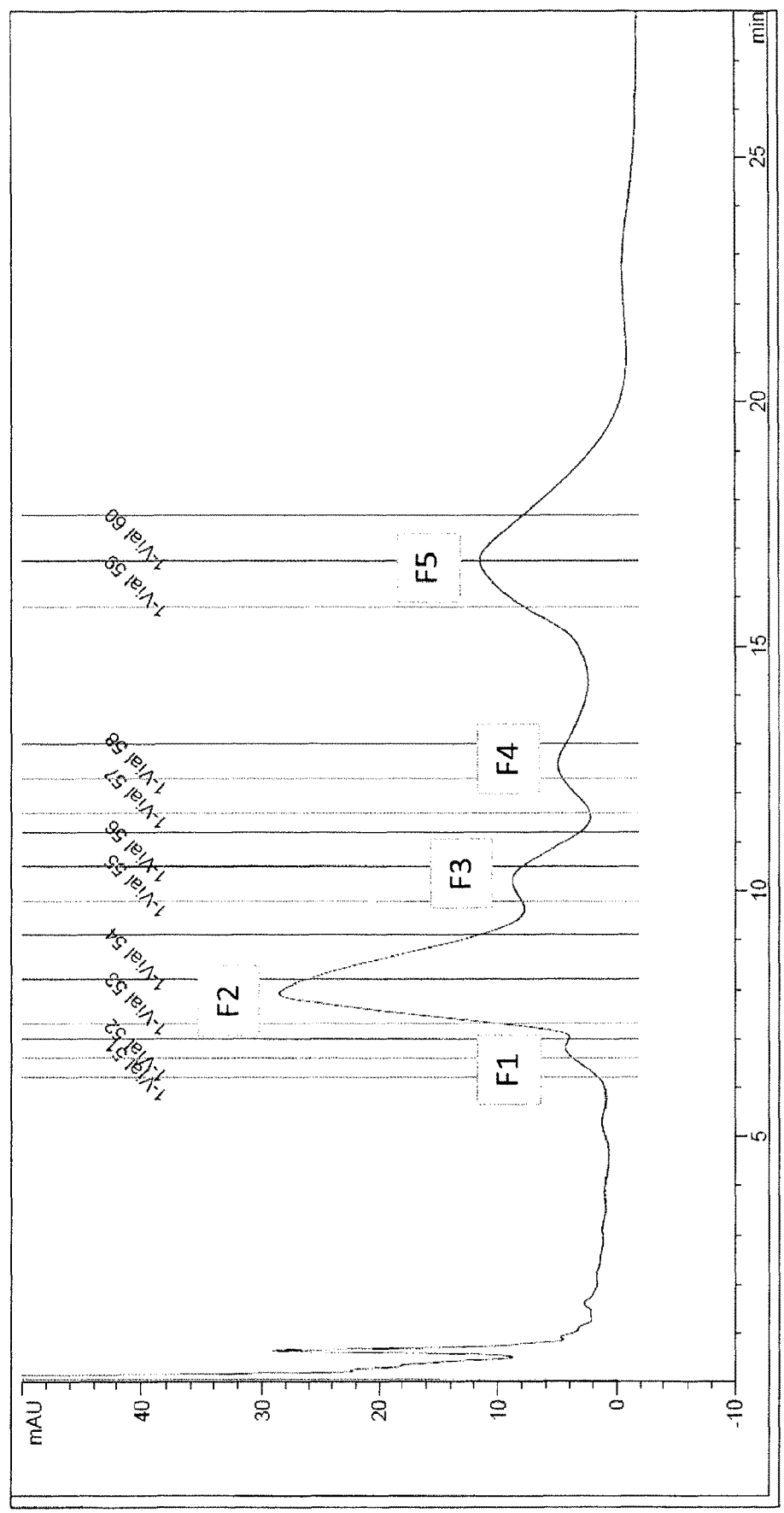
FIG. 17: Preparative HPLC of mogroside mixtures
Figure 18:
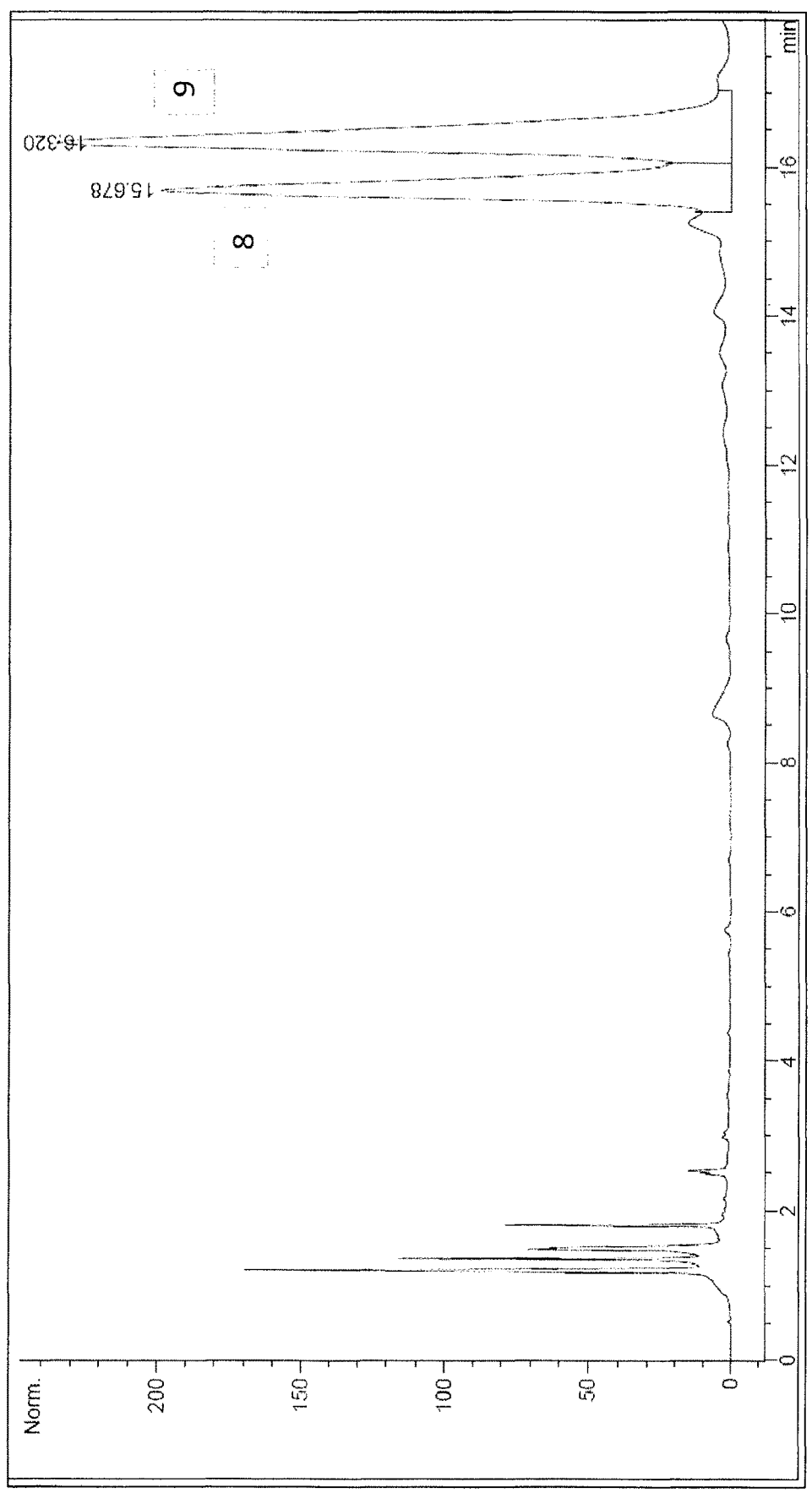
FIG. 18: Analytical-Preparative HPLC of Fraction 1 containing compounds 8 and 9
Figure 19:
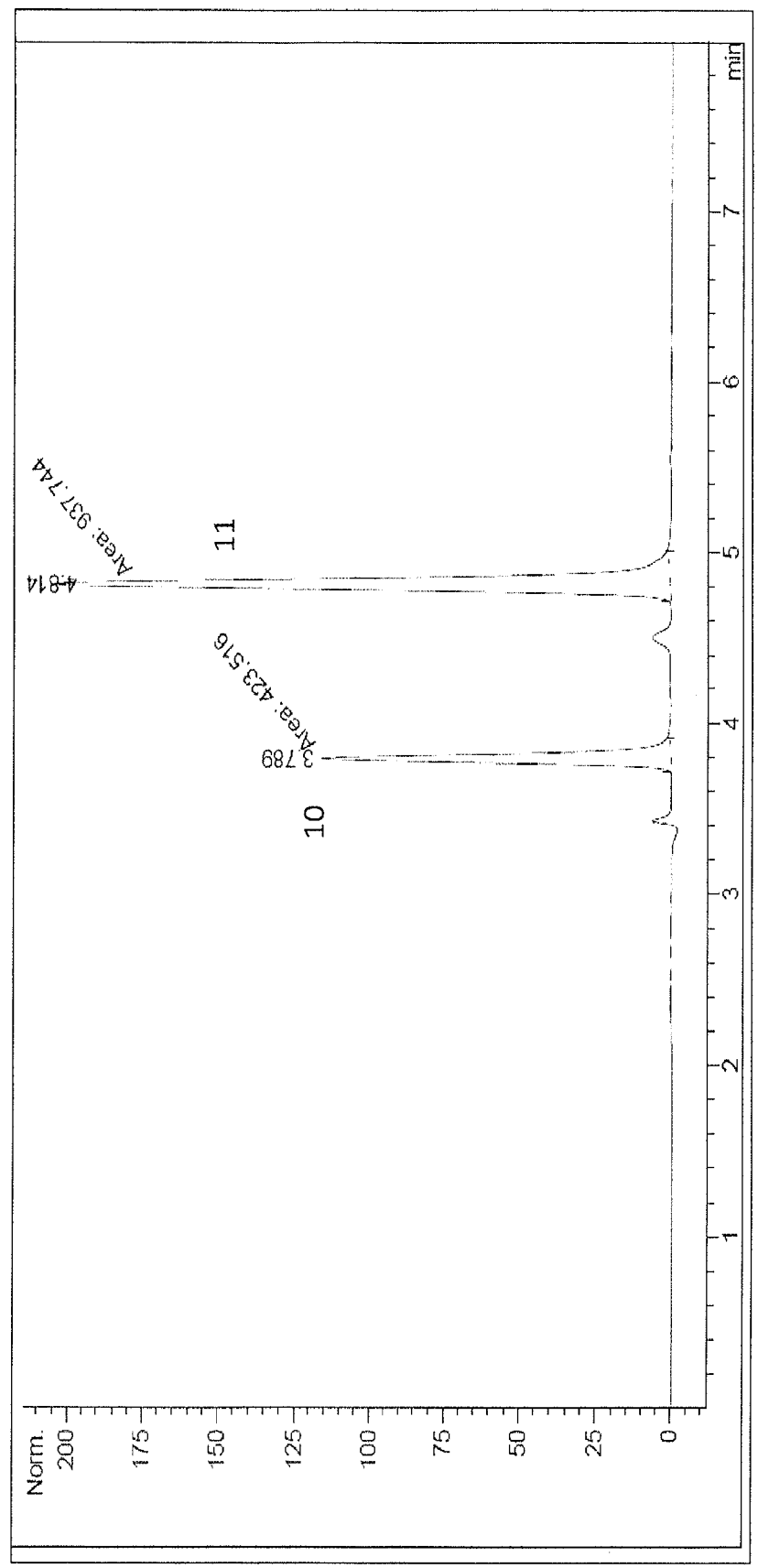
FIG. 19: Analytical-Preparative HPLC of Fraction 2 containing compounds 10 and 11
Figure 20:
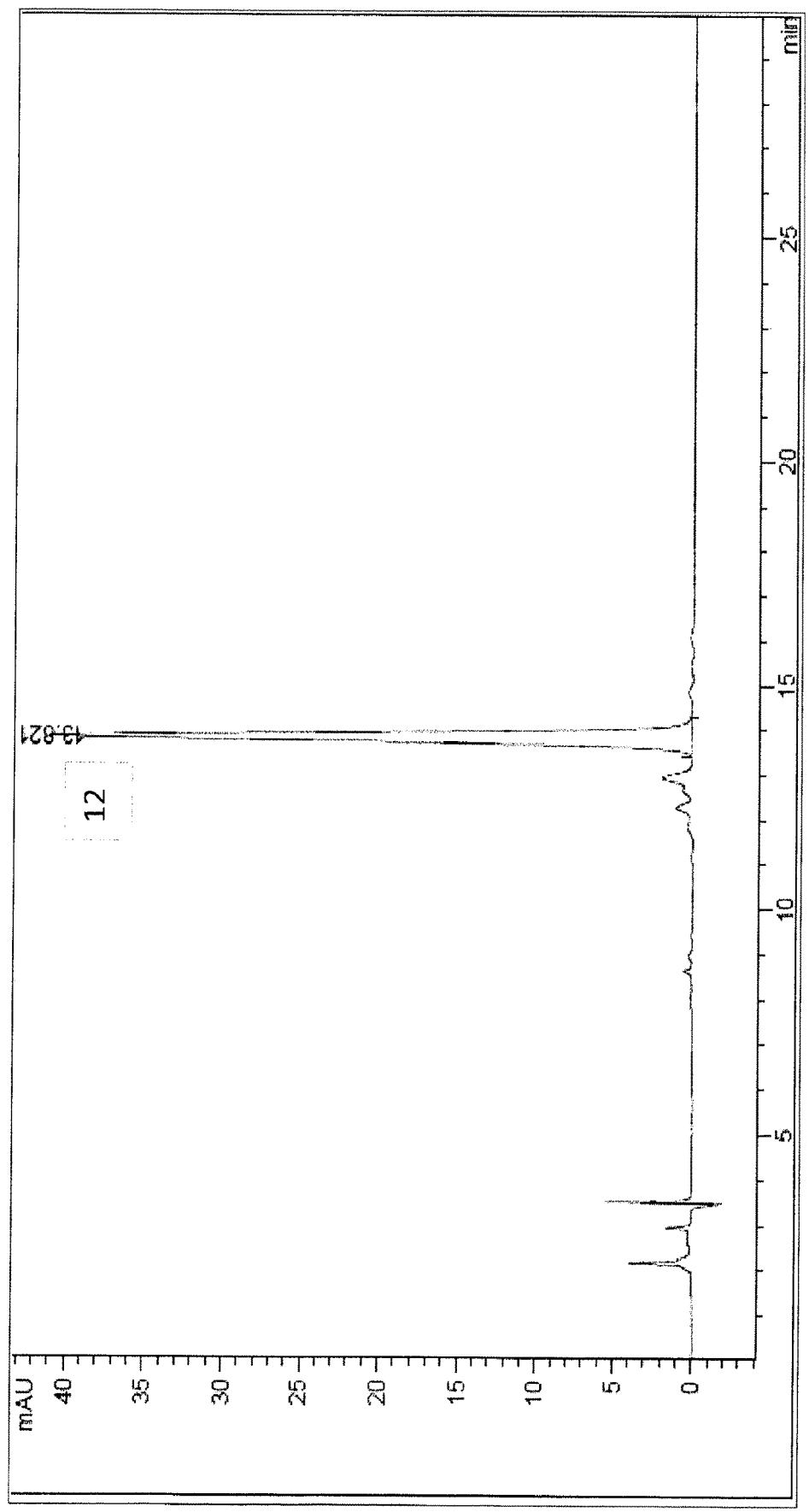
FIG. 20: Analytical-Preparative HPLC of Fraction 3 containing compound 12
Figure 21:
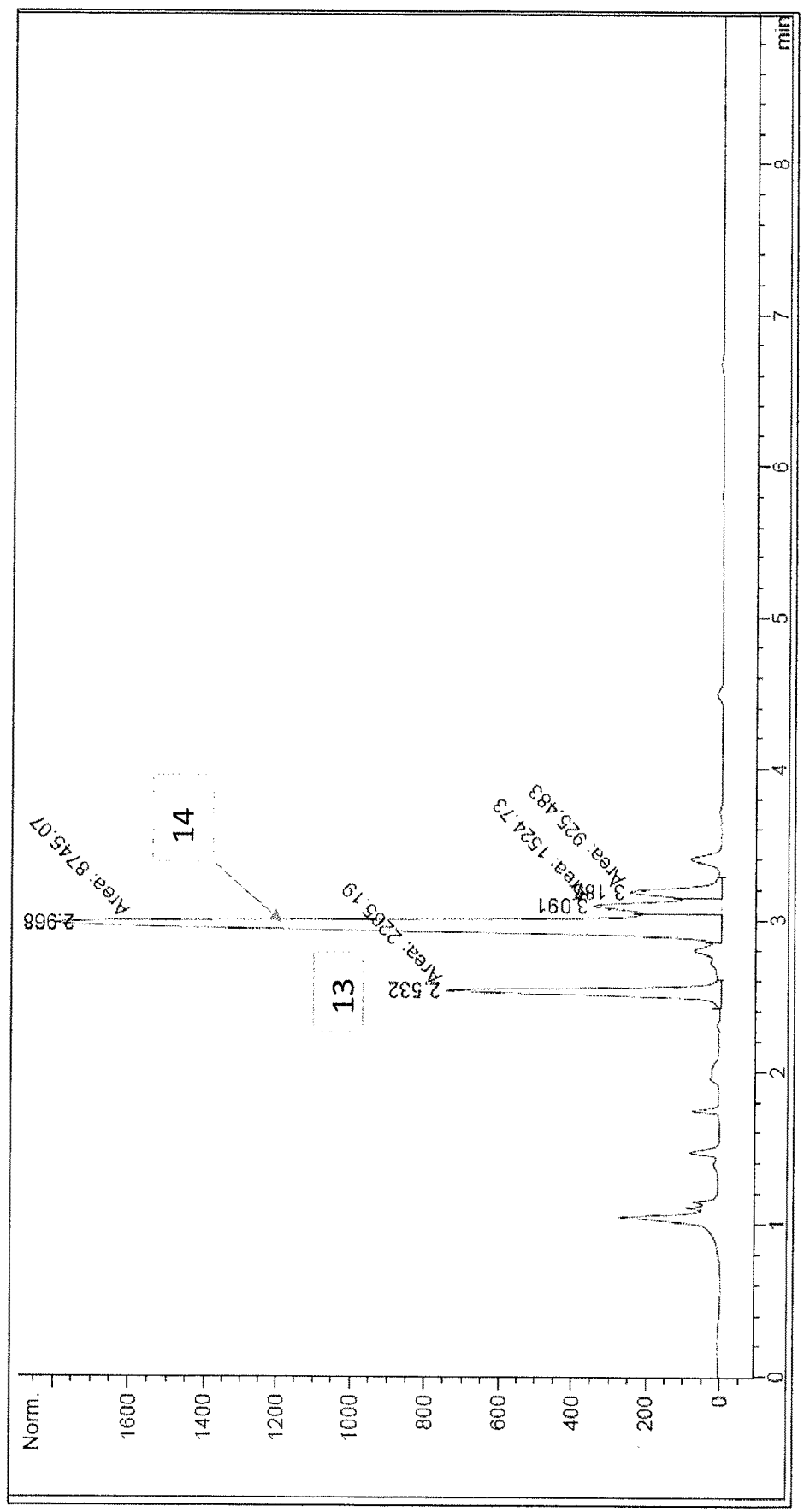
FIG. 21: Analytical-Preparative HPLC of Fraction 4 containing compounds 13.
Figure 22:
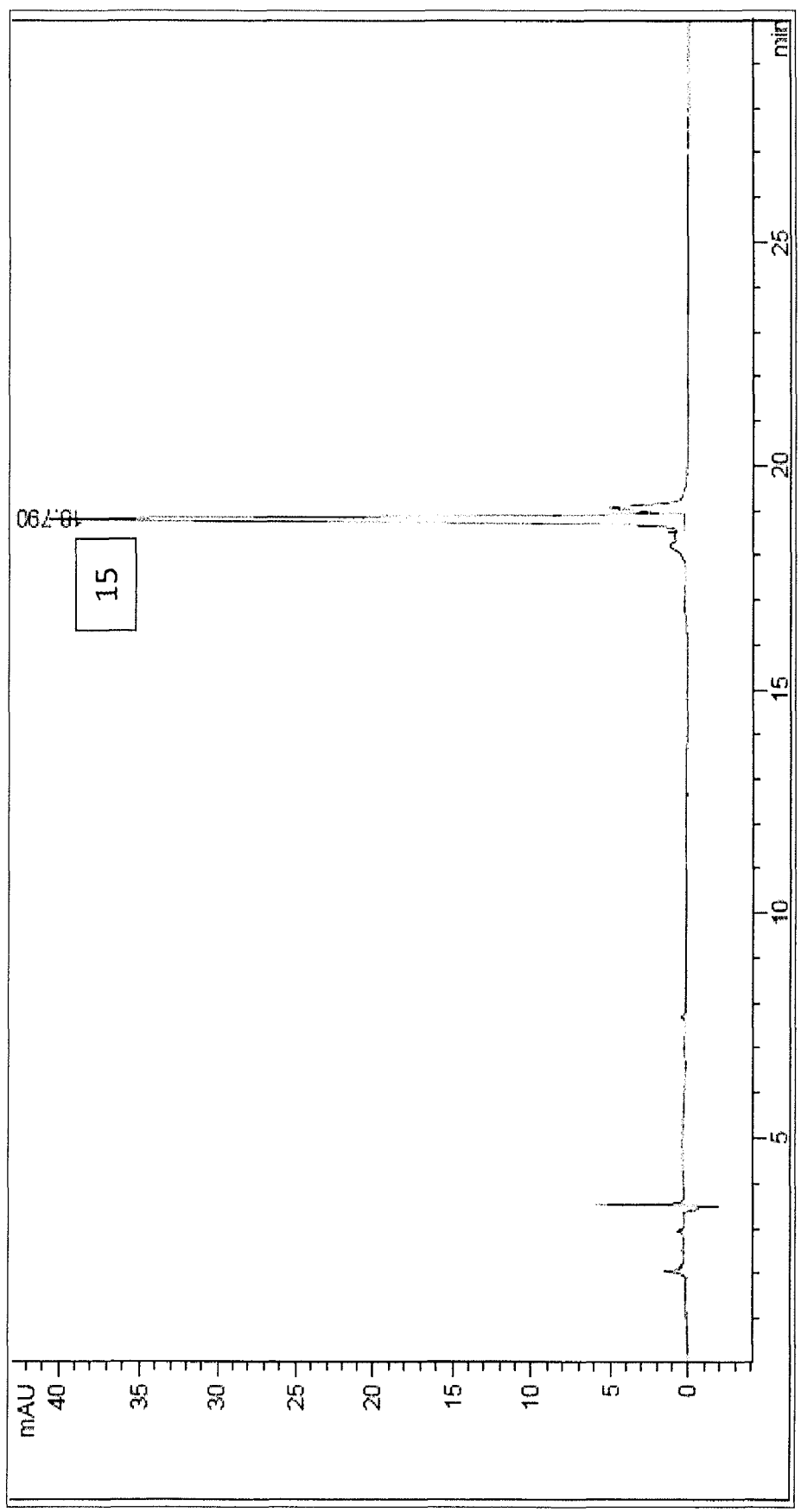
FIG. 22: Analytical-Preparative HPLC of Fraction 5 containing compound 15.
Figure 23:
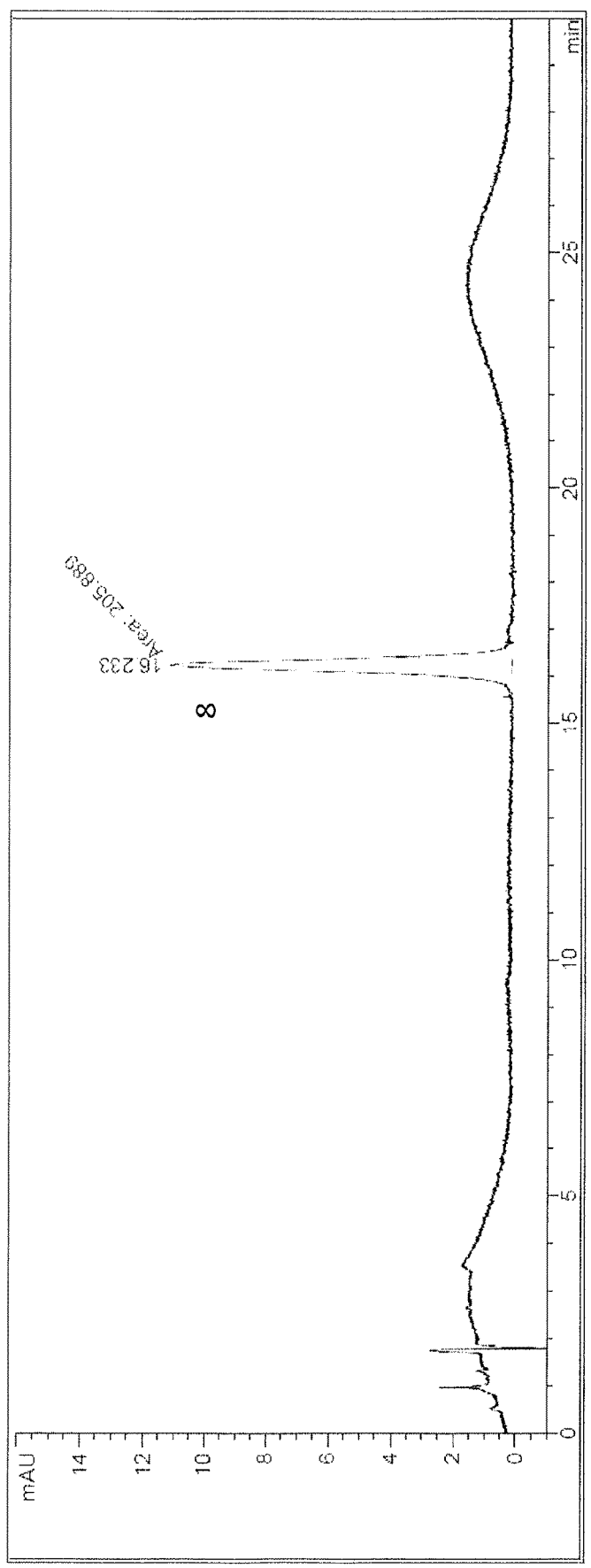
FIG. 23: Analytical-Preparative HPLC of compound 8
Figure 24:
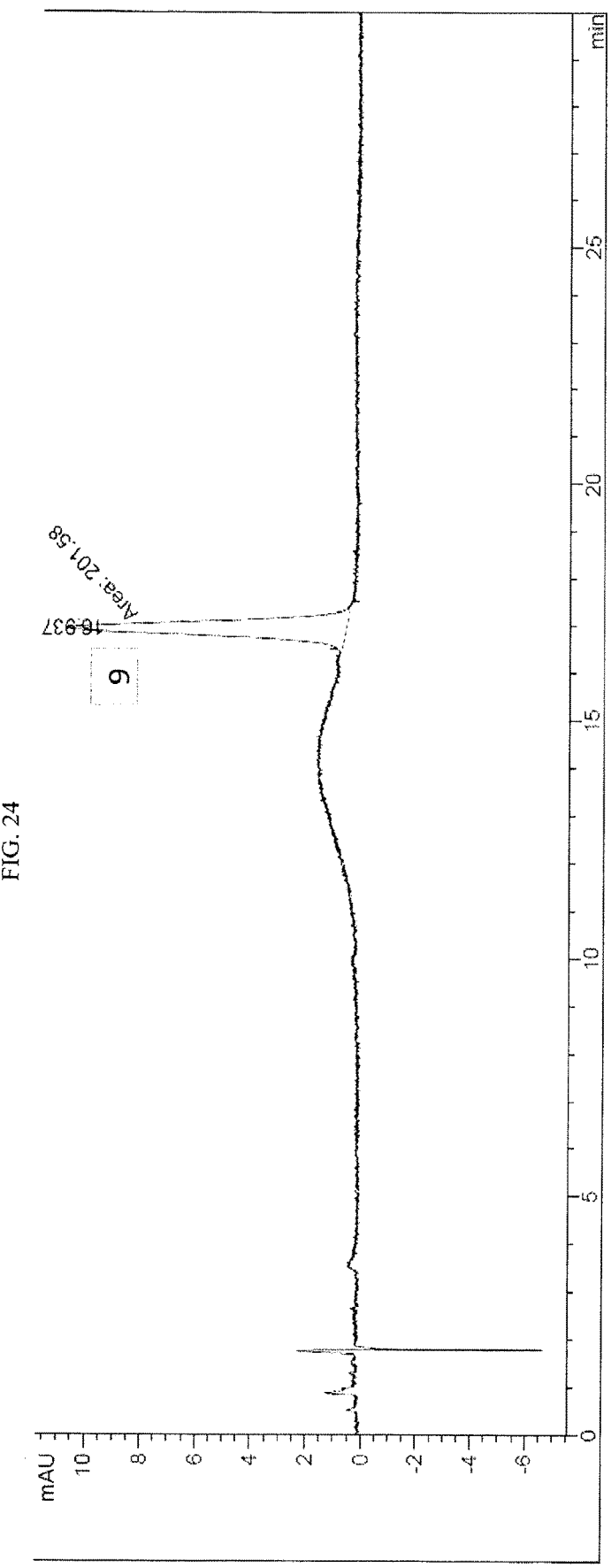
FIG. 24: Analytical-Preparative HPLC of compound 9
Figure 25:
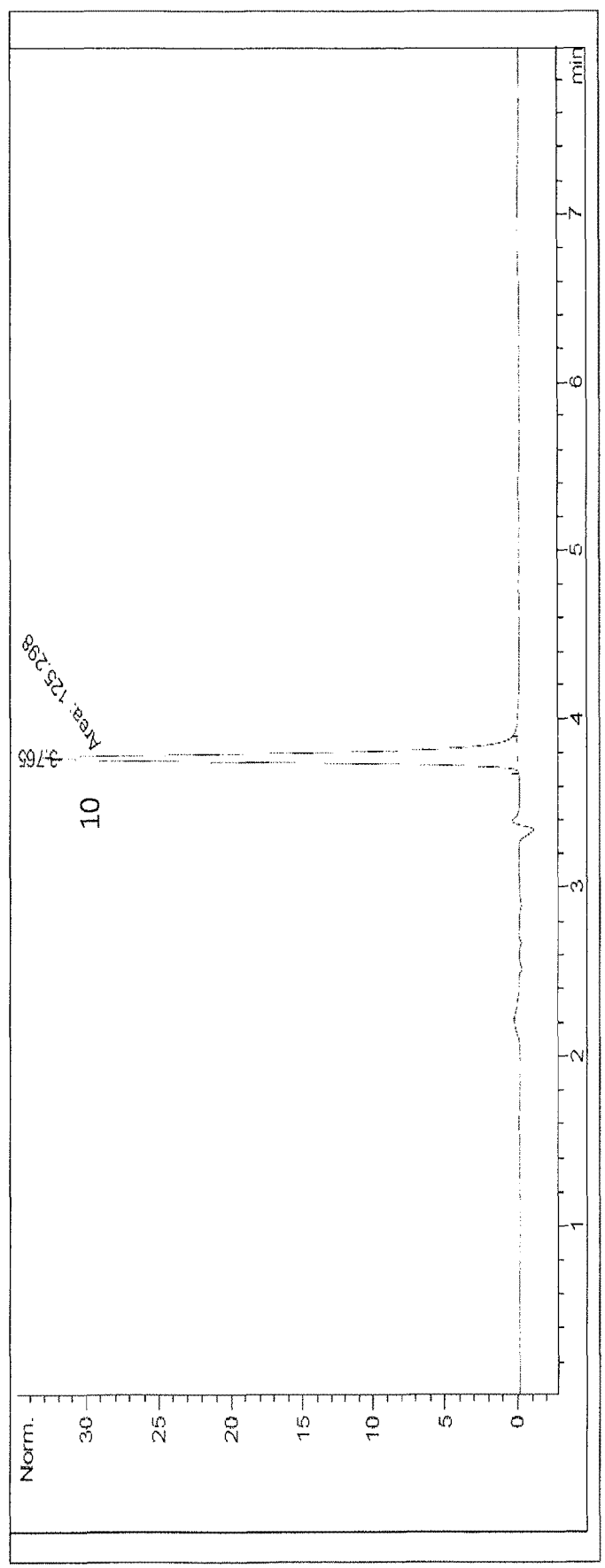
FIG. 25: Analytical-Preparative HPLC of compound 10
Figure 26:
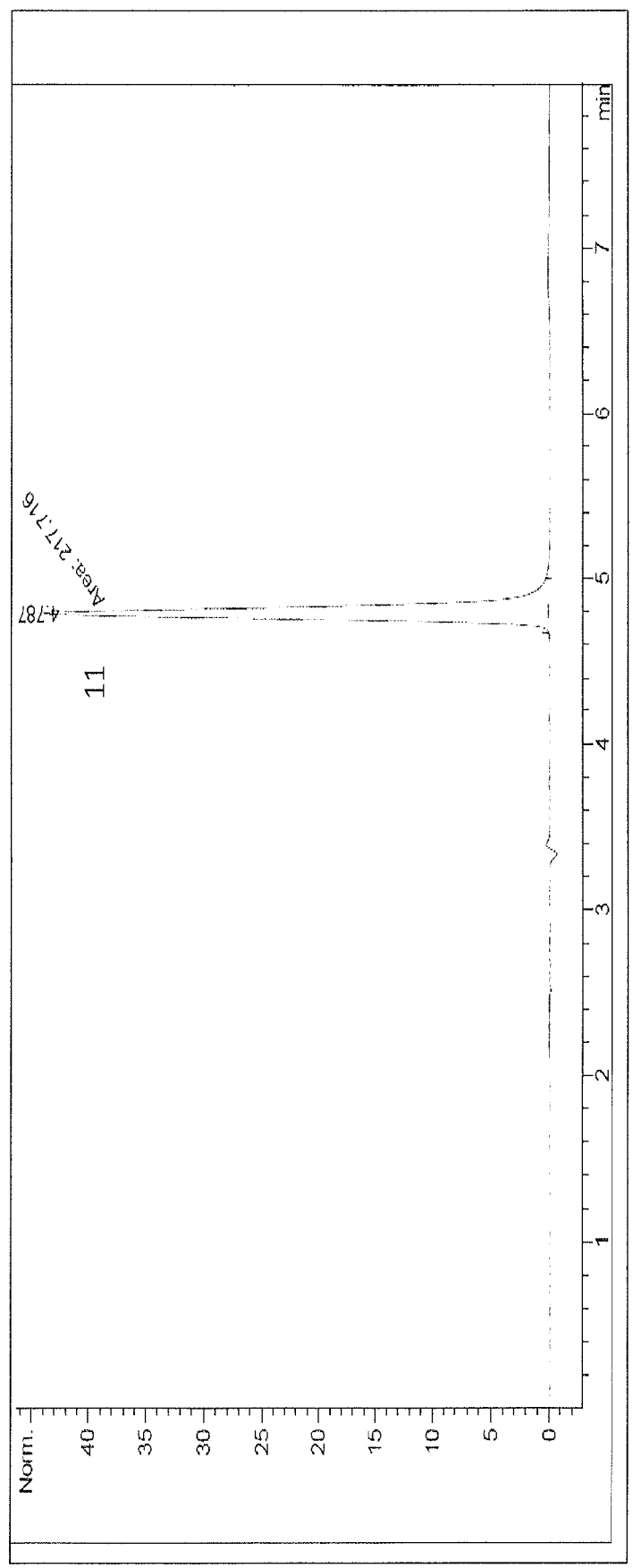
FIG. 26: Analytical-Preparative HPLC of compound 11
Figure 27:
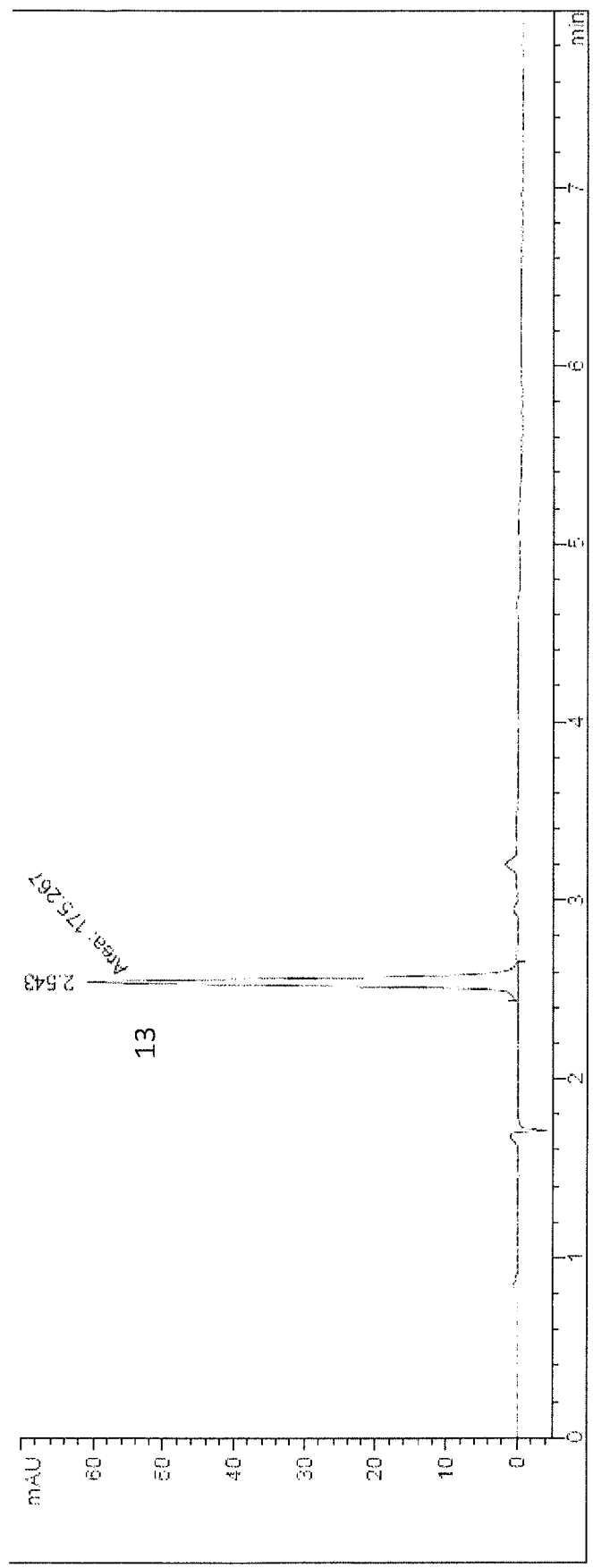
FIG. 27: Analytical-Preparative HPLC of compound 13
Figure 28:
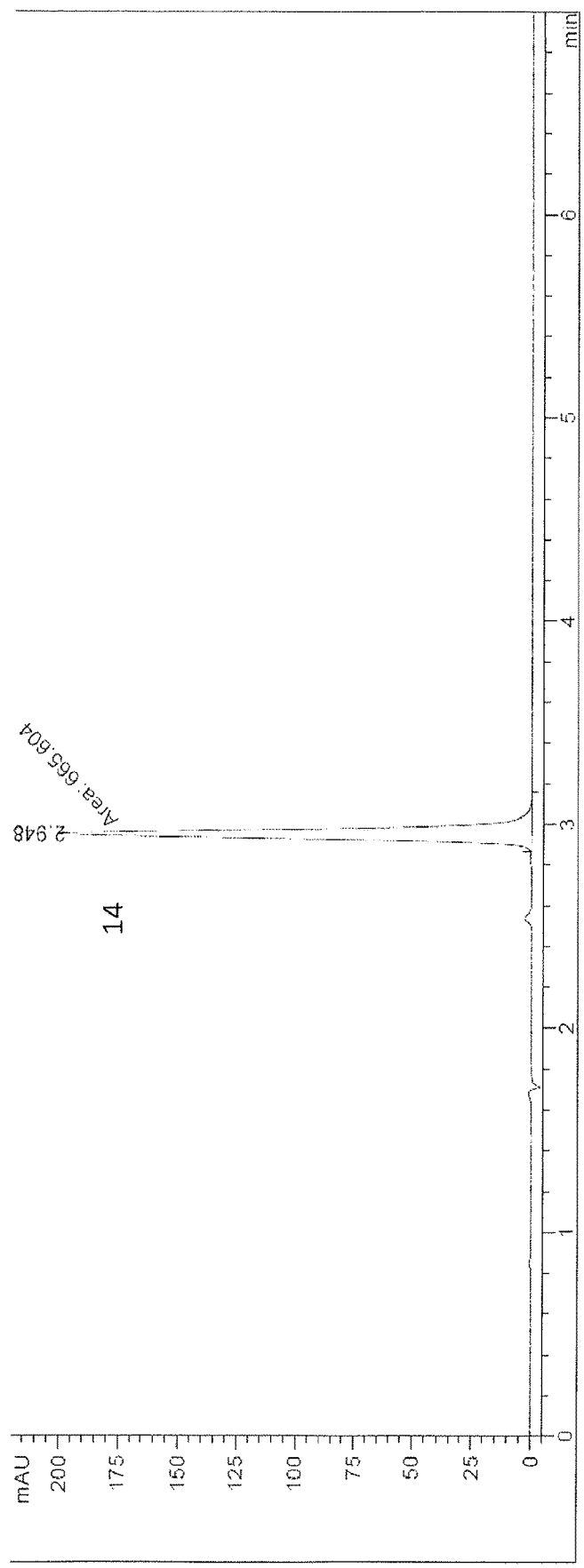
FIG. 28: Analytical-Preparative HPLC of compound 14
Figure 29A:
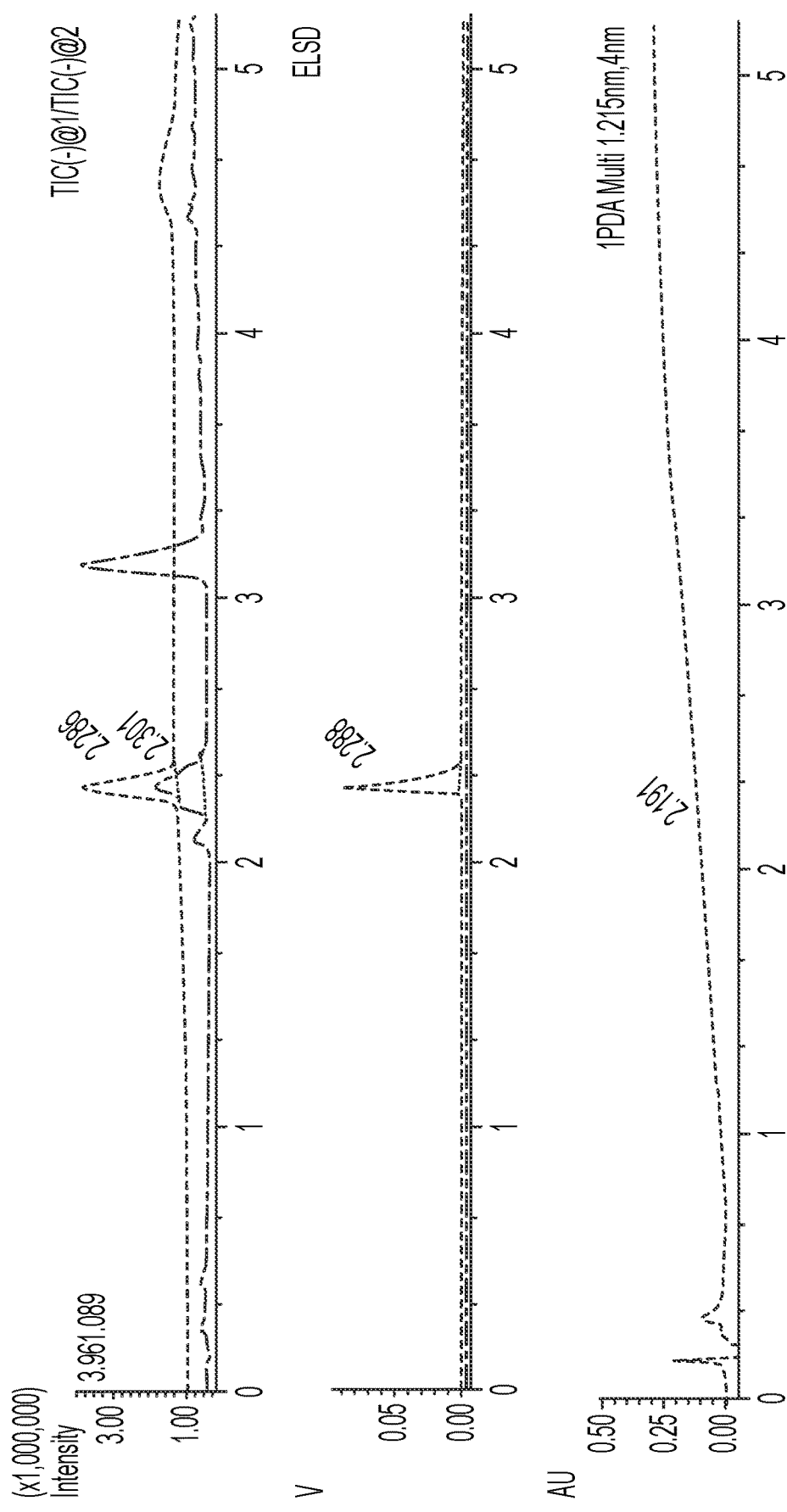
FIG. 29: LCMS of compound 8
Figure 32:
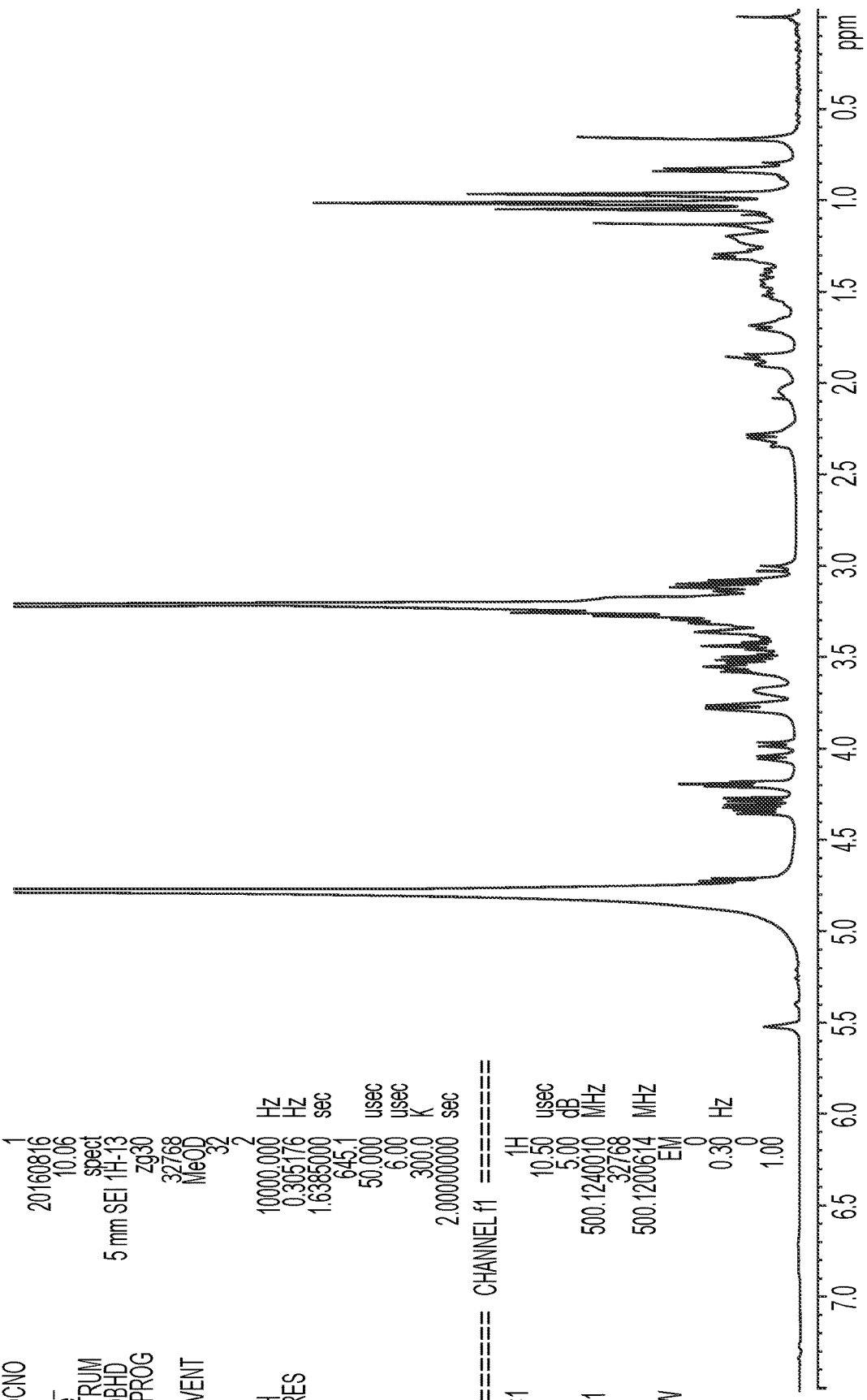
FIG. 32: 1H NMR spectrum of compound 8
Figure 33A:
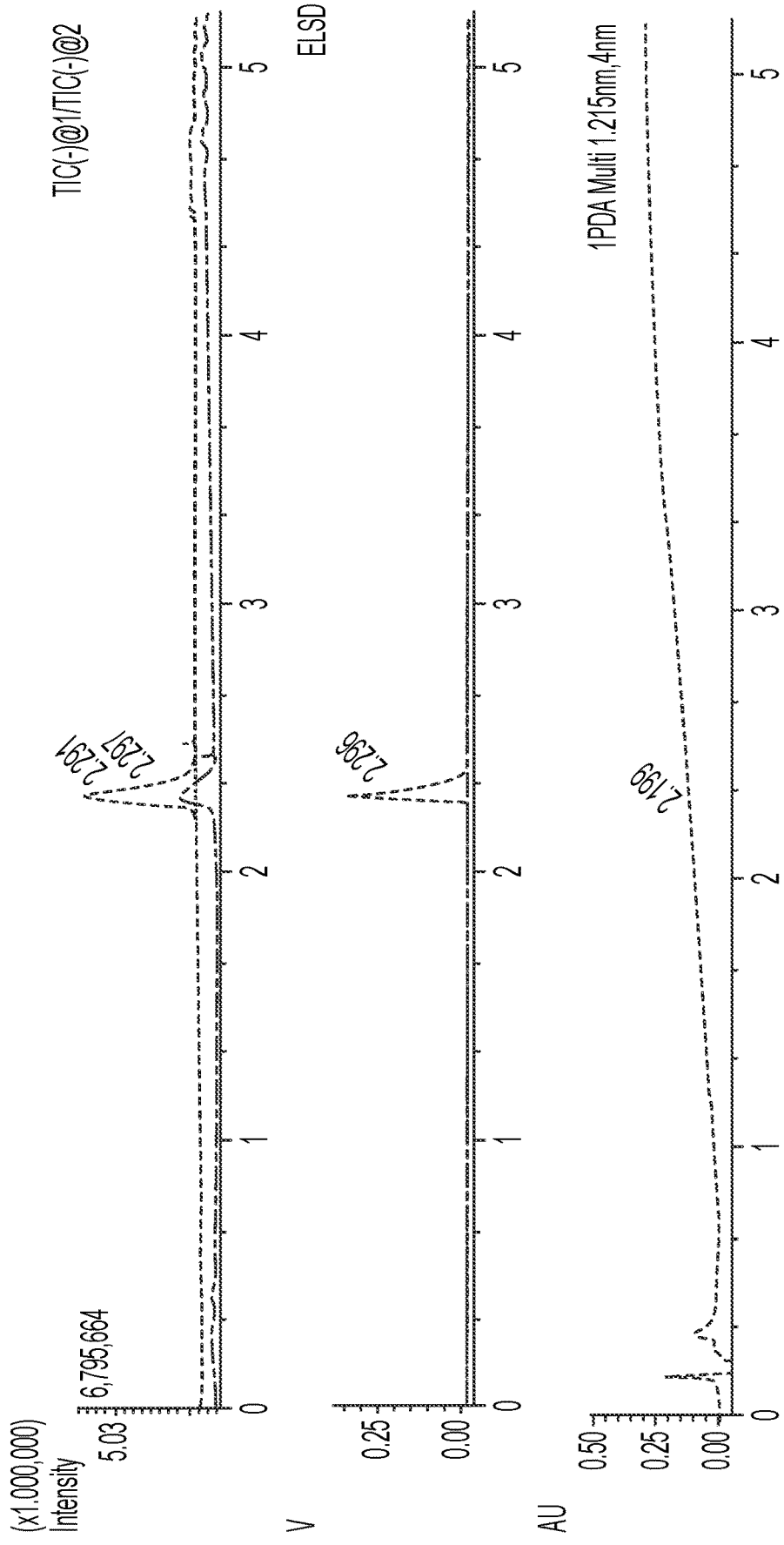
FIG. 33: LCMS of compound 9
Figure 33B:
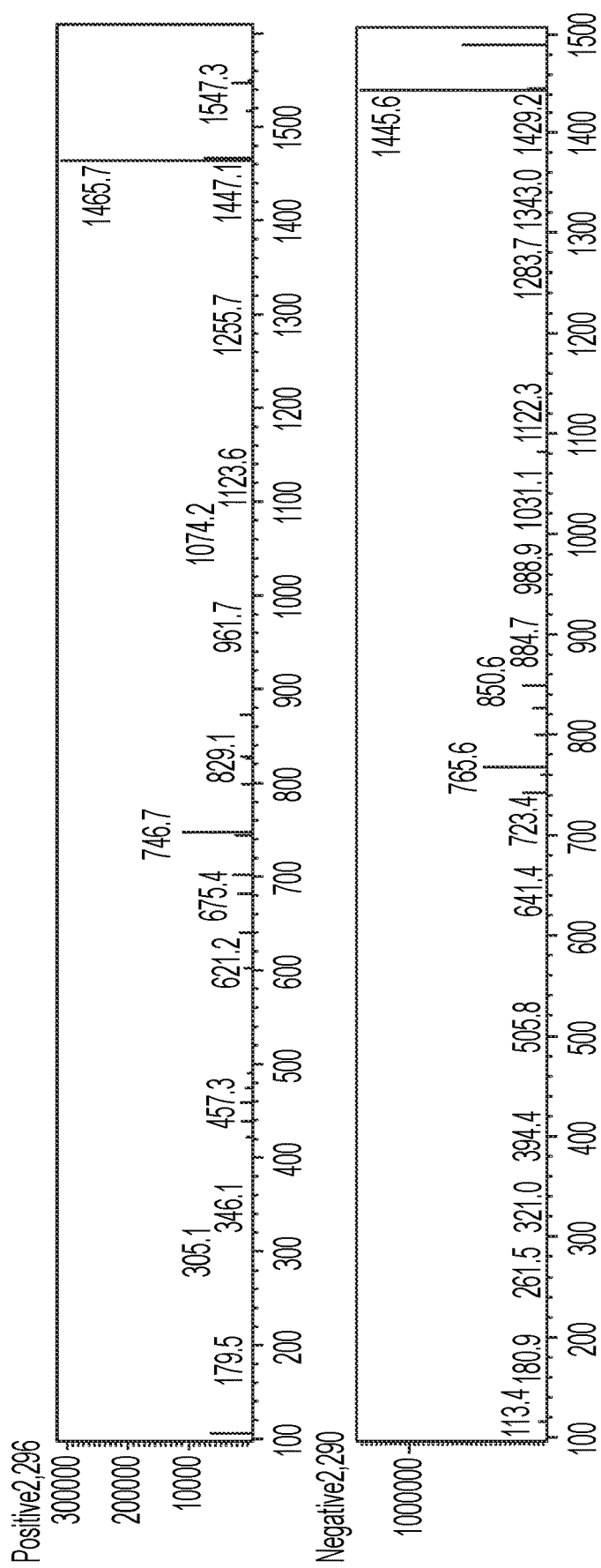
Figure 36:
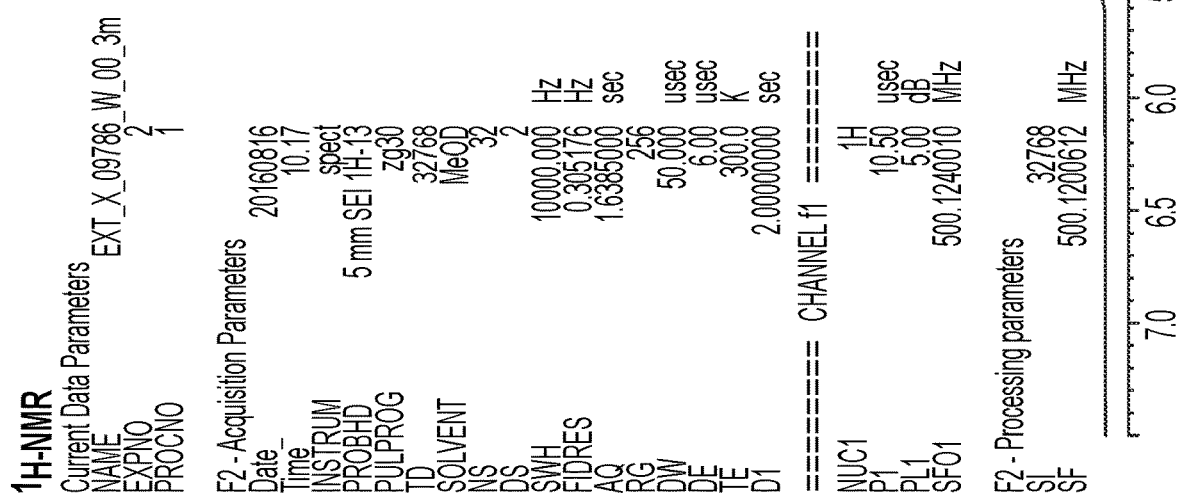
FIG. 36: 1H NMR spectrum of compound 9
Figure 37B:
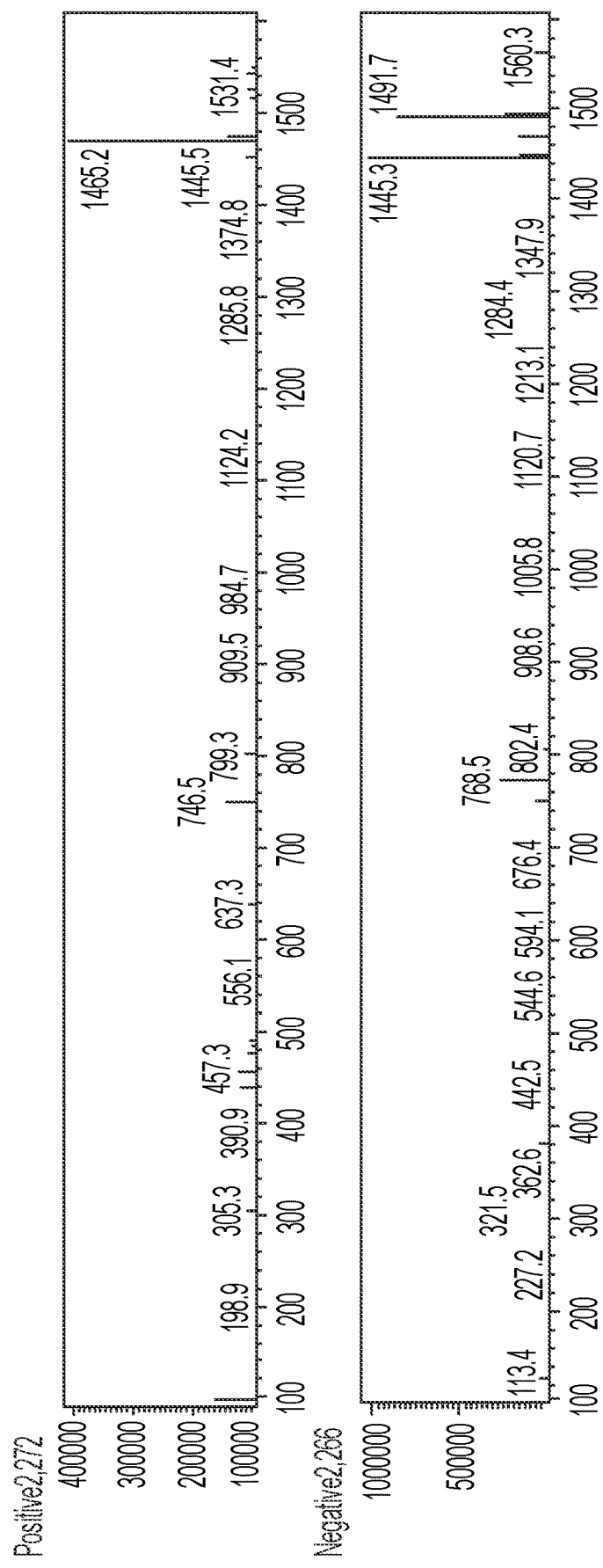
FIG. 37: LCMS of compound 10
Figure 40:
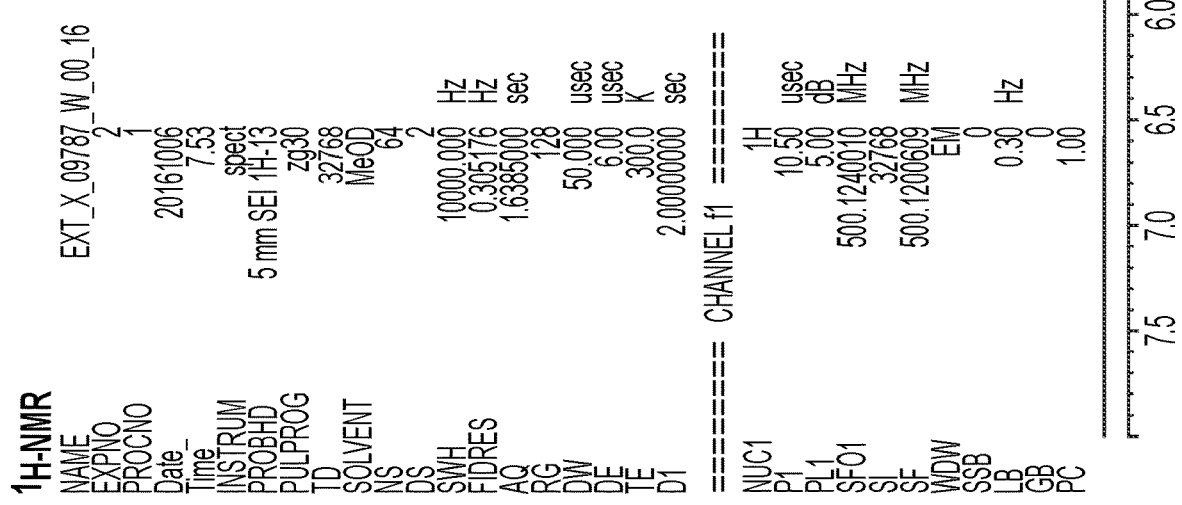
FIG. 40: 1H NMR spectrum of compound 10
Figure 41A:
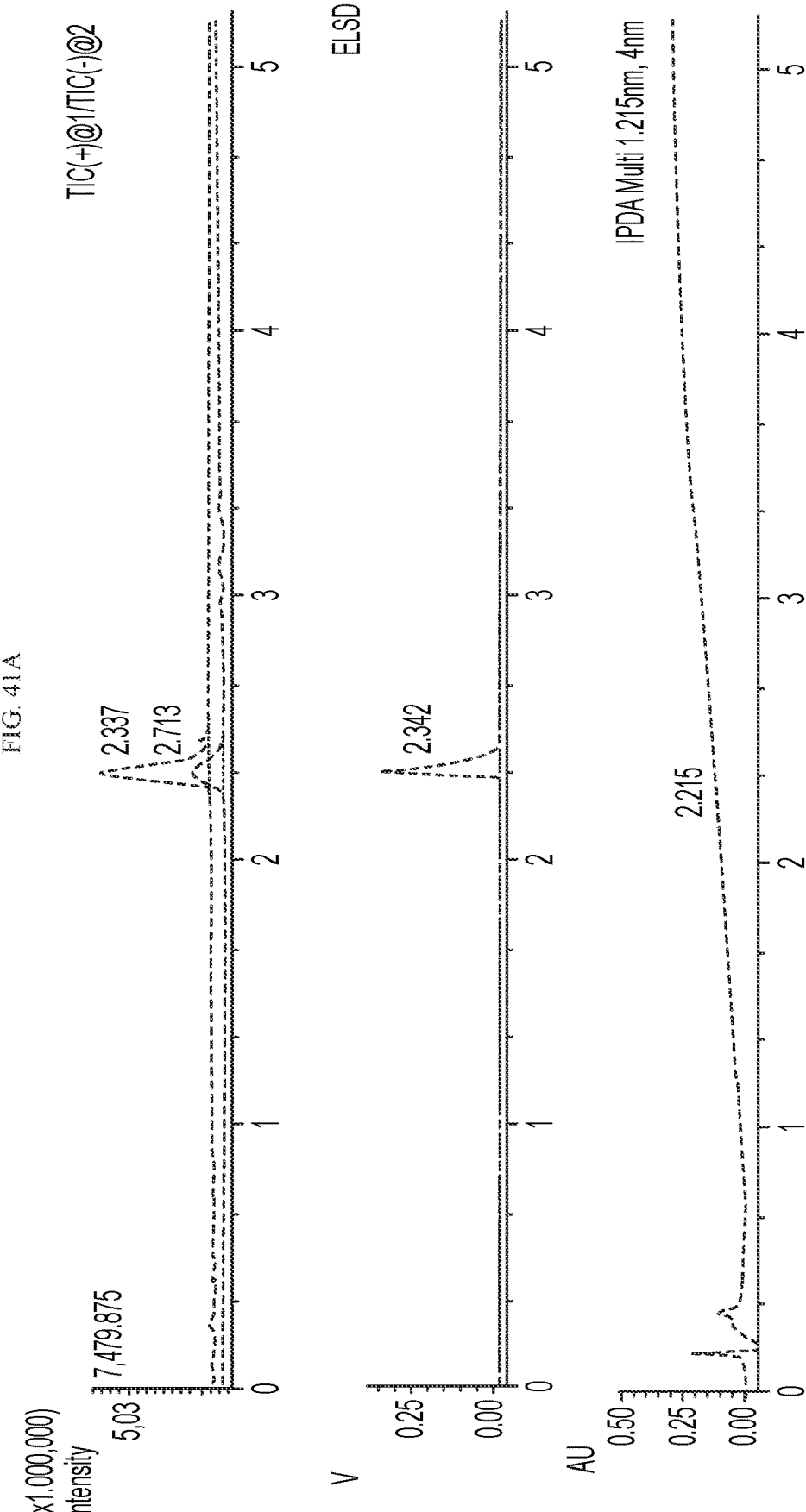
FIG. 41: LCMS of compound 11
Figure 41B:
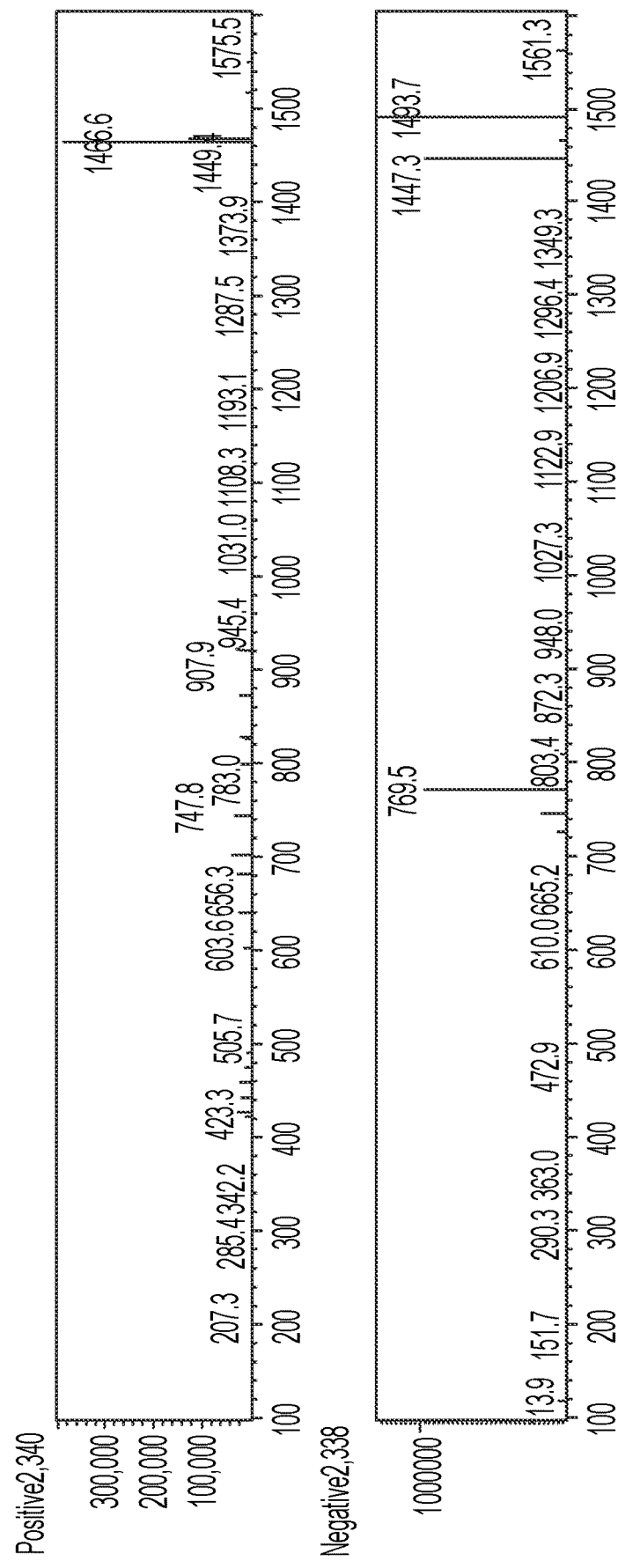
Figure 44:
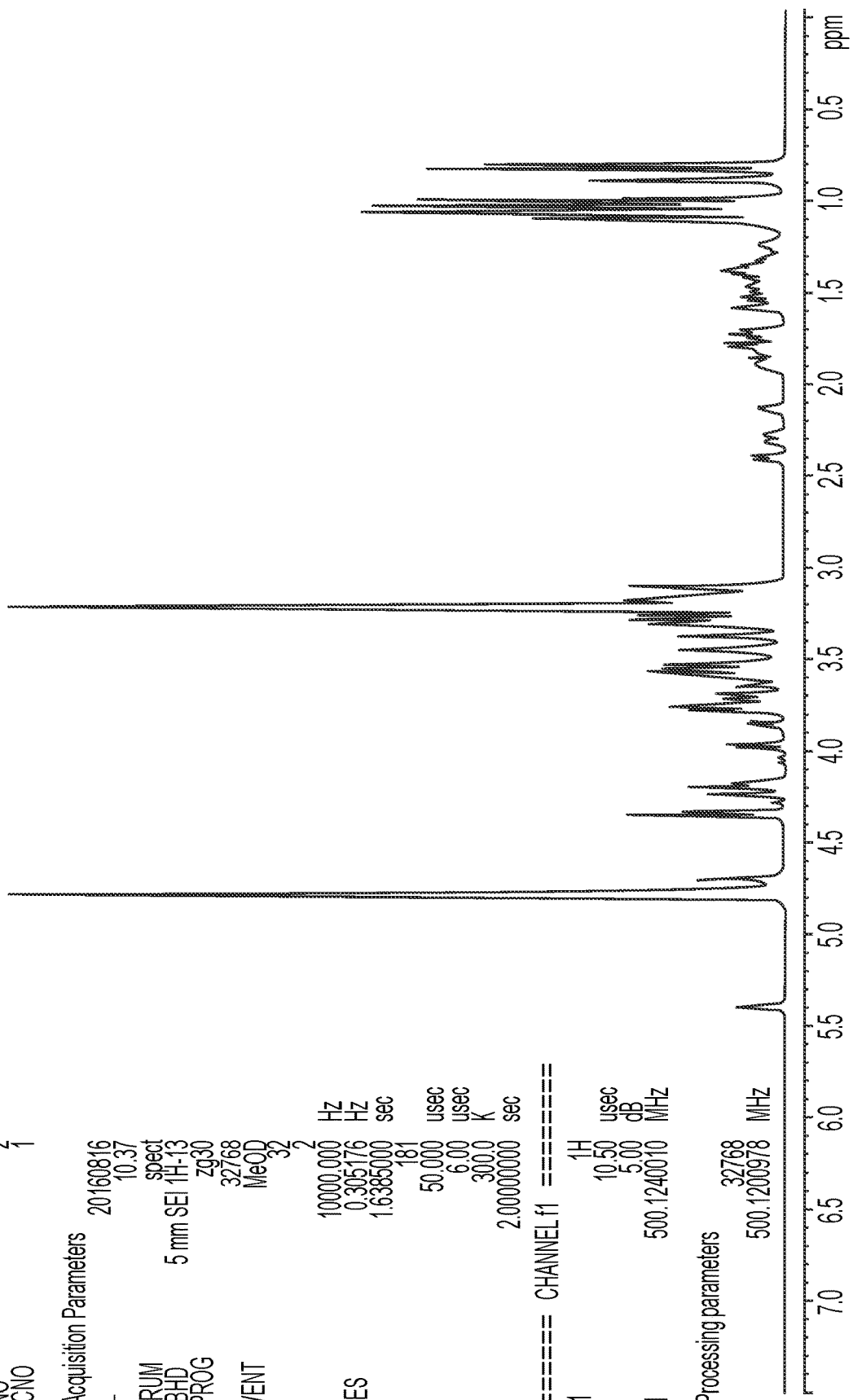
FIG. 44: 1H NMR spectrum of compound 11
Figure 45A:
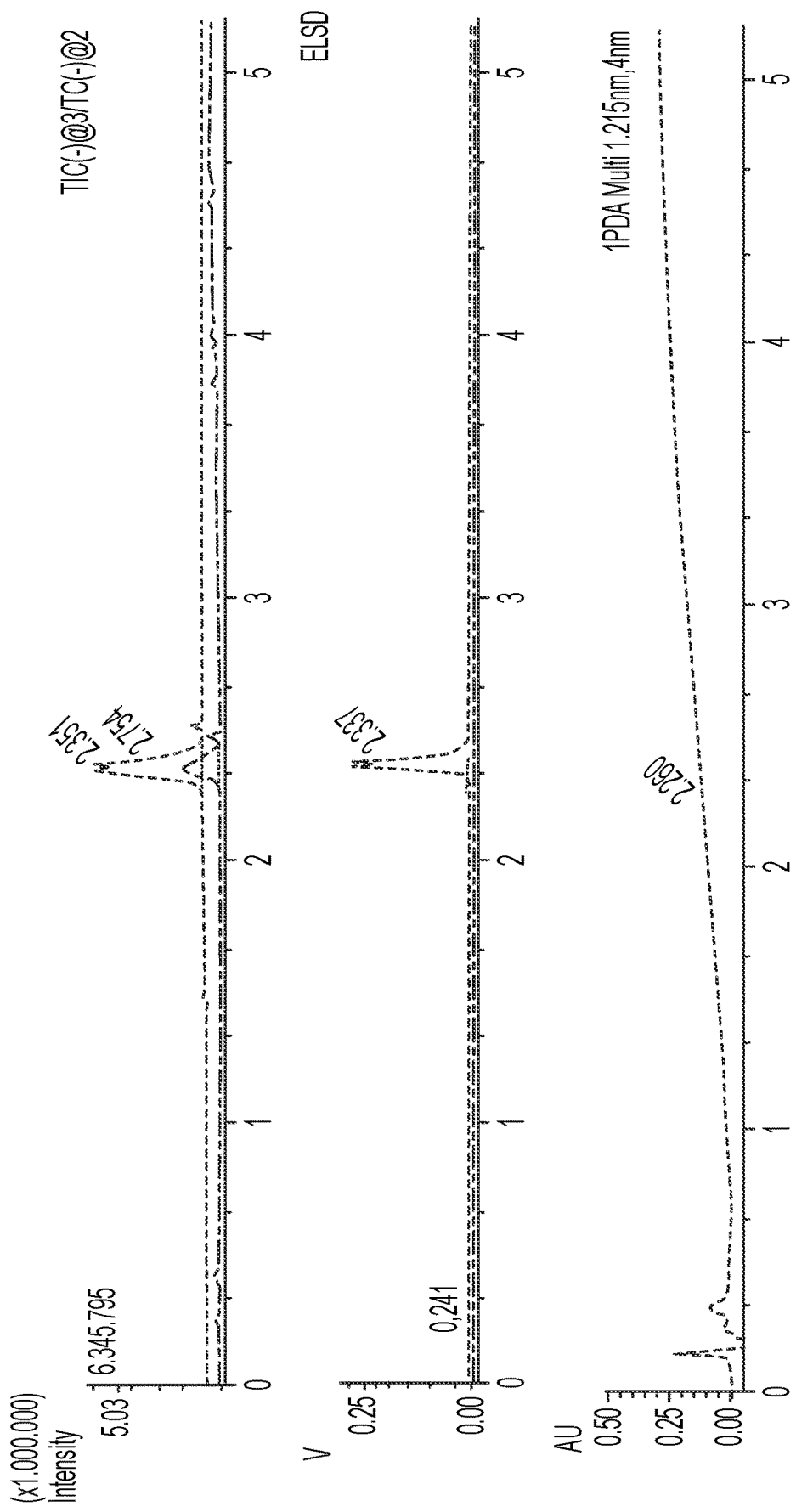
FIG. 45: LCMS of compound 12
Figure 45B:
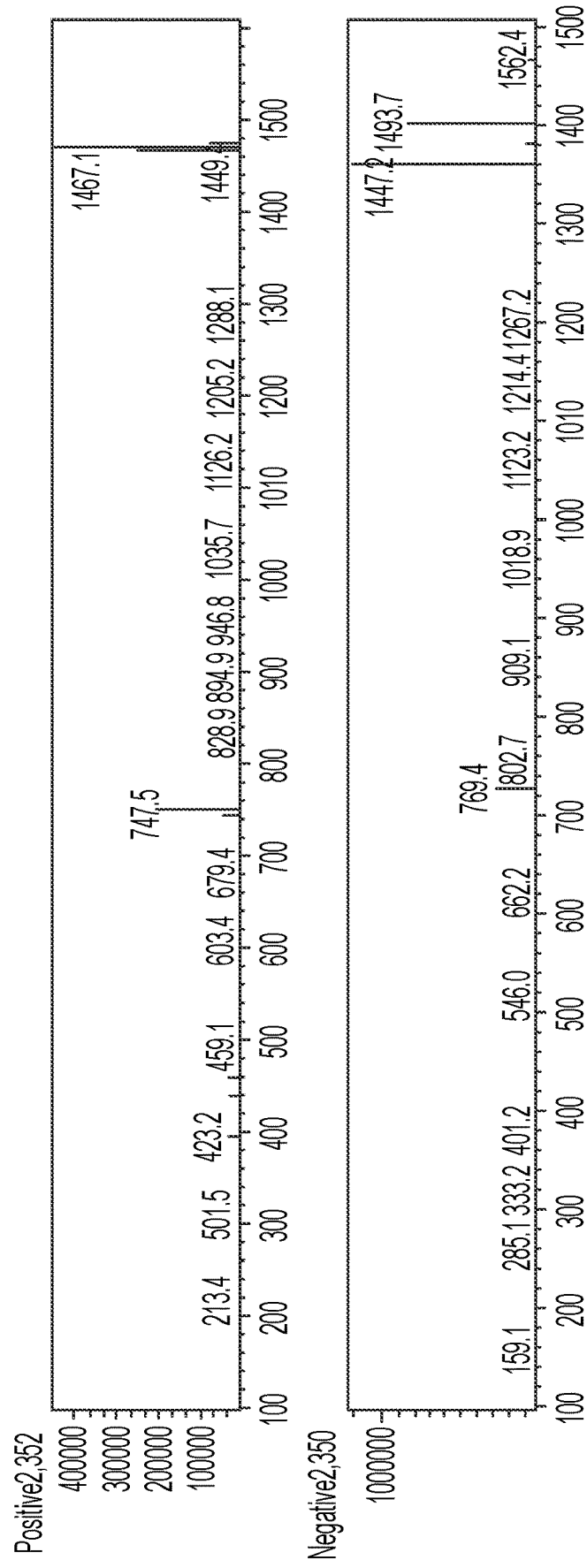
Figure 48:
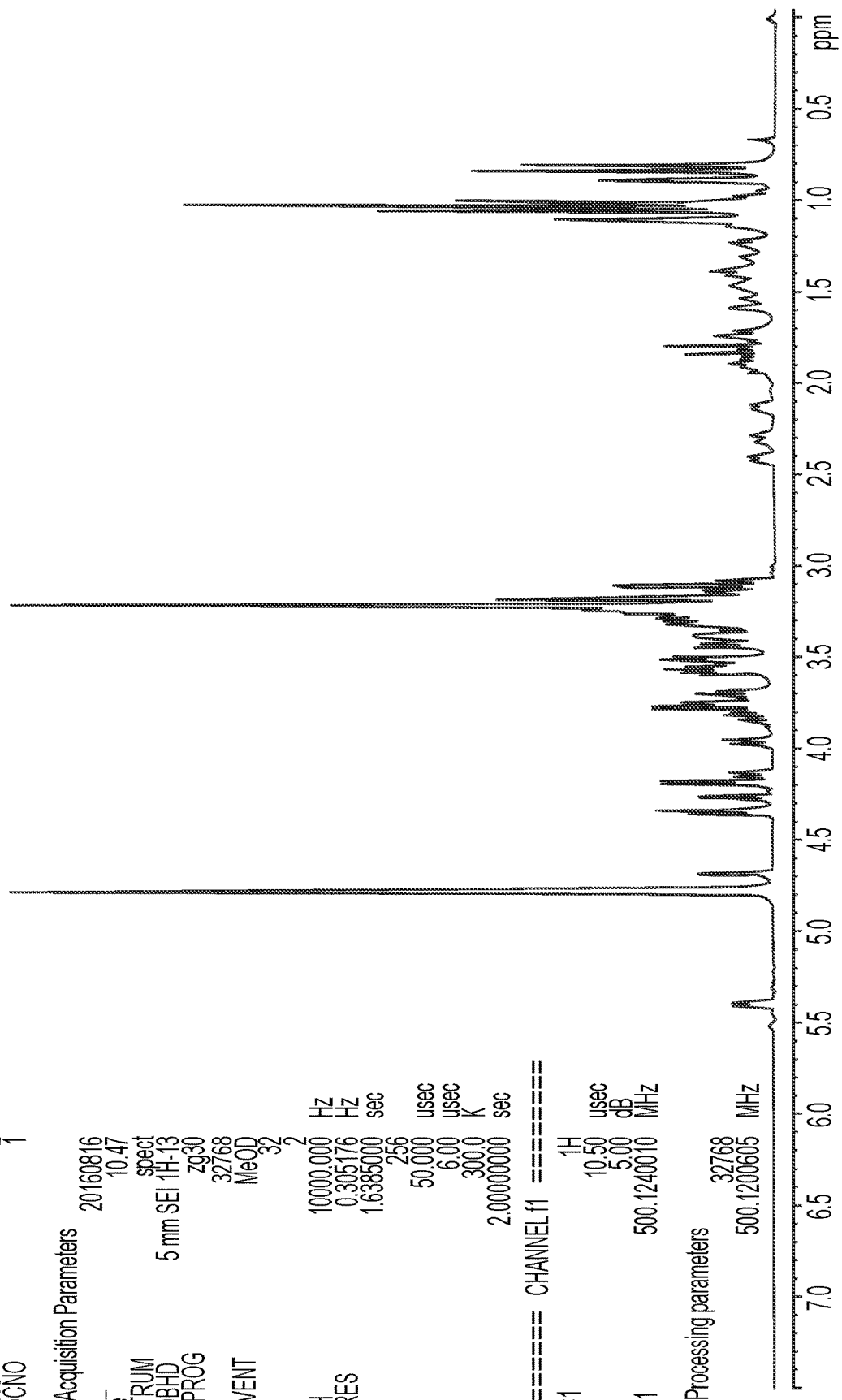
FIG. 48: 1H NMR spectrum of compound 12
Figure 49A:
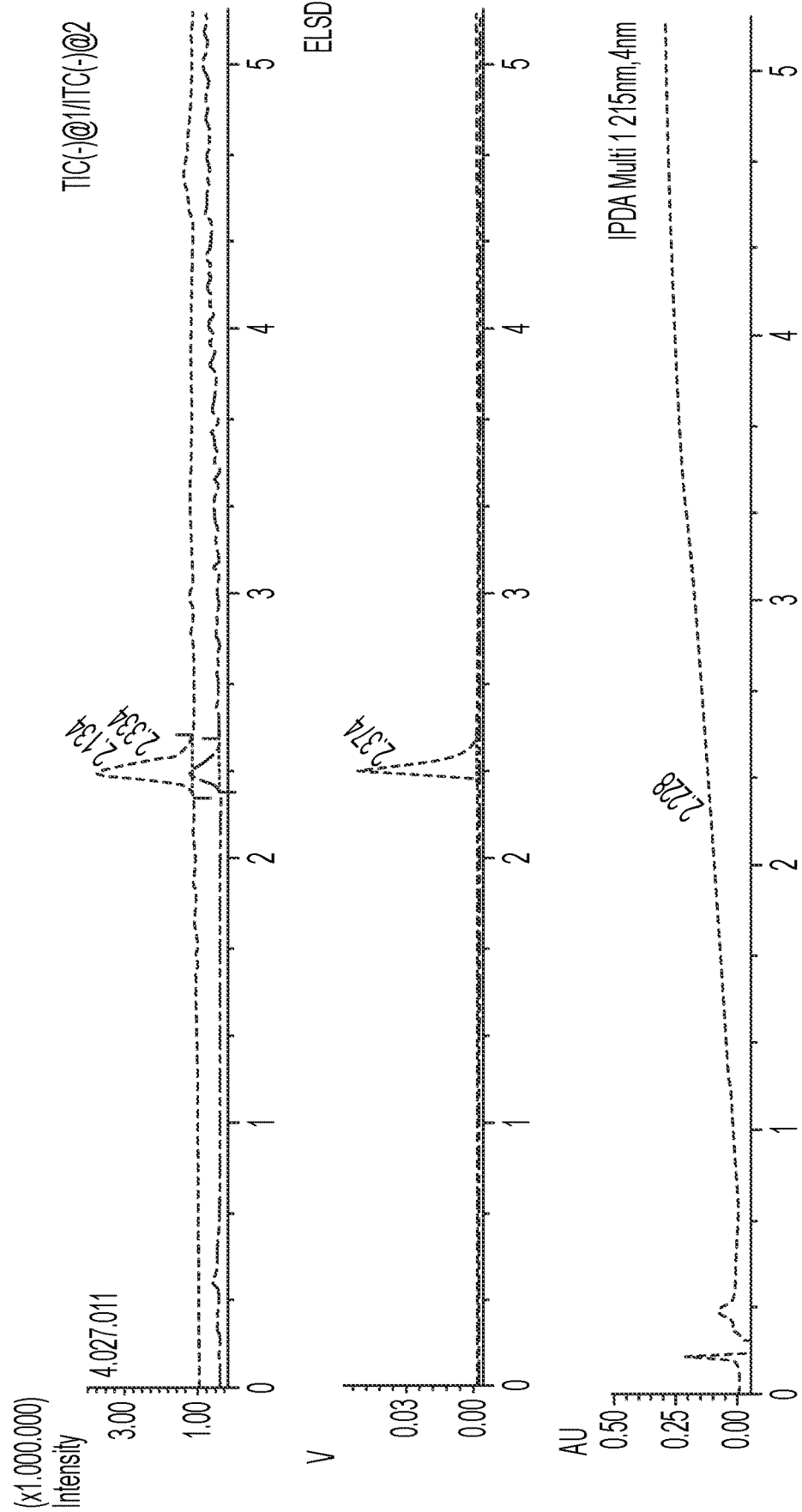
FIG. 49: LCMS of compound 13
Figure 52:
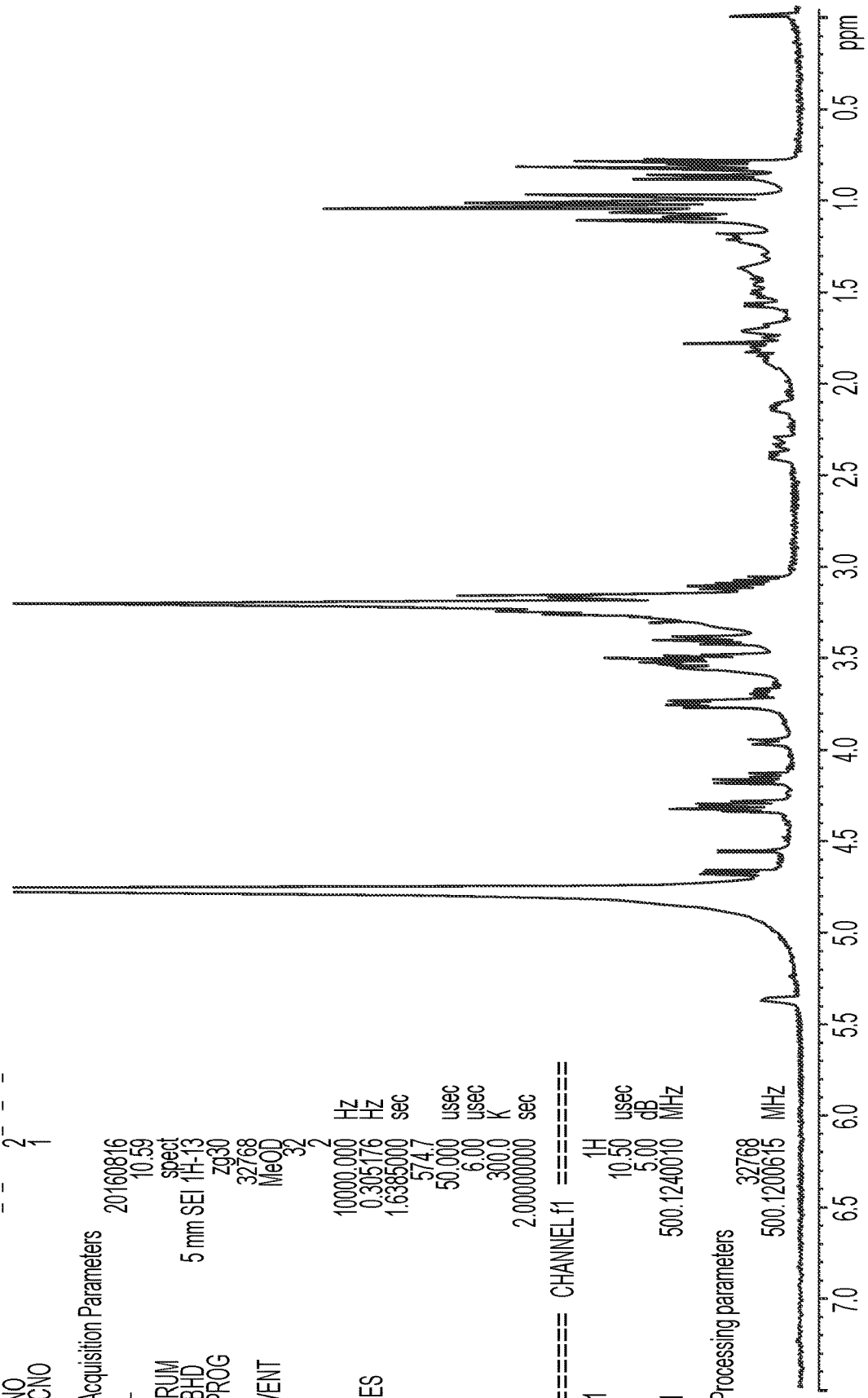
FIG. 52: 1H NMR spectrum of compound 13
Figure 53A:
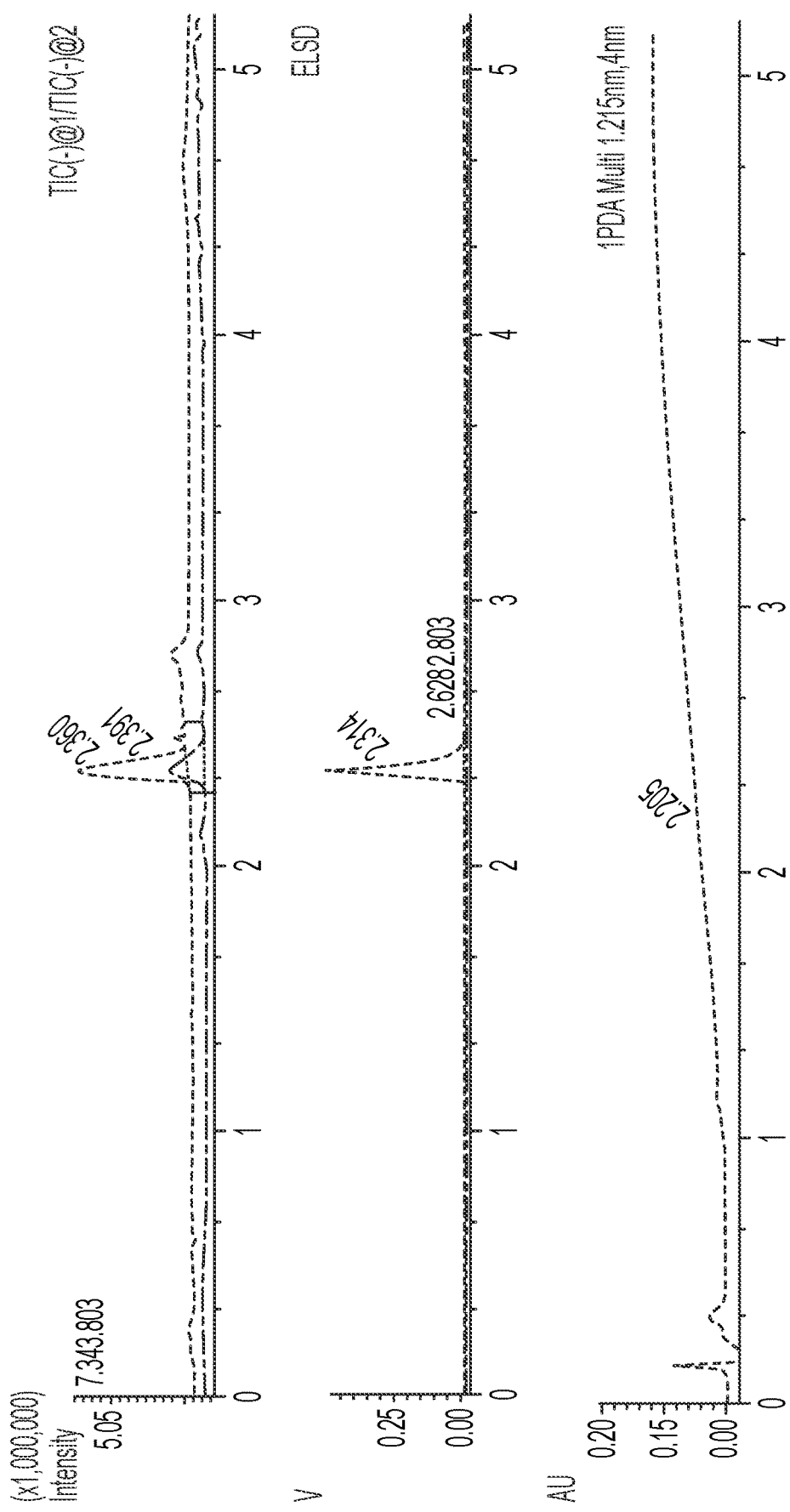
FIG. 53: LCMS of compound 14
Figure 53B:
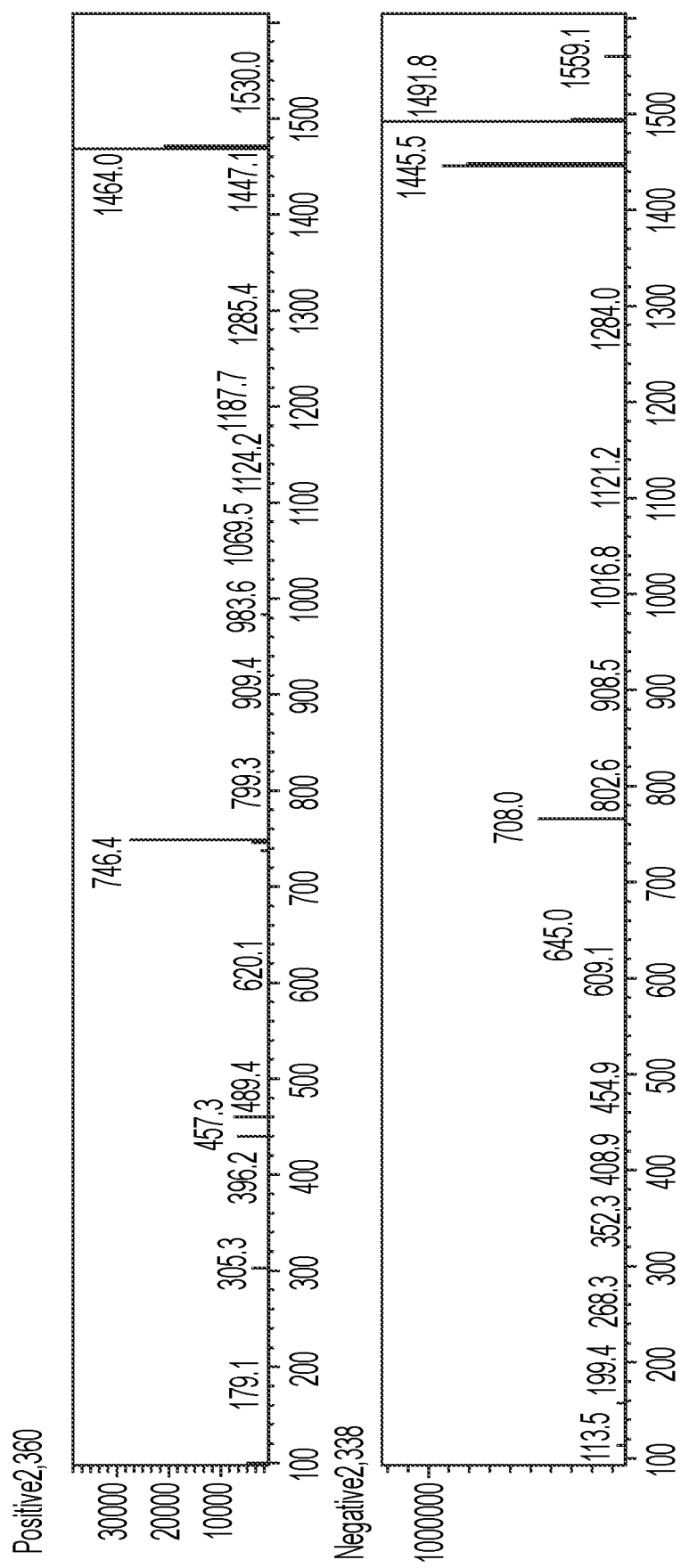
Figure 56:
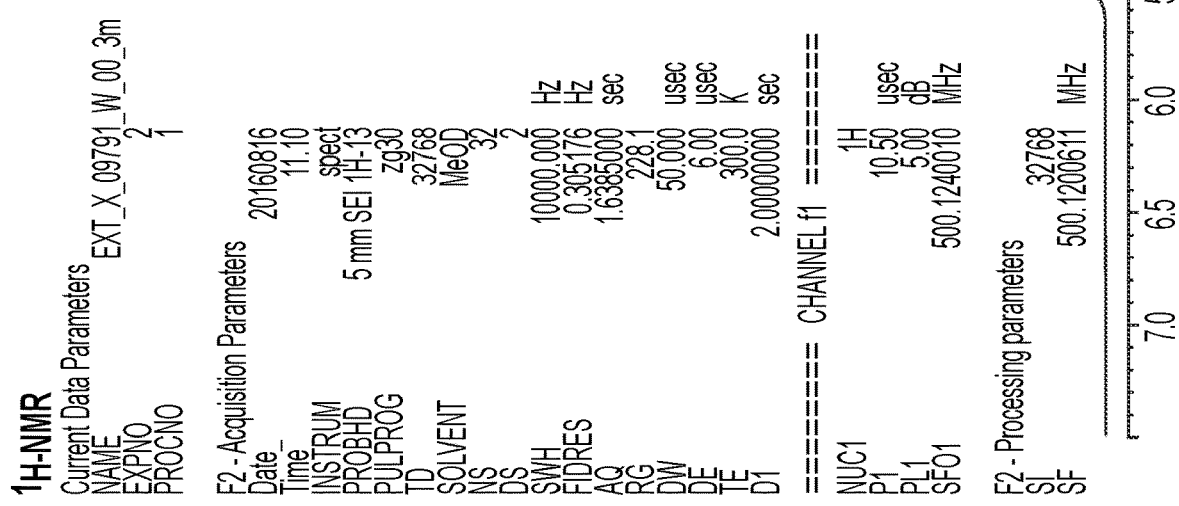
FIG. 56: 1H NMR spectrum of compound 14
Figure 57A:
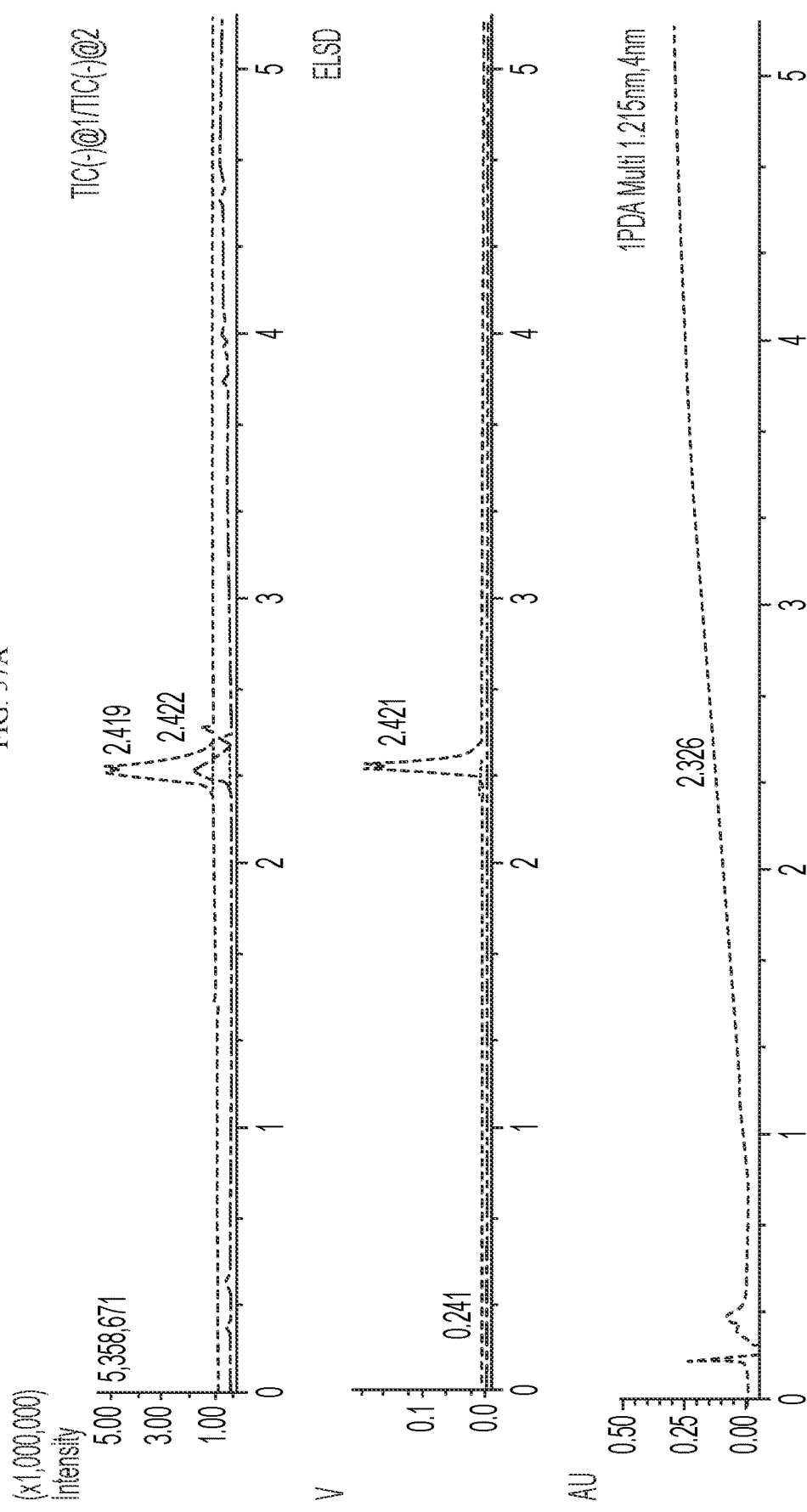
FIG. 57: LCMS of compound 15
Figure 57B:
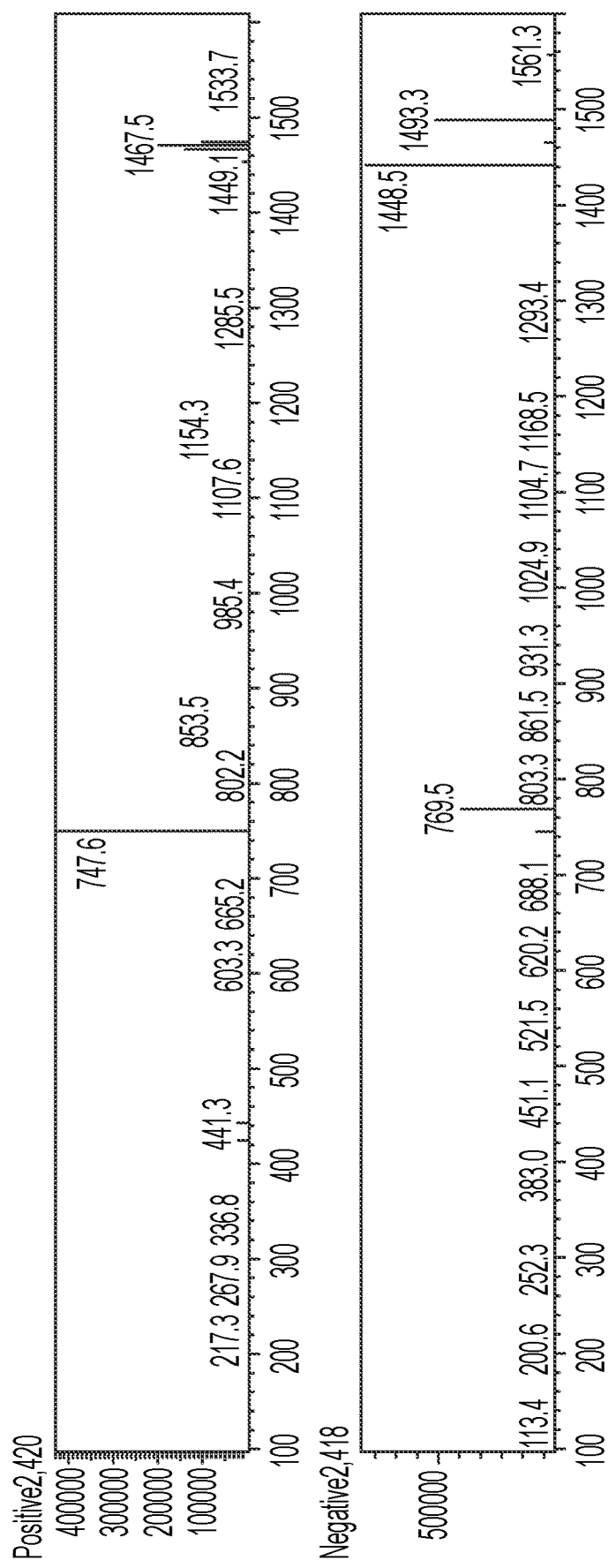
Figure 60:
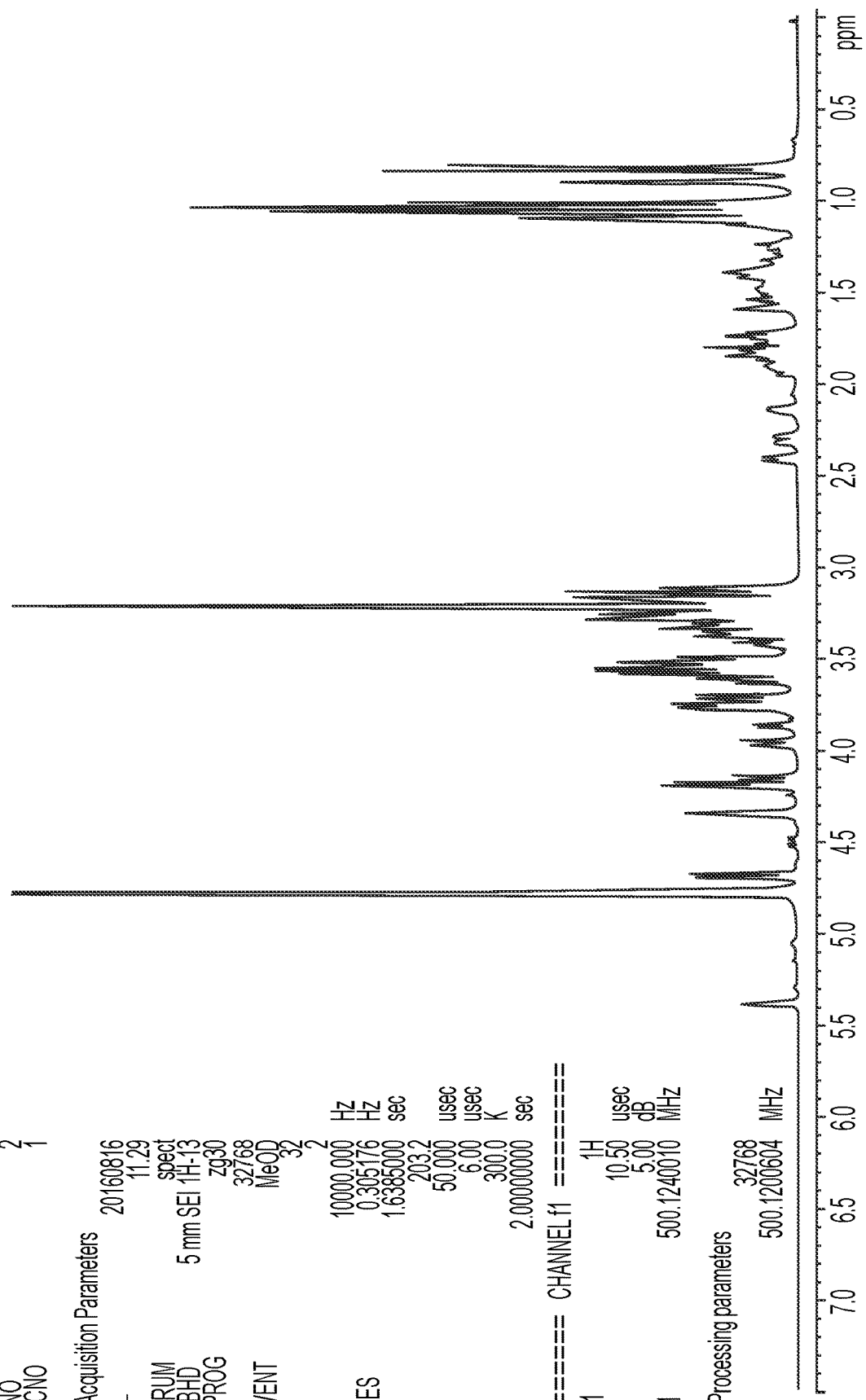
FIG. 60: 1H NMR spectrum of compound 15

Formula 12
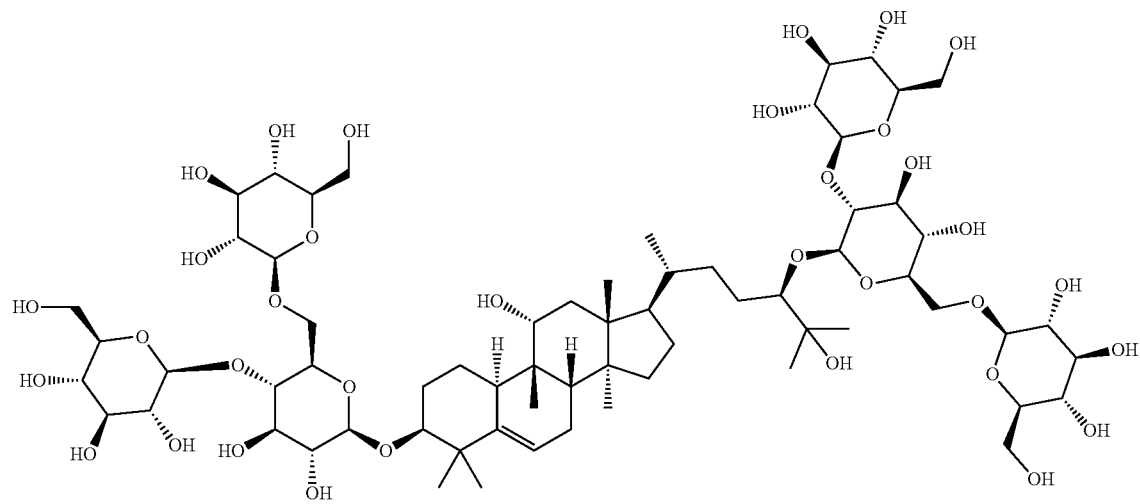
(FIG. 12)
Formula 14
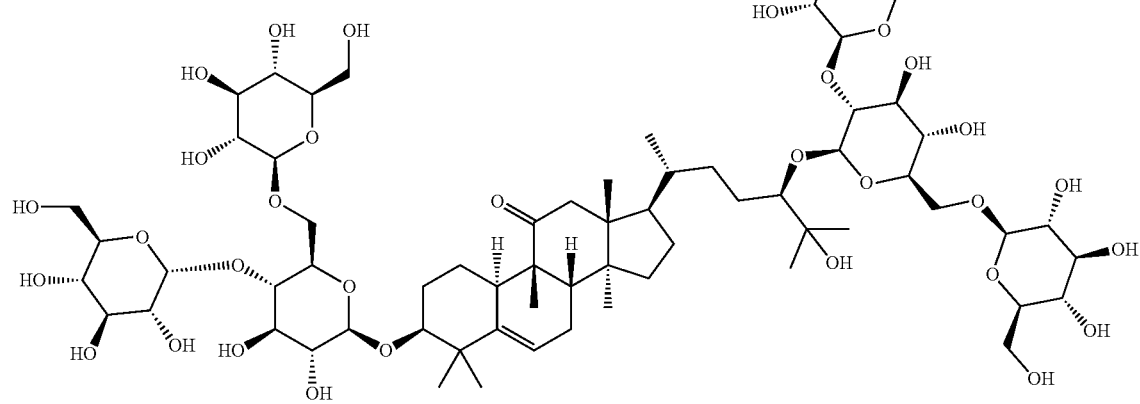
(FIG. 14)

Formula 15

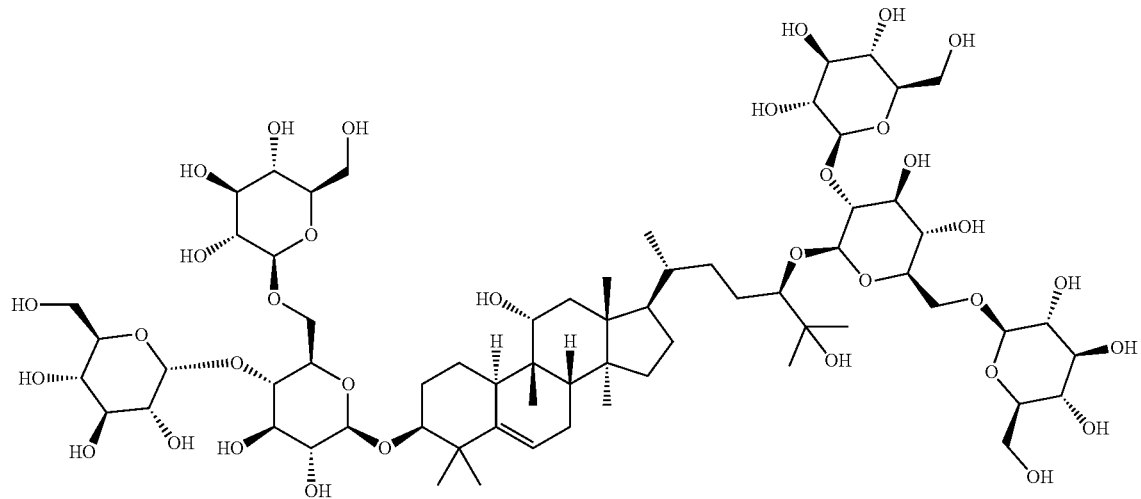

(FIG. 15)

and at least one flavor ingredient, wherein the concentration of at least one isolated or purified mogroside compound is below the threshold flavor recognition concentration of the compound.

2. A composition comprising at least one isolated or purified mogroside compound having a chemical structure represented in any of formulae 1, 2, 4, 5, 7, 8, 9, 11, 12, 14 and 15:

Formula 1

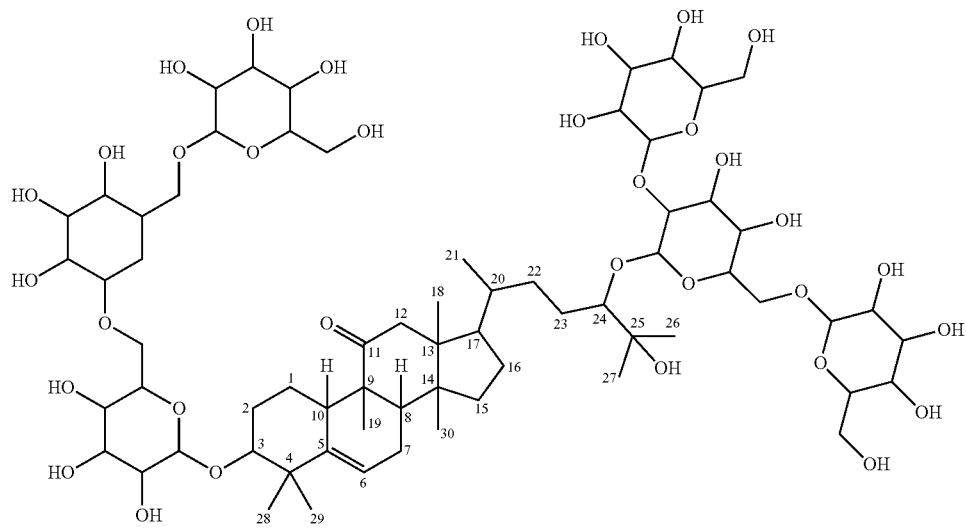

(FIG. 1)

-continued
Formula 2
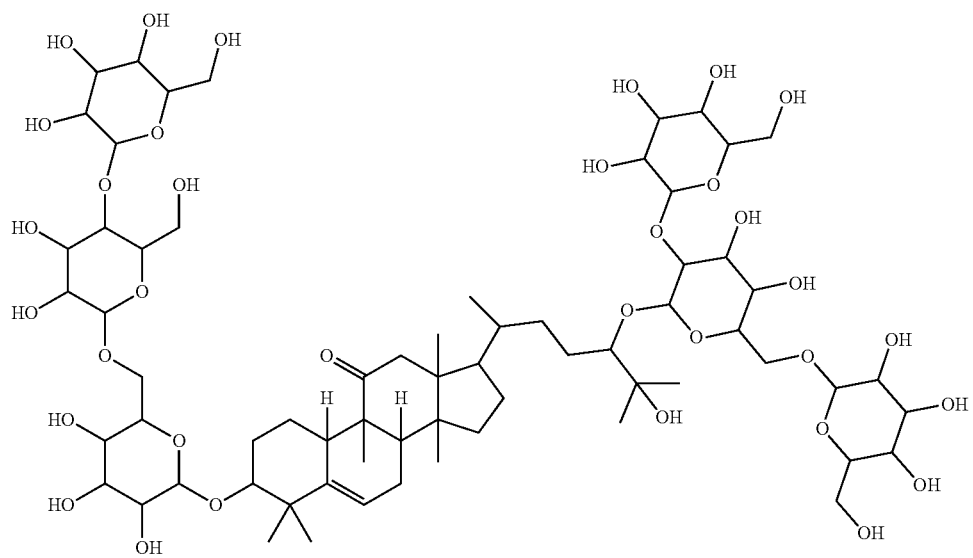
(FIG. 2)
Formula 4
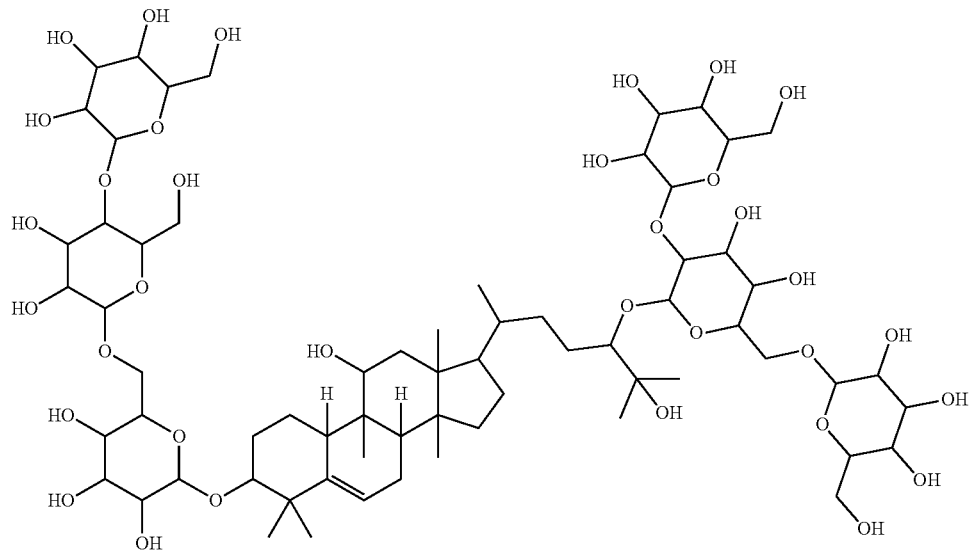
(FIG. 4)

Formula 5
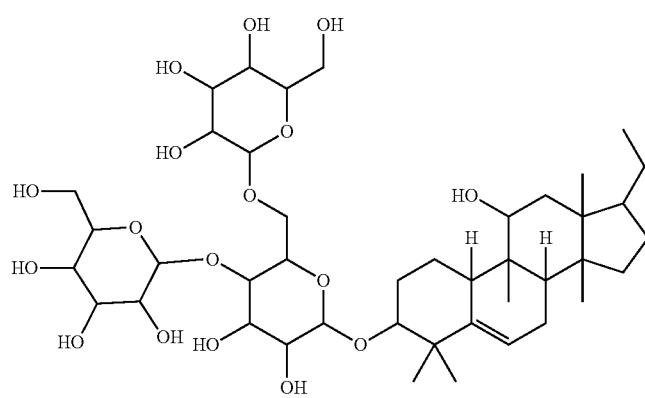
(FIG. 5)
Formula 7
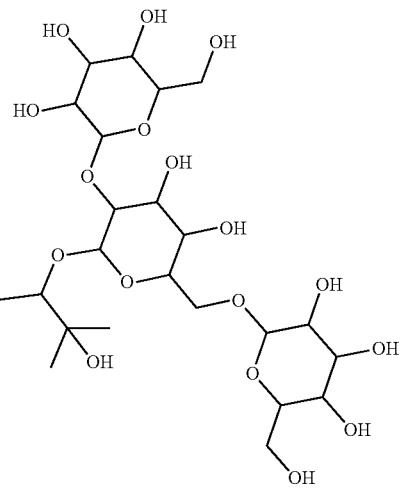
(FIG. 7)
Formula 8
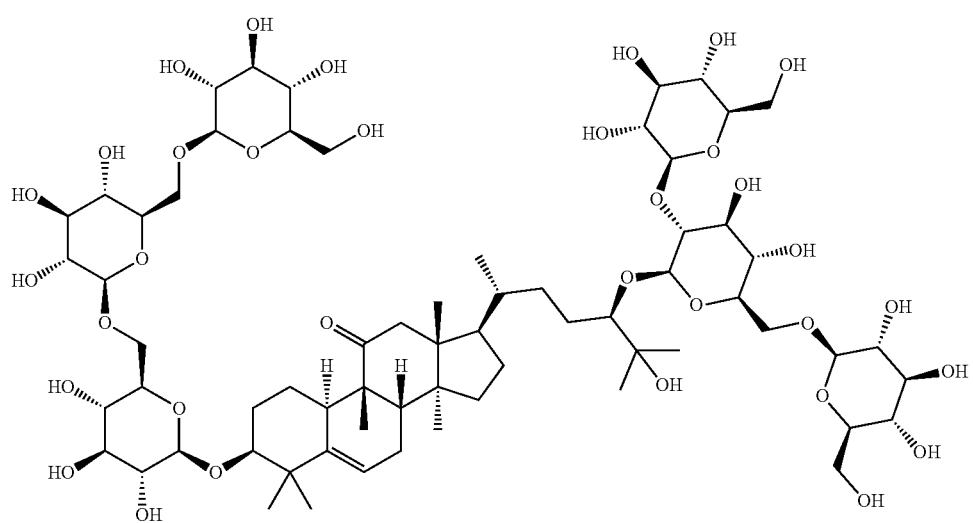
(FIG. 8)

Figure 11:
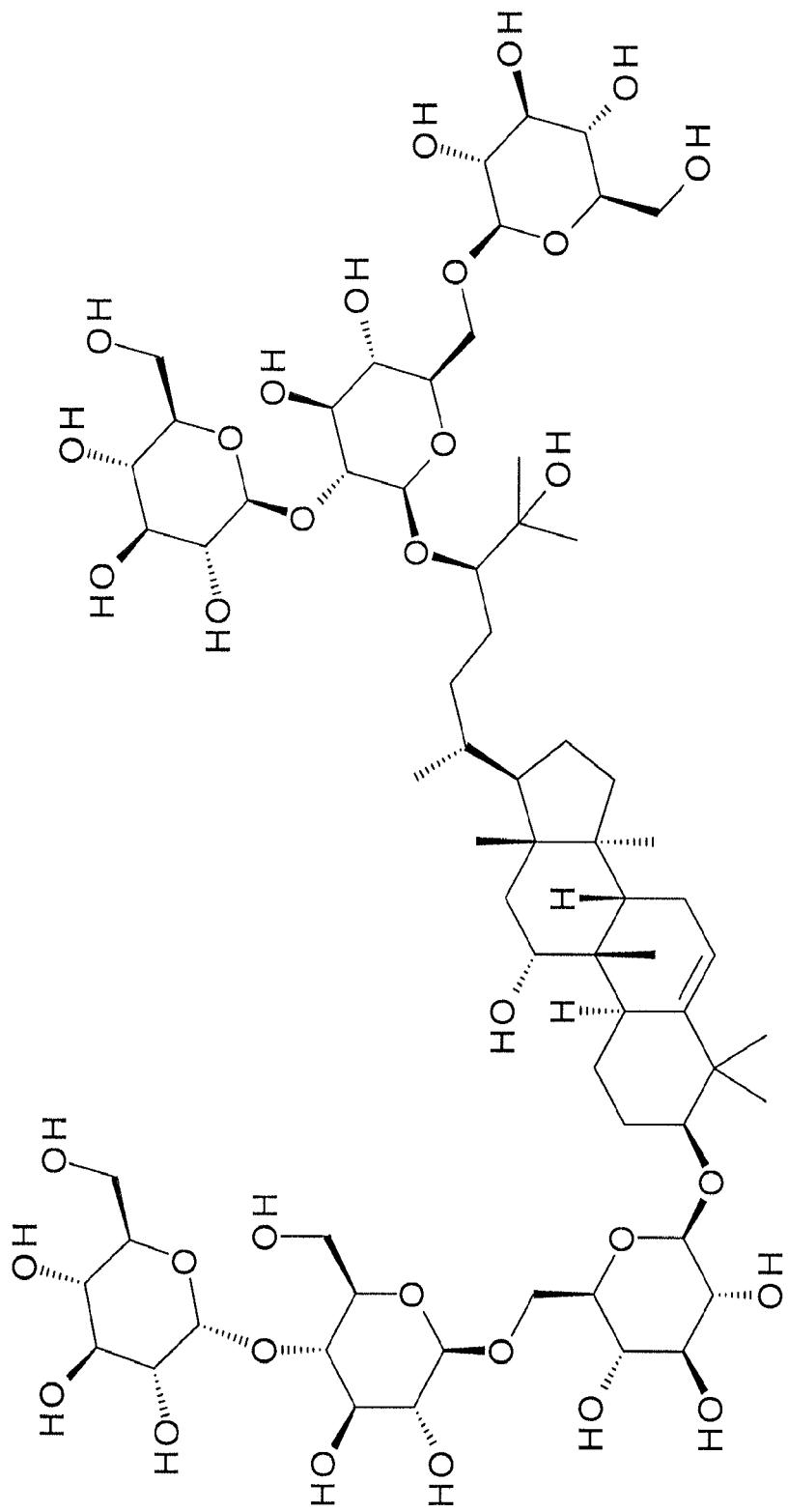
FIG. 11: Chemical structure of novel mogroside compound 11
Figure 12:
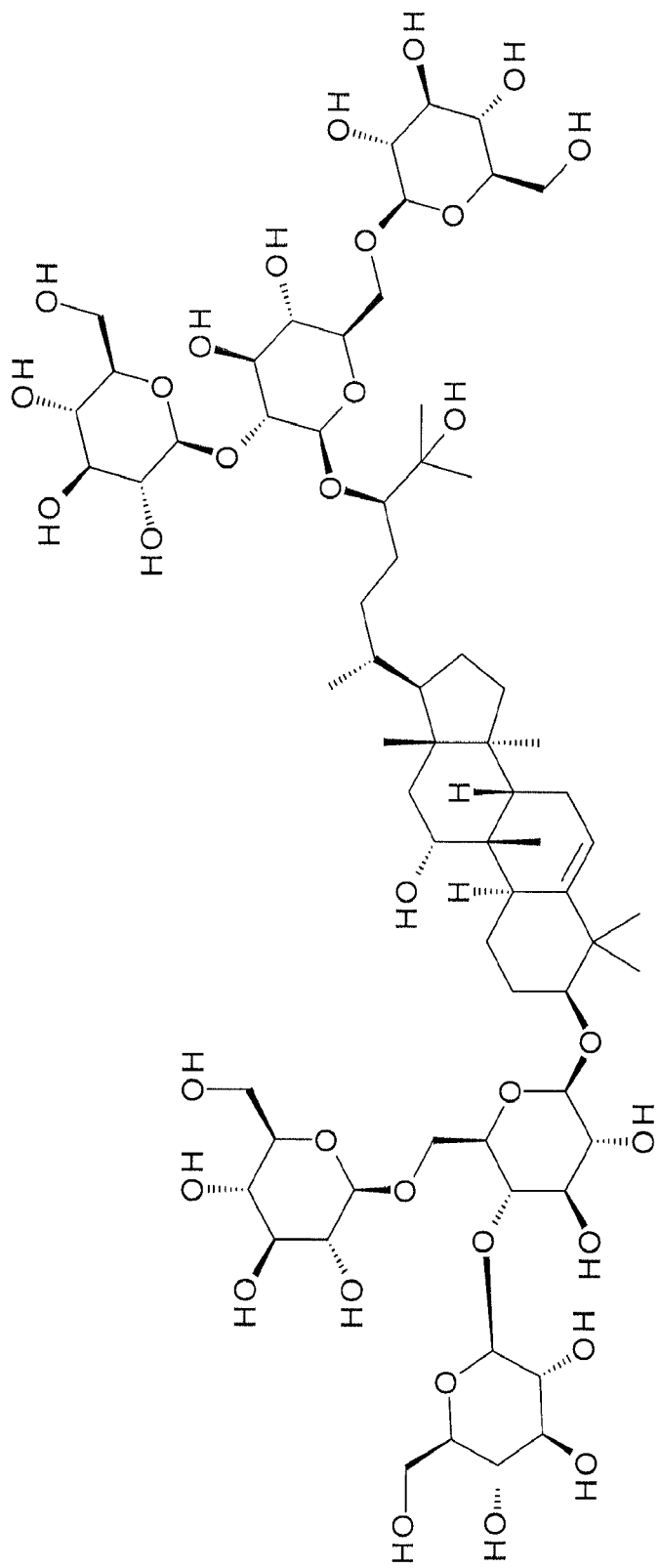
FIG. 12: Chemical structure of novel mogroside compound 12
Figure 13:
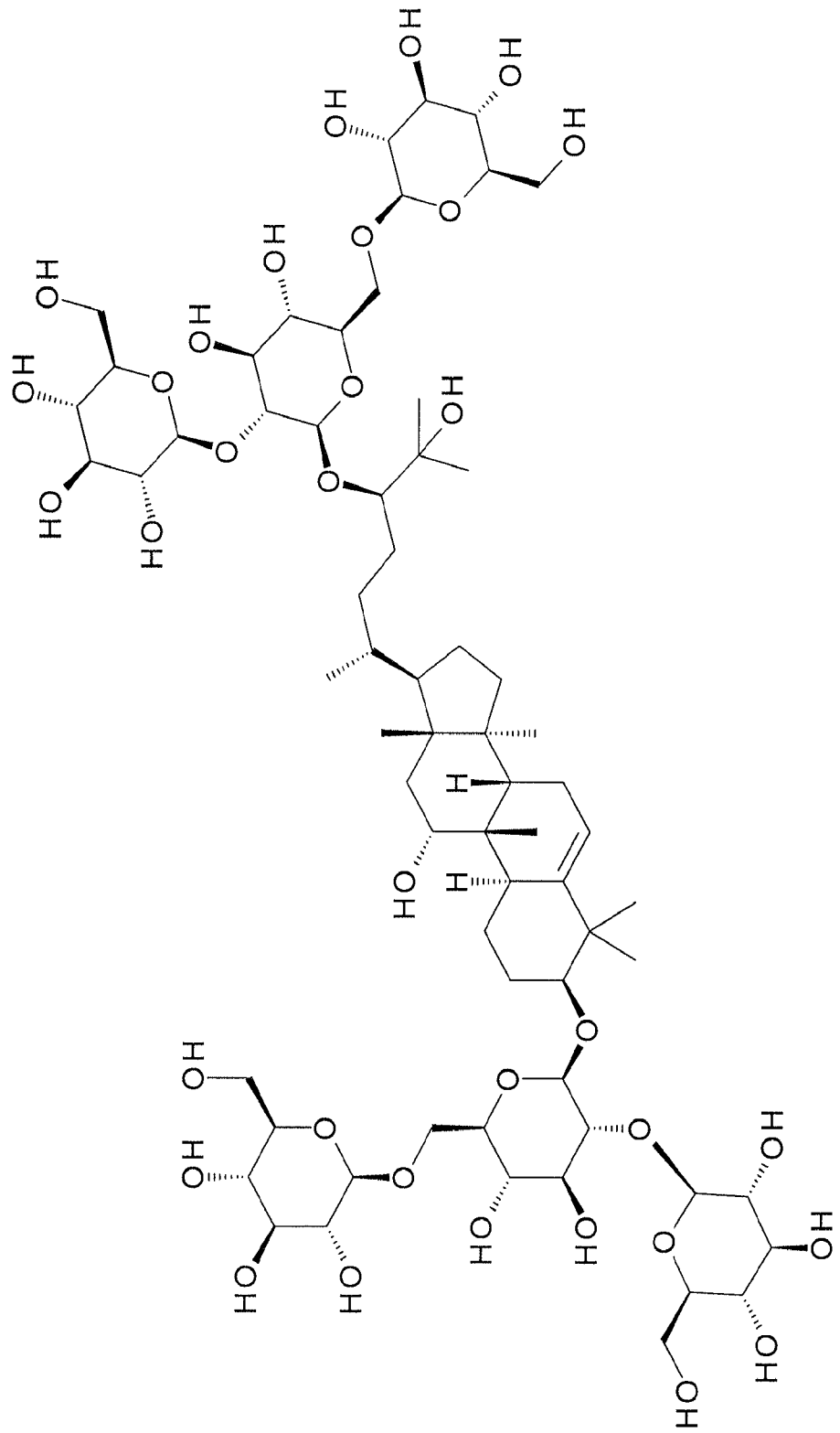
FIG. 13: Chemical structure of novel mogroside compound 13

Formula 9
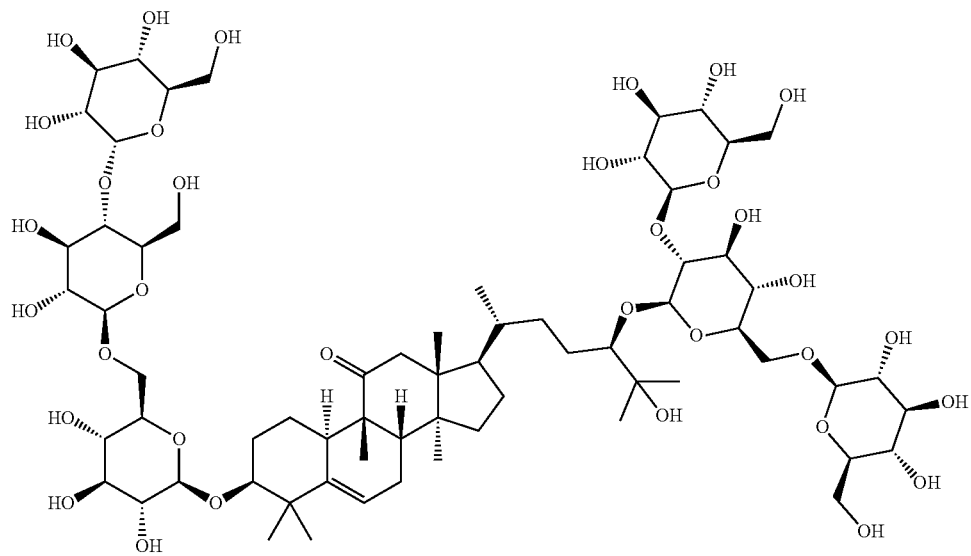
(FIG. 9)
Formula 11
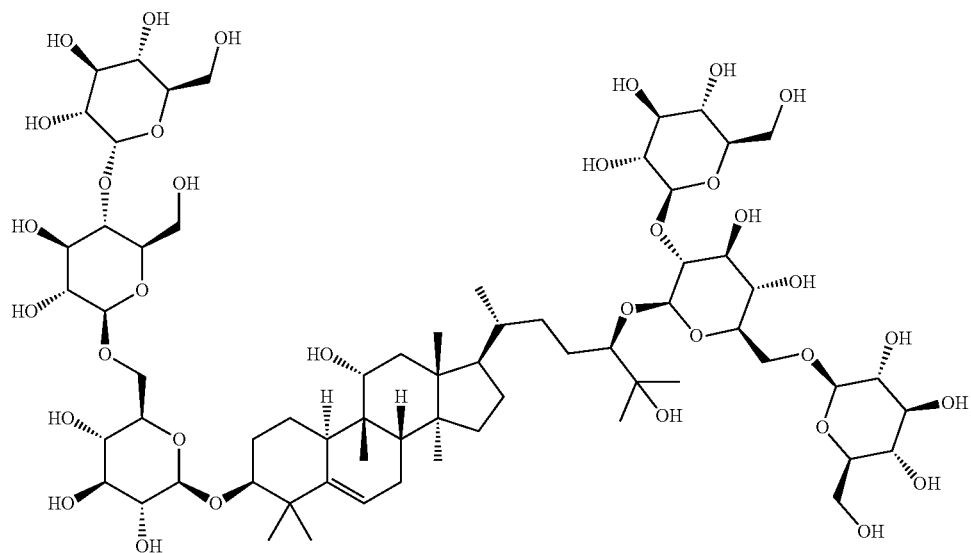
(FIG. 11)

Formula 12
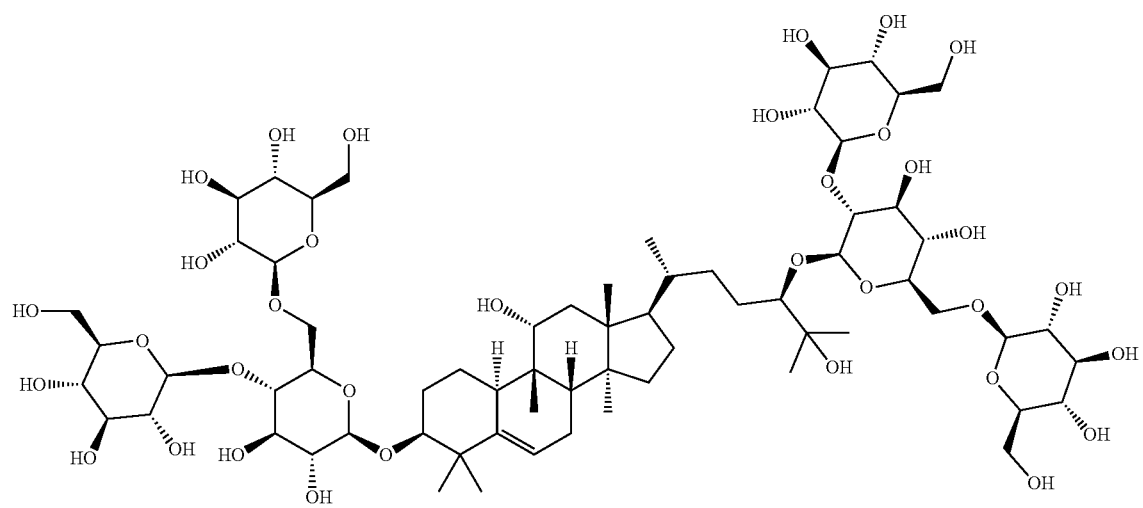
(FIG. 12)
Formula 14
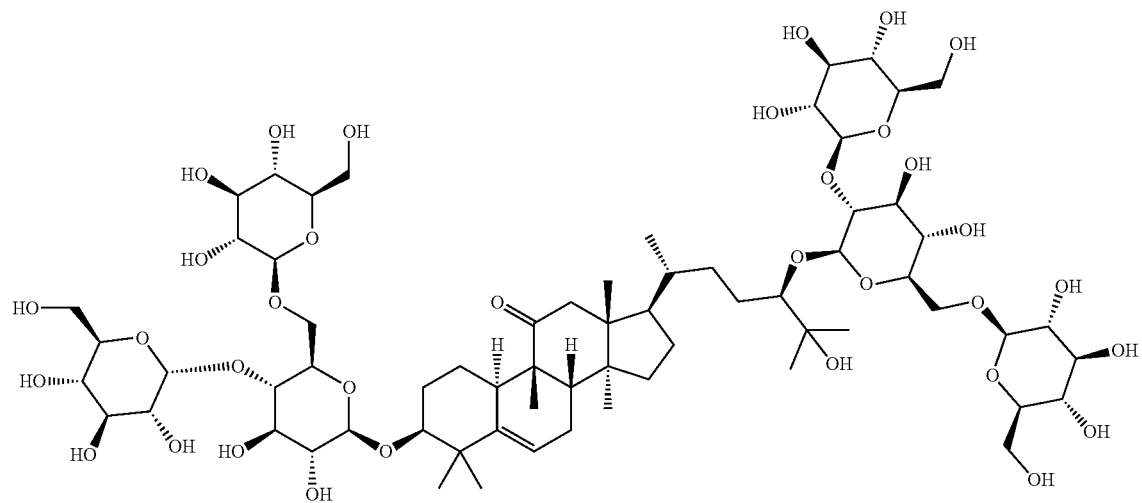
(FIG. 14)

-continued

Formula 15

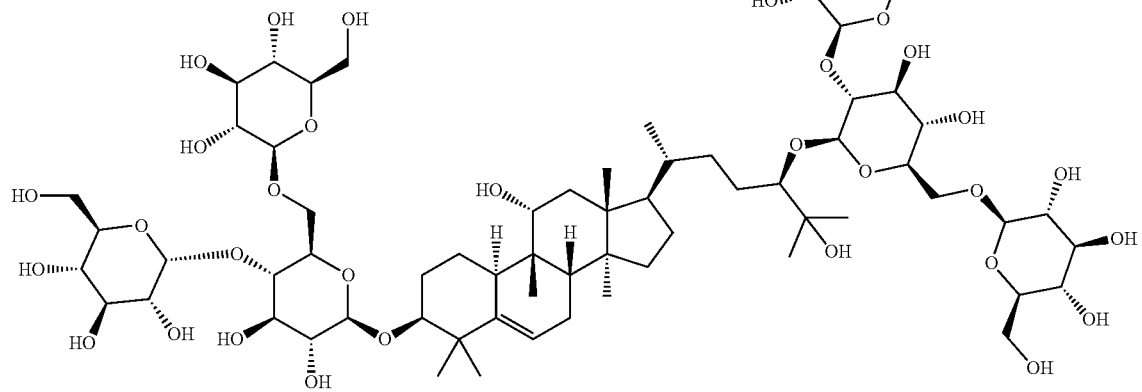

(FIG. 15)

and at least one sweetener, wherein at least one isolated or purified mogroside compound is present in the composition in a concentration below the threshold sweetness recognition concentration of the compound.

3. The composition of claim 2, wherein the sweetener is selected from the group consisting of sucrose, glyceraldehyde, dihydroxyacetone, erythrose, threose, erythrulose, arabinose, lyxose, ribose, xylose, ribulose, xylulose, allose, altrose, allulose, galactose, glucose, gulose, idose, mannose, talose, fructose, psicose, sorbose, tagatose, mannoheptulose, sedoheltulose, octolose, fucose, rhamnose, arabinose, turanose, sialose, inulin, inulooligosaccharides, fructooligosaccharides, HFCS, maltodextrin, coupling sugar, honey, stevia, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, dulcoside A, dulcoside B, rubusoside, steviolbioside, stevioside, other steviol glycosides occurring in *Stevia rebaudiana* plant, biosynthetic steviol glycosides, glycosylated steviol glycosides, glucosylated steviol glycosides (GSGs), mogroside IV, mogroside V, mogroside VI, Luo han guo, siamenoside, other mogrosides occurring in *Siraitia grosvenorii* fruits, monatin and its salts, curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, and cyclocarioside I, sugar alcohols, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, and combinations thereof.

4. A consumable comprising the composition of claim 1 or 2.

5. The consumable of claim 4, wherein the consumable is a beverage or food product.

* * * * *